(12) United States Patent
Matsumoto et al.

(10) Patent No.: US 9,172,045 B2
(45) Date of Patent: Oct. 27, 2015

(54) 4-AMINOCARBAZOLE COMPOUND AND USE THEREOF

(71) Applicant: TOSOH CORPORATION, Yamaguchi (JP)

(72) Inventors: Naoki Matsumoto, Yamaguchi (JP); Takanori Miyazaki, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 14/354,273

(22) PCT Filed: Oct. 25, 2012

(86) PCT No.: PCT/JP2012/077592
§ 371 (c)(1),
(2) Date: Apr. 25, 2014

(87) PCT Pub. No.: WO2013/062043
PCT Pub. Date: May 2, 2013

(65) Prior Publication Data
US 2014/0296519 A1 Oct. 2, 2014

(30) Foreign Application Priority Data
Oct. 26, 2011 (JP) .................................. 2011-235474

(51) Int. Cl.

| | | |
|---|---|---|
| *C07D 405/12* | (2006.01) | |
| *C07D 209/88* | (2006.01) | |
| *C07D 401/14* | (2006.01) | |
| *C07D 403/04* | (2006.01) | |
| *H01L 51/00* | (2006.01) | |
| *C07D 409/04* | (2006.01) | |
| *C07D 409/12* | (2006.01) | |
| *C07D 409/14* | (2006.01) | |
| *C09K 11/06* | (2006.01) | |
| *H05B 33/14* | (2006.01) | |
| *C07D 209/86* | (2006.01) | |
| *H01L 51/50* | (2006.01) | |

(52) U.S. Cl.
CPC .......... *H01L 51/0052* (2013.01); *C07D 209/86* (2013.01); *C07D 209/88* (2013.01); *C07D 401/14* (2013.01); *C07D 403/04* (2013.01); *C07D 405/12* (2013.01); *C07D 409/04* (2013.01); *C07D 409/12* (2013.01); *C07D 409/14* (2013.01); *C09K 11/06* (2013.01); *H01L 51/0058* (2013.01); *H01L 51/0061* (2013.01); *H01L 51/0072* (2013.01); *H01L 51/0073* (2013.01); *H01L 51/0074* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/5016* (2013.01); *H01L 51/5056* (2013.01)

(58) Field of Classification Search
USPC ............... 548/159, 442, 305.1; 546/159, 256, 546/276.7
See application file for complete search history.

(56) References Cited

U.S. PATENT DOCUMENTS

| | | |
|---|---|---|
| 5,049,464 A | 9/1991 | Kanemaru et al. |
| 7,431,997 B2 | 10/2008 | Hwang et al. |
| 2005/0221124 A1 | 10/2005 | Hwang et al. |
| 2005/0225235 A1 | 10/2005 | Kim et al. |

(Continued)

FOREIGN PATENT DOCUMENTS

| | | |
|---|---|---|
| JP | 02-178670 | 7/1990 |
| JP | 2003-316035 | 11/2003 |

(Continued)

OTHER PUBLICATIONS

M.A. Baldo et al., "Very high-effidiendy green organic light-emitting devices based on electrophosphorescence", Applied Physics Letters, Jul. 5, 1999, pp. 4-6, vol. 75, No. 1.

(Continued)

*Primary Examiner* — Nyeemah A Grazier
(74) *Attorney, Agent, or Firm* — Greenblum & Bernstein, P.L.C.

(57) ABSTRACT

A 4-aminocarbazole compound represented by formula (1):

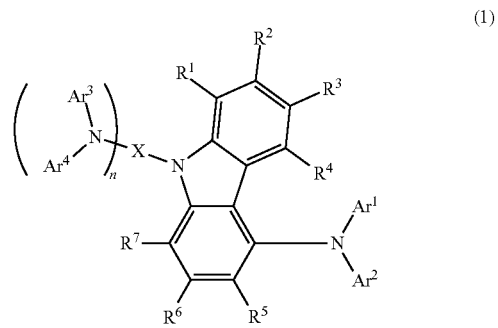

wherein $Ar^1$-$Ar^4$ represent substituted or unsubstituted aryl, thienyl, pyridyl, benzothienyl, dibenzothienyl, dibenzofuranyl, 4-carbazolyl, dibenzothienylphenyl, dibenzofuranylphenyl or 9-carbazolylphenyl group; $R^1$-$R^7$ represent substituted or unsubstituted aryl, heteroaryl or heteroarylphenyl group, or alkyl, alkoxy, cyano group, or hydrogen or halogen atom; n is integer of 0-2; and X represents substituted or unsubstituted (n+1)-valent aromatic hydrocarbon, heteroaromatic or heteroarylphenyl group. The 4-aminocarbazole compound provides an organic EL device exhibiting enhanced emitting efficiency and durability.

15 Claims, No Drawings

(56) References Cited

U.S. PATENT DOCUMENTS

| | | |
|---|---|---|
| 2006/0020136 A1 | 1/2006 | Hwang et al. |
| 2006/0115680 A1 | 6/2006 | Hwang et al. |
| 2007/0231503 A1 | 10/2007 | Hwang et al. |
| 2008/0107919 A1 | 5/2008 | Hwang et al. |
| 2008/0145708 A1 | 6/2008 | Heil et al. |
| 2008/0254318 A1 | 10/2008 | Nakashima et al. |
| 2008/0284328 A1 | 11/2008 | Nakashima et al. |
| 2010/0033081 A1 | 2/2010 | Yamada et al. |
| 2012/0175598 A1 | 7/2012 | Balaganesan et al. |
| 2012/0203010 A1* | 8/2012 | Matsumoto et al. .......... 548/440 |
| 2013/0234118 A1* | 9/2013 | Kwon et al. .................... 257/40 |
| 2014/0027747 A1 | 1/2014 | Mun et al. |

FOREIGN PATENT DOCUMENTS

| | | |
|---|---|---|
| JP | 2005-154421 | 6/2005 |
| JP | 2006-028176 | 2/2006 |
| JP | 2006-056841 | 3/2006 |
| JP | 2006-151979 | 6/2006 |
| JP | 2006-298895 | 11/2006 |
| JP | 2006-298898 | 11/2006 |
| JP | 2007-520470 | 7/2007 |
| JP | 2008-019238 | 1/2008 |
| JP | 2008-044923 | 2/2008 |
| JP | 2008-078362 | 4/2008 |
| JP | 2008-195841 | 8/2008 |
| JP | 2011-001349 | 1/2011 |
| JP | 2012/049518 | 3/2012 |
| KR | 2009-0129799 | 12/2009 |
| KR | 2010-0005903 | 1/2010 |
| KR | 2010-0071723 | 6/2010 |
| KR | 2010-0073543 | 7/2010 |
| KR | 2011-0117548 | 10/2011 |
| WO | 2005/040117 | 5/2005 |
| WO | 2005/090512 | 9/2005 |
| WO | 2006/108497 | 10/2006 |
| WO | 2012/011756 | 1/2012 |
| WO | 2012/077520 | 6/2012 |
| WO | 2012/134203 | 10/2012 |

OTHER PUBLICATIONS

Naoki Matsumoto et al., "Esciplex Formations between Tris(8-hydoxy quinolate)aluminium and Hole Transport Materials and Their Phtoluminescence and Electroluminescence Characteristics", journal of Physical Chemistry C, Apr. 26, 2008, pp. 7735-7741, vol. 112.

R.J. Holmes et al., "Blue organic electrophosphoresc using exothermic host-quest energy transfer", Applied Physics Letters, Apr. 14, 2003, pp. 2422-2424, vol. 82, No. 15.

Kenichi Goushi et al., "Triplet exciton confinement and unconfinement by adjacent hole-transport layers", Journal of Applied Physics, Jun. 15, 2004, pp. 7798-7802, vol. 95, No. 12.

International Search Report issued Nov. 20, 2012 in PCT/JP2012/077592.

* cited by examiner

4-AMINOCARBAZOLE COMPOUND AND USE THEREOF

TECHNICAL FIELD

This invention relates to a novel 4-aminocarbazole compound and an organic electroluminescent device comprising the compound.

BACKGROUND ART

An organic electroluminescent (hereinafter abbreviated to "EL" when appropriate) device is a planar light emitting device having a structure such that an organic thin film is sandwiched between a pair of electrodes, and is characterized as being thin and light-weight and having a wide view angle and a high speed response, therefore, is expected to be suitable for various display devices. Recently organic EL devices have been practically applied as a display for personal digital assistants such as a cell phone.

The organic EL device utilizes light emission occurring due to the recombination of electron injected from a cathode with hole injected from an anode, which occurs in the emitting layer. Most organic EL devices have a multilayer structure comprising a hole transport layer, an emitting layer and an electron transport layer. Charge transport layers such as the hole transport layer and the electron transport layer themselves do not emit light, but have a function of promoting injection of an electron into the emitting layer and confining electrons injected into the emitting layer and energies of an exciton formed in the emitting layer. Thus, the electron transport layer plays an important role for improving low-voltage drivability and emitting efficiency of organic EL devices.

As a hole transport material, an amine compound having an appropriate ionization potential and a hole-transportability is used. Such hole transport material includes, for example, well-known 4,4'-bis[N-(1-naphthyl)-N-phenyl]biphenyl (hereinafter abbreviated to as "NPD"). However, an organic EL device having a hole transport layer comprising NPD does not exhibit driving voltage and emitting efficiency to a satisfying extent, and hence, a novel hole transport material is eagerly desired.

In recent years, an organic EL device having an emitting layer comprising a phosphorescent material has been developed. A hole transport material having a high triplet level is required for the organic EL device using a phosphorescent material. From a viewpoint of triplet level, NPD is not sufficient. For example, it is known that an organic EL device using a combination of NPD with a phosphorescent material emitting a green light exhibits a low emitting efficiency (see non-patent document 1, below).

In view of the above-mentioned background, it has been recently proposed to utilize a compound having an aromatic cyclic hydrocarbon group having introduced therein carbazole ring(s), specifically, a 3-aminocarbazole compound (see for example, patent documents 1 and 2) and a 2-aminocarbazole compound (see for example, patent documents 3 and 4).

However, the measurement of the 3-amoinocarbazole compound by the inventors revealed that their ionization potentials are lower than that of NPD although the compound have a higher triplet level than that of NPD. It is presumed that the low ionization potential of the 3-aminocarbazole compounds is due to the fact that the amino group in the carbazole ring is activated by the nitrogen atom at 9-position of the carbazole ring.

Ionization potential of a material plays an important role for the characteristics of an organic EL device. Especially when the material is used in a hole transport layer adjacent to an emitting layer, the ionization potential of the material greatly influences upon emitting efficiency of an organic EL device. For example, when a material having a low ionization potential is used in a hole transport layer adjacent to an emitting layer, the emitting efficiency of an organic EL device is greatly reduced by the exciplex formed between the hole transport layer and the emitting layer (see, for example, non-patent document 2). Therefore, an organic EL device having a hole transport layer comprised of 3-aminocarbazole compound does not exhibit a sufficiently high emitting efficiency.

The 2-aminocarbazole compound has an ionization potential equal to or higher than that of NPD, and a triplet level higher than that of NPD. In organic EL devices using a green phosphorus luminescent material, the 2-aminocarbazole compound exhibits a higher emitting efficiency than that of NPD. But, a material exhibiting a still higher emitting efficiency is eagerly desired.

PRIOR ART DOCUMENT

Patent Document

Patent document 1: JP 2006-28176A
Patent document 2: JP 2006-298898
Patent document 3: KR 2009-0129799
Patent document 2: JP 2011-001349

Non-Patent Document

Non-patent document 1: Journal of Applied Physics, 2004, vol. 95, P7798
Non-patent document 2: Journal of Physical Chemistry C, 2008, vol. 112, P7735

SUMMARY OF THE INVENTION

Problems to be Solved by the Invention

In view of the foregoing, a primary object of the present invention is to provide a compound having appropriate ionization potential and high triplet level, and giving an organic EL device exhibiting improved emitting efficiency.

Means for Solving the Problems

The inventors made an extensive research and found that a 4-aminocarbazole compound represented by the following general formula (1) (hereinafter referred to as "formula (1)") has appropriate ionization potential and high triplet level, and gives an organic EL device exhibiting improved emitting efficiency and current efficiency.

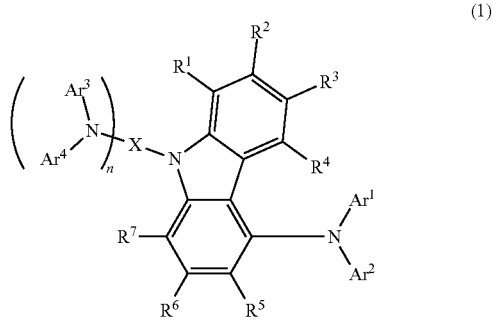

(1)

In formula (1), $Ar^1$ through $Ar^4$ independently represent an aryl group having 6 to 30 carbon atoms, a thienyl group, a pyridyl group, a benzothienyl group, a dibenzothienyl group, a dibenzofuranyl group, a 4-carbazolyl group, a dibenzothienylphenyl group, a dibenzofuranylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 11 carbon atoms, a trialkylsilyl group having 3 to 18 carbon atoms, a triarylsilyl group having 18 to 40 carbon atoms, a cyano group and a halogen atom.

$R^1$ through $R^7$ independently represent an aryl group having 6 to 30 carbon atoms, a heteroaryl group having 3 to 20 carbon atoms, a heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom; or $R^1$ through $R^7$ independently represent a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms.

n represents an integer of 0 to 2.

X represents an (n+1)-valent aromatic hydrocarbon group having 6 to 17 carbon atoms, an (n+1)-valent heteroaromatic group having 3 to 20 carbon atoms or an (n+1)-valent heteroarylphenyl group having 9 to 26 carbon atoms, and these aromatic rings may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 12 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

Thus the present invention is concerned with 4-aminocarbazole compounds, as listed below.

[1] A 4-aminocarbazole compound represented by the following general formula (1):

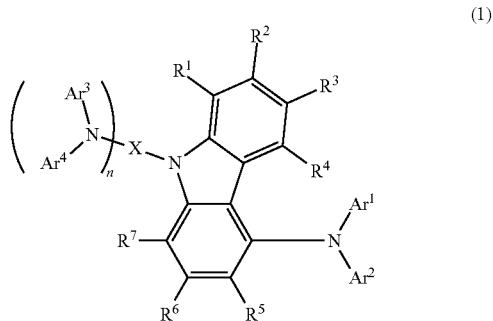

In formula (1), $Ar^1$ through $Ar^4$ independently represent an aryl group having 6 to 30 carbon atoms, a thienyl group, a pyridyl group, a benzothienyl group, a dibenzothienyl group, a dibenzofuranyl group, a 4-carbazolyl group, a dibenzothienylphenyl group, a dibenzofuranylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 11 carbon atoms, a trialkylsilyl group having 3 to 18 carbon atoms, a triarylsilyl group having 18 to 40 carbon atoms, a cyano group and a halogen atom.

$R^1$ through $R^7$ independently represent an aryl group having 6 to 30 carbon atoms, a heteroaryl group having 3 to 20 carbon atoms, a heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom; or $R^1$ through $R^7$ independently represent a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms.

n represents an integer of 0 to 2.

X represents an (n+1)-valent aromatic hydrocarbon group having 6 to 17 carbon atoms, an (n+1)-valent heteroaromatic group having 3 to 20 carbon atoms or an (n+1)-valent heteroarylphenyl group having 9 to 26 carbon atoms, and these aromatic rings may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 12 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

[2] The 4-aminocarbazole compound as mentioned above in [1], wherein $R^1$ through $R^7$ independently represent an aryl group having 6 to 30 carbon atoms, a heteroaryl group having 3 to 20 carbon atoms, a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms.

[3] The 4-aminocarbazole compound as mentioned above in [1] or [2], wherein $R^1$ through $R^7$ independently represent a phenyl group, a methylphenyl group, a methoxyphenyl group, a biphenylyl group, a dibenzothienyl group, a dibenzofuranyl group, a methyl group, a methoxy group or a hydrogen atom.

[4] The 4-aminocarbazole compound as mentioned above in any one of [1] to [3], wherein $R^1$ through $R^7$ independently represent a phenyl group, a methylphenyl group, a methoxyphenyl group or a hydrogen atom.

[5] The 4-aminocarbazole compound as mentioned above in any one of [1] to [4], wherein $R^4$, $R^5$, $R^6$ and $R^7$ represent a hydrogen atom.

[6] The 4-aminocarbazole compound as mentioned above in any one of [1] to [5], wherein $R^1$, $R^2$, $R^4$, $R^5$, $R^6$ and $R^7$ represent a hydrogen atom.

[7] The 4-aminocarbazole compound as mentioned above in any one of [1] to [6], wherein $Ar^1$ through $Ar^4$ independently represent an aryl group having 6 to 30 carbon atoms, a dibenzothienyl group, a dibenzofuranyl group, a 4-carbazolyl group, a dibenzofuranylphenyl group or a dibenzothienylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 30 carbon atoms and a heteroaryl group having 3 to 11 carbon atoms.

[8] The 4-aminocarbazole compound as mentioned above in any one of [1] to [7], wherein $Ar^1$ through $Ar^4$ independently represent a phenyl group, a biphenylyl group, a terphenylyl group, a fluorenyl group, a benzofluorenyl group, a dibenzothienyl group, a dibenzofuranyl group, a dibenzofuranylphenyl group, a dibenzothienylphenyl group or a 9-carbazoylphenyl group, and these groups may independently have at least one substituent selected from the group consisting of a methyl group, an ethyl group, a straight, branched or cyclic alkyl group having 3 to 18 carbon atoms, a methoxy group, an ethoxy group and a straight, branched or cyclic alkoxy group having 3 to 18 carbon atoms; or $Ar^1$ through $Ar^4$ independently represent a 4-carbazolyl group which may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 30 carbon atoms and a heteroaryl group having 3 to 11 carbon atoms.

[9] The 4-aminocarbazole compound as mentioned above in any one of [1] to [8], wherein $Ar^1$ through $Ar^4$ independently represent a phenyl group, a methylphenyl group, a methoxyphenyl group, a biphenylyl group, a terphenylyl group, a 9,9'-dimethylfluorenyl group, a 11,11'-dimethylbenzo[a]fluorenyl group, a dibenzothienyl group, a dibenzofuranyl group, a dibenzothienylphenyl group, a 4-(9-carbazoyl)phenyl group, a 9-phenylcarbazol-4-yl group, a 9-biphenylylcarbazol-4-yl group, a 9-quinolylcarbazol-4-yl group or a 9-dibenzothienylcarbazol-4-yl group.

[10] The 4-aminocarbazole compound as mentioned above in any one of [1] to [9], wherein X represents an aromatic group selected from the group consisting of (n+1)-valent benzene, (n+1)-valent biphenyl, (n+1)-valent naphthalene, (n+1)-valent phenanthrene, (n+1)-valent fluorene, (n+1)-valent naphthylbenzene, (n+1)-valent pyridine, (n+1)-valent pyrimidine, (n+1)-valent 1,3,5-triazine, (n+1)-valent quinoline, (n+1)-valent dibenzothiophene, (n+1)-valent dibenzofuran, (n+1)-valent pyridylbenzene, (n+1)-valent imidazolylbenzene, (n+1)-valent benzoimidazolylbenzene and (n+1)-valent benzothiazolylbenzene, and these aromatic groups may independently have at least one substituent selected from the group consisting of a methyl group, an ethyl group, a straight, branched or cyclic alkyl group having 3 to 18 carbon atoms, a methoxy group, an ethoxy group and a straight, branched or cyclic alkoxy group having 3 to 18 carbon atoms, an aryl group having 6 to 12 carbon atoms, a heteroaryl group having 3 to 20 carbon atoms, a cyano group and a halogen atom.

[11] The 4-aminocarbazole compound as mentioned above in any one of [1] to [10], wherein X represents an aromatic group selected from the group consisting of (n+1)-valent benzene, (n+1)-valent biphenyl, (n+1)-valent quinoline, (n+1)-valent dibenzothiophene, (n+1)-valent 1,3,5-triazine and (n+1)-valent pyridylbenzene, and these aromatic groups may independently have at least one substituent selected from the group consisting of a methyl group, an ethyl group, a straight, branched or cyclic alkyl group having 3 to 18 carbon atoms, a methoxy group, an ethoxy group and a straight, branched or cyclic alkoxy group having 3 to 18 carbon atoms, an aryl group having 6 to 12 carbon atoms, a cyano group and a halogen atom.

[12] The 4-aminocarbazole compound as mentioned above in any one of [1] to [11], wherein X represents (n+1)-valent benzene, (n+1)-valent biphenyl, (n+1)-valent quinoline, (n+1)-valent dibenzothiophene, (n+1)-valent 2,4-diphenyl-1,3,5-triazine or (n+1)-valent pyridylbenzene.

[13] The 4-aminocarbazole compound as mentioned above in any one of [1] to [12], wherein n represents an integer of 0 or 1.

[14] An organic electroluminescent device having at least one layer selected from the group consisting of an emitting layer, a hole transport layer and a hole injection layer, said at least one layer comprising a 4-aminocarbazole compound represented by the following general formula (1):

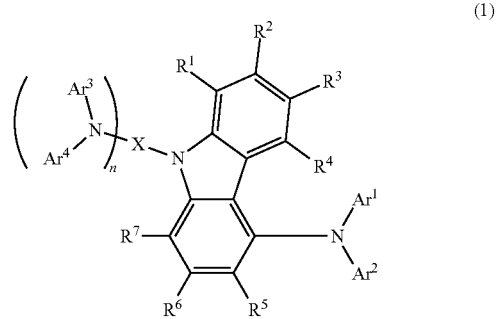

(1)

In formula (1), Ar¹ through Ar⁴ independently represent an aryl group having 6 to 30 carbon atoms, a thienyl group, a pyridyl group, a benzothienyl group, a dibenzothienyl group, a dibenzofuranyl group, a 4-carbazolyl group, a dibenzothienylphenyl group, a dibenzofuranylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 11 carbon atoms, a trialkylsilyl group having 3 to 18 carbon atoms, a triarylsilyl group having 18 to 40 carbon atoms, a cyano group and a halogen atom.

R¹ through R⁷ independently represent an aryl group having 6 to 30 carbon atoms, a heteroaryl group having 3 to 20 carbon atoms, a heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom; or R¹ through R⁷ independently represent a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms.

n represents an integer of 0 to 2.

X represents an (n+1)-valent aromatic hydrocarbon group having 6 to 17 carbon atoms, an (n+1)-valent heteroaromatic group having 3 to 20 carbon atoms or an (n+1)-valent heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 12 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

[15] A hole transport material or a hole injection material, which comprises a 4-aminocarbazole compound represented by the following general formula (1):

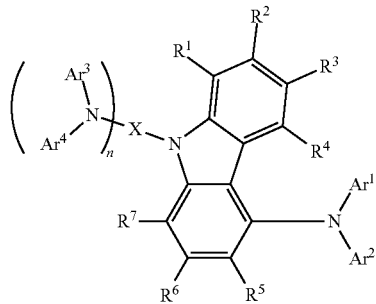

In formula (1), Ar¹ through Ar⁴ independently represent an aryl group having 6 to 30 carbon atoms, a thienyl group, a pyridyl group, a benzothienyl group, a dibenzothienyl group, a dibenzofuranyl group, a 4-carbazolyl group, a dibenzothienylphenyl group, a dibenzofuranylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 11 carbon atoms, a trialkylsilyl group having 3 to 18 carbon atoms, a triarylsilyl group having 18 to 40 carbon atoms, a cyano group and a halogen atom.

R¹ through R⁷ independently represent an aryl group having 6 to 30 carbon atoms, a heteroaryl group having 3 to 20 carbon atoms, a heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryl oxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom; or R¹ through R⁷ independently represent a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms;

n represents an integer of 0 to 2.

X represents an (n+1)-valent aromatic hydrocarbon group having 6 to 17 carbon atoms, an (n+1)-valent heteroaromatic group having 3 to 20 carbon atoms or an (n+1)-valent heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 12 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

Effects of the Invention

A phosphorescent or fluorescent organic EL device having at least one layer comprising the 4-aminocarbazole compound according to the present invention exhibits high emitting efficiency and current efficiency and reduced drive voltage as compared with an organic EL device having a layer comprising a known carbazole ring-containing compound.

Therefore the present invention can provide a phosphorescent or fluorescent organic EL device exhibiting high luminance and reduced electric power consumption.

MODE FOR PRACTICING THE INVENTION

The invention will now be described in detail.

In the following general formula (1) representing the 4-aminocarbazole compound according to the present invention,

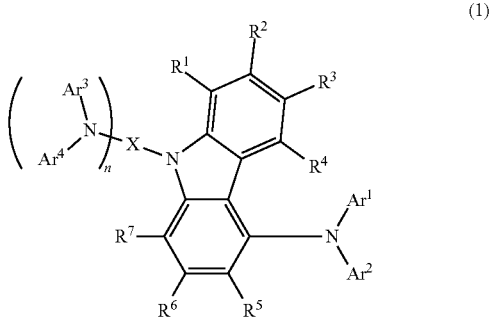

(1)

$Ar^1$ through $Ar^4$ independently represent an aryl group having 6 to 30 carbon atoms, a thienyl group, a pyridyl group, a benzothienyl group, a dibenzothienyl group, a dibenzofuranyl group, a 4-carbazolyl group, a dibenzothienylphenyl group, a dibenzofuranylphenyl group or a 9-carbazolylphenyl group.

These groups for $Ar^1$ through $Ar^4$ may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 11 carbon atoms, a trialkylsilyl group having 3 to 18 carbon atoms, a triarylsilyl group having 18 to 40 carbon atoms, a cyano group and a halogen atom.

The straight, branched or cyclic alkyl group having 3 to 18 carbon atoms for $Ar^1$ through $Ar^4$ is not particularly limited, and, as specific examples thereof, there can be mentioned propyl, isopropyl, butyl, sec-butyl, tert-butyl, pentyl, hexyl, heptyl, octyl, stearyl, cyclopropyl and cyclohexyl groups.

The straight, branched or cyclic alkoxy group having 3 to 18 carbon atoms for $Ar^1$ through $Ar^4$ is not particularly limited, and, as specific examples thereof, there can be mentioned propoxy, isopropoxy, n-butoxy, sec-butoxy, tert-butoxy, pentyloxy, hexyloxy and stearyloxy groups.

The halogenated alkyl group having 1 to 3 carbon atoms for $Ar^1$ through $Ar^4$ is not particularly limited, and the halogenated alkyl group includes, for example, trifluoromethyl, trichloromethyl and 2-fluoroethyl groups.

The halogenated alkoxy group having 1 to 3 carbon atoms for $Ar^1$ through $Ar^4$ is not particularly limited, and the halogenated alkoxy group includes, for example, trifluoromethoxy, trichloromethoxy and 2-fluoroethoxy groups.

The aryl group having 6 to 30 carbon atoms for $Ar^1$ through $Ar^4$ of formula (1) is not particularly limited, and, as specific examples thereof, there can be mentioned phenyl, 2-methylphenyl, 3-methylphenyl, 4-methylphenyl, 2-methoxyphenyl, 3-methoxyphenyl, 4-methoxyphenyl, 2-cyanophenyl, 3-cyanophenyl, 4-cyanophenyl, biphenylyl, terphenylyl, naphthyl, fuluorenyl, phenanthoryl and benzofluorenyl groups.

The aryloxy group having 6 to 18 carbon atoms for $Ar^1$ through $Ar^4$ is not particularly limited, and, as specific examples thereof, there can be mentioned phenoxy, 2-methylphenoxy, 3-methylphenoxy, 4-methylphenoxy, 2-methoxyphenoxy, 3-methoxyphenoxy, 4-methoxyphenoxy, 2-cyanophenoxy, 3-cyanophenoxy, 4-cyanophenoxy, 4-methylphenyloxy, 3-methylphenyloxy, 4-biphenylyloxy, 3-biphenylyloxy, 1-naphthyloxy and 2-naphthyloxy groups.

The heteroaryl group having 3 to 11 carbon atoms for $Ar^1$ through $Ar^4$ is an aromatic group having at least one hetero atom selected from an oxygen atom, a nitrogen atom and a sulfur atom, and, as specific examples thereof, there can be mentioned imidazolyl, pyrazolyl, thiazolyl, isothiazolyl, oxazolyl, isoxazolyl, pyridyl, 2-methylpyridyl, 3-methylpyridyl, 4-methylpyridyl, 2-methoxypyridyl, 3-methoxypyridyl, 4-methoxypyridyl, 2-cyanopyridyl, 3-cyanopyridyl, 4-cyanopyridyl, pyrimidyl, pyrazyl, 1,3,5-triazyl, benzoimidazolyl, indazolyl, benzothiazolyl, benzoisothiazolyl, 2,1,3-benzothiadiazolyl, benzooxazolyl, benzoisoxazolyl, 2,1,3-benzooxadiazolyl, quinolyl, isoquinolyl, quinoxalyl, quinazolyl, pyrolyl, furyl, thienyl, indolyl and benzothienyl groups.

The trialkylsilyl group having 3 to 18 carbon atoms for $Ar^1$ through $Ar^4$ is not particularly limited, and, the trialkylsilyl group includes, for example, trimethylsilyl, triethylsilyl and tributylsilyl groups.

The triarylsilyl group having 18 to 40 carbon atoms for $Ar^1$ through $Ar^4$ is not particularly limited, and, the triarylsilyl group includes, for example, triphenylsilyl, tri(4-methylphenyl)silyl, tri(3-methylphenyl)silyl and tri(4-biphenylyl)silyl groups.

The halogen atom for $Ar^1$ through $Ar^4$ includes, for example, fluorine, chlorine, bromine and iodine atoms.

As specific examples of $Ar^1$ through $Ar^4$, there can be mentioned phenyl, 4-methylphenyl, 3-methylphenyl, 2-methylphenyl, 4-ethylphenyl, 3-ethylphenyl, 2-ethylphenyl, 4-n-propylphenyl, 4-isopropylphenyl, 2-isopropylphenyl, 4-n-butylphenyl, 4-isobutylphenyl, 4-sec-butylphenyl, 4-tert-butylphenyl, 4-n-pentylphenyl, 4-isopentylphenyl, 4-neopentylphenyl, 4-n-hexylphenyl, 4-n-octylphenyl, 4-n-decylphenyl, 4-n-dodecylphenyl, 4-cyclopentylphenyl, 4-cyclohexylphenyl, 4-tritylphenyl, 3-tritylphenyl, 4-triphenylsilylphenyl, 3-triphenylsilylphenyl, 2,4-dimethylphenyl, 2,5-dimethylphenyl, 3,4-dimethylphenyl, 3,5-dimethylphenyl, 2,6-dimethylphenyl, 2,3,5-trimethylphenyl, 2,3,6-trimethylphenyl, 3,4,5-trimethylphenyl, 4-methoxyphenyl, 3-methoxyphenyl, 2-methoxyphenyl, 4-ethoxyphenyl, 3-ethoxyphenyl, 2-ethoxyphenyl, 4-n-propoxyphenyl, 3-n-propoxyphenyl, 4-isopropoxyphenyl, 2-isopropoxyphenyl, 4-n-butoxyphenyl, 4-isobutoxyphenyl, 2-sec-butoxyphenyl, 4-n-pentyloxyphenyl, 4-isopentyloxyphenyl, 2-isopentyloxyphenyl, 4-neopentyloxyphenyl, 2-neopentyloxyphenyl, 4-n-hexyloxyphenyl, 2-(2-ethylbutyl)oxyphenyl, 4-n-octyloxyphenyl, 4-n-decyloxyphenyl, 4-n-dodecyloxyphenyl, 4-n-tetradecyloxyphenyl, 4-cyclohexyloxyphenyl, 2-cyclohexyloxyphenyl, 4-phenoxyphenyl, 3-phenoxyphenyl, 2-methyl-4-methoxyphenyl, 2-methyl-5-methoxyphenyl, 3-methyl-4-methoxyphenyl, 3-methyl-5-methoxyphenyl, 3-ethyl-5-methoxyphenyl, 2-methoxy-4-methylphenyl, 3-methoxy-4-methylphenyl, 2,4-dimethoxyphenyl, 2,5-dimethoxyphenyl, 2,6-dimethoxyphenyl, 3,4-dimethoxyphenyl, 3,5-dimethoxyphenyl, 3,5-diethoxyphenyl, 3,5-di-n-butoxyphenyl, 2-methoxy-4-ethoxyphenyl, 2-methoxy-6-ethoxyphenyl, 3,4,5-trimethoxyphenyl, 4-cyanophenyl, 3-cyanophenyl, 4-fluorophenyl, 3-fluorophenyl, 2-fluorophenyl, 2,3-difluorophenyl, 2,4-difluorophenyl, 2,5-difluorophenyl, 2,6-difluorophenyl, 3,4-difluorophenyl, 3,5-difluorophenyl, 4-biphenylyl, 3-biphenylyl, 2-biphenylyl, 2-methyl-1,1'-biphenyl-4-yl, 3-methyl-1,1'-biphenyl-4-yl, 2'-methyl-1,1'-biphenyl-4-yl, 3'-methyl-1,1'-biphenyl-4-yl, 4'-methyl-1,1'-biphenyl-4-yl, 2,6-dimethyl-1,1'-biphenyl-4-yl, 2,2'-dimethyl-1,1'-biphenyl-4-yl, 2,3'-dimethyl-1,1'-biphenyl-4-yl, 2,4'-dimethyl-1,1'-biphenyl-4-yl, 3,2'-dimethyl-1,1'-biphenyl-4-yl, 2',3'-dimethyl-1,1'-biphenyl-4-yl, 2',4'-dimethyl-1,1'-biphenyl-4-yl, 2',5'-dimethyl-1,1'-biphenyl-4-yl, 2',6'-dimethyl-1,1'-biphenyl-4-yl, p-terphenyl, m-terphenyl, o-terphenyl, 1-naphthyl, 2-naphthyl, 2-methylnaphthalen-1-yl, 4-methylnaphthalen-1-yl, 6-methylnaphthalen-2-yl, 4-(1-naphthyl)phenyl, 4-(2-naphthyl)phenyl, 3-(1-naphthyl)phenyl, 3-(2-naphthyl)phenyl, 3-methyl-4-(1-naphthyl)phenyl, 3-methyl-4-(2-naphthyl)phenyl, 4-(2-methylnaphthalen-1-yl)phenyl, 3-(2-methylnaphthalen-1-yl)phenyl, 4-phenylnaphthalen-1-yl, 4-(2-methylphenyl)naphthalen-1-yl, 4-(3-methylphenyl)naphthalen-1-yl, 4-(4-methylphenyl)naphthalen-1-yl, 6-phenylnaphthalen-2-yl, 4-(2-methylphenyl)naphthalen-2-yl, 4-(3-methylphenyl)naphthalen-2-yl, 4-(4-methylphenyl)naphthalen-2-yl, 2-fluorenyl, 9,9-dimethyl-2-fluorenyl, 9,9-diethyl-2-fluorenyl, 9,9-di-n-propyl-2-fluorenyl, 9,9-di-n-octyl-2-fluorenyl, 9,9-diphenyl-2-fluorenyl, 9,9'-spirobifluorenyl, 9-phenanthryl, 2-phenanthryl, benzofluorenyl, 2-pyridyl, 3-methyl-2-pyridyl, 4-methyl-2-pyridyl, 5-methyl-2-pyridyl, 6-methyl-2-pyridyl, 3-pyridyl, 4-methyl-3-pyridyl, 4-pyridyl, 2,2'-bipyridin-3-yl, 2,2'-bipyridin-4-yl, 2,2'-bipyridin-5-yl, 2,3'-bipyridin-3-yl, 2,3'-bipyridin-4-yl, 2,3'-bipyridin-5-yl, 2-thienyl, 3-thienyl, 2-furanyl, 3-furanyl, 2-benzothienyl, 3-benzothienyl, 2-dibenzothienyl, 4-dibenzothienyl, 2-dibenzofuranyl, 4-dibenzofuranyl, 4-(2-pyridyl)phenyl, 4-(3-pyridyl)phenyl, 4-(4-pyridyl)phenyl, 3-(2-pyridyl)phenyl, 3-(3-pyridyl)phenyl, 3-(4-pyridyl)phenyl, 4-(2-methylbenzimidazol-1-yl)phenyl, 4-(1-methylbenzimidazol-2-yl)phenyl, 3-(2-methylbenzimidazol-1-yl)phenyl, 3-(1-methylbenzimidazol-2-yl)phenyl, 4-(2-thienyl)phenyl, 4-(2-furanyl)phenyl, 4-(2-dibenzothienyl)phenyl, 3-(2-dibenzothienyl)phenyl, 4-(4-dibenzothienyl)phenyl, 3-(4-dibenzothienyl)phenyl, 4-(2-dibenzofuranyl)phenyl, 3-(2-dibenzofuranyl)phenyl, 4-(4-dibenzofuranyl)phenyl, 3-(4-dibenzofuranyl)phenyl, 5-phenylthiophen-2-yl, 5-phenylpyridin-2-yl, 4-phenylpyridin-2-yl, 5-phenylpyridin-3-yl, 4-(9-carbazolyl)phenyl and 3-(9-carbazolyl)phenyl.

$Ar^1$ through $Ar^4$ in formula (1) are not limited to those exemplified above.

In view of high triplet level and/or good hole transporting characteristic of the 4-aminocarbazole compound of formula (1), $Ar^1$ through $Ar^4$ preferably include an aryl group having 6 to 30 carbon atoms, a dibenzothienyl group, a dibenzofuranyl group, a 4-carbazolyl group, a dibenzofuranylphenyl group, a dibenzothienylphenyl group and a 9-carbazolylphenyl group, which groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 30 carbon atoms and a heteroaryl group having 3 to 11 carbon atoms.

More preferably, $Ar^1$ through $Ar^4$ include a phenyl group, a biphenylyl group, a terphenylyl group, a fluorenyl group, a benzofluorenyl group, a dibenzothienyl group, a dibenzofuranyl group, a dibenzofuranylphenyl group, a dibenzothienylphenyl group and a 9-carbazolylphenyl group, which groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms; and $Ar^1$ through $Ar^4$ further include a 4-carbazolyl group, which may have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 30 carbon atoms and a heteroaryl group having 3 to 11 carbon atoms.

Especially preferably, $Ar^1$ through $Ar^4$ include a phenyl group, a methylphenyl group, a methoxyphenyl group, a biphenylyl group, a terphenylyl group, a 9,9'-dimethylfluorenyl group, a 11,11'-dimethylbenzo[a]fluorenyl group, a dibenzothienyl group, a dibenzofuranyl group, a dibenzothienylphenyl group, a 4-(9-carbazolyl)phenyl group, a 9-phenylcarbazol-4-yl group, a 9-biphenylylcarbazol-4-yl group, 9-quinolylcarbazol-4-yl group and a 9-dibenzothienylcarbazol-4-yl group.

In the 4-aminocarbazole compound of formula (1), $R^1$ through $R^7$ independently represent an aryl group having 6 to 30 carbon atoms, a heteroaryl group having 3 to 20 carbon atoms, a heteroarylphenyl group having 9 to 26 carbon atoms, a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms.

The above-mentioned aryl group having 6 to 30 carbon atoms, heteroaryl group having 3 to 20 carbon atoms and heteroarylphenyl group having 9 to 26 carbon atoms may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

The aryl group having 6 to 30 carbon atoms for $R^1$ through $R^7$ is not particularly limited, and, the aryl group includes, for example, those which are listed as examples of the aryl group having 6 to 30 carbon atoms for the above-mentioned $Ar^1$ through $Ar^4$.

The heteroaryl group having 9 to 26 carbon atoms for $R^1$ through $R^7$ is not particularly limited and the heteroaryl group includes an aromatic group having at least one hetero atom selected from an oxygen atom, a nitrogen atom and a sulfur atom. As specific examples of the heteroaryl group, there can be mentioned imidazolyl, pyrazolyl, thiazolyl, isothiazolyl, oxazolyl, isoxazolyl, pyridyl, 2-methylpyridyl, 3-methylpyridyl, 4-methylpyridyl, 2-methoxypyridyl, 3-methoxypyridyl, 4-methoxypyridyl, 2-cyanopyridyl, 3-cyanopyridyl, 4-cyanopyridyl, pyrimidyl, pyrazyl, 1,3,5-triazyl, benzoimidazolyl, indazolyl, benzothiazolyl, benzoisothiazolyl, 2,1,3-benzothiadiazolyl, benzooxazolyl, benzoisoxazolyl, 2,1,3-benzooxadiazolyl, quinolyl, isoquinolyl, quinoxalyl, quinazolyl, acrydinyl, 1,10-phenanthronyl, pyrolyl, furyl, thienyl, indolyl, benzothienyl, 4-carbazolyl, 9-carbazolyl, dibenzothienyl and dibenzofuranyl groups.

The heteroarylphenyl group having 9 to 26 carbon atoms for $R^1$ through $R^7$ is not particularly limited and the heteroarylphenyl group includes, for example, pyridylphenyl, imidazolylphenyl, benzoimidazolylphenyl, benzothiazolylphenyl, triazylphenyl, pyrolylphenyl, furanylphenyl, dibenzofuranylphenyl and dibenzothienylphenyl groups.

The straight, branched or cyclic alkyl group having 3 to 18 carbon atoms for $R^1$ through $R^7$ is not particularly limited, and, the alkyl group includes, for example, those which are listed as examples of the straight, branched or cyclic alkyl group having 3 to 18 carbon atoms for the above-mentioned $Ar^1$ through $Ar^4$.

The straight, branched or cyclic alkoxy group having 3 to 18 carbon atoms for $R^1$ through $R^7$ is not particularly limited, and, the alkoxy group includes, for example, those which are listed as examples of the straight, branched or cyclic alkoxy group having 3 to 18 carbon atoms for the above-mentioned $Ar^1$ through $Ar^4$.

The halogenated alkyl group having 1 to 3 carbon atoms for $R^1$ through $R^7$ is not particularly limited, and, the halogenated alkyl group includes, for example, those which are listed as examples of the halogenated alkyl group having 1 to 3 carbon atoms for the above-mentioned $Ar^1$ through $Ar^4$.

The halogenated alkoxy group having 1 to 3 carbon atoms for $R^1$ through $R^7$ is not particularly limited, and, the halogenated alkoxy group includes, for example, those which are listed as examples of the halogenated alkoxy group having 1 to 3 carbon atoms for the above-mentioned $Ar^1$ through $Ar^4$.

The aryloxy group having 6 to 18 carbon atoms for $R^1$ through $R^7$ is not particularly limited, and, the aryloxy group includes, for example, those which are listed as examples of the aryloxy group having 6 to 18 carbon atoms for the above-mentioned $Ar^1$ through $Ar^4$.

The trialkylsilyl group having 3 to 18 carbon atoms for $R^1$ through $R^7$ is not particularly limited, and, the trialkylsilyl group includes, for example, those which are listed as examples of the trialkylsilyl group having 3 to 18 carbon atoms for the above-mentioned $Ar^1$ through $Ar^4$.

The triarylsilyl group having 18 to 40 carbon atoms for $R^1$ through $R^7$ is not particularly limited, and, the triarylsilyl group includes, for example, those which are listed as examples of the triarylsilyl group having 18 to 40 carbon atoms for the above-mentioned $Ar^1$ through $Ar^4$.

The halogen atom for $R^1$ through $R^7$ is not particularly limited, and the halogen atom includes, for example, those which are listed as examples of the halogen atom for the above-mentioned $Ar^1$ through $Ar^4$.

In view of high triplet level and/or good hole transporting characteristic of the 4-aminocarbazole compound of formula (1), $R^1$ through $R^7$ preferably independently represent an aryl group having 6 to 30 carbon atoms, a heteroaryl group having 3 to 20 carbon atoms, a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atom.

In view of commercial availability of a raw material, $R^1$ through $R^7$ more preferably independently represent a phenyl group, a methylphenyl group, a methoxyphenyl group, a biphenylyl group, a dibenzothienyl group, a dibenzofuranyl group, a methyl group, a methoxy group or a hydrogen atom. Especially preferably, $R^1$ through $R^7$ independently represent a phenyl group, a methylphenyl group, a methoxyphenyl group or a hydrogen atom.

In view of the industrial production process, $R^4$, $R^5$, $R^6$ and $R^7$ are especially preferably hydrogen atoms. Most preferably, $R^1$, $R^2$, $R^4$, $R^5$, $R^6$ and $R^7$ are hydrogen atoms.

In the 4-aminocarbazole compound of formula (1), n represents an integer of 0 to 2. In view of high triplet level and good hole transporting characteristic, n is preferably 0 or 1, and more preferably n is 0.

In the 4-aminocarbazole compound of formula (1), X represents an (n+1)-valent aromatic hydrocarbon group having 6 to 17 carbon atoms, an (n+1)-valent heteroaromatic group having 3 to 20 carbon atoms or an (n+1)-valent heteroarylphenyl group having 9 to 26 carbon atoms.

The above-mentioned aromatic hydrocarbon group, heteroaromatic group and heteroarylphenyl group may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 12 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

The (n+1)-valent aromatic hydrocarbon group having 6 to 17 carbon atoms for X is not particularly limited, and, as specific examples thereof, there can be mentioned phenyl, phenylene, benzenetriyl, 2-methylphenyl, 3-methylphenyl, 4-methylphenyl, methylbenzenediyl, methylbenzenetriyl, 2-methoxyphenyl, 3-methoxyphenyl, 4-methoxyphenyl, methoxybenzenediyl, methoxybenzenetriyl, 2-cyanophenyl, 3-cyanophenyl, cyanobenzenediyl, cyanobenzenetriyl, biphenylyl, biphenylene, biphenyltriyl, naphthyl, naphthylene, naphthalenetriyl, fluorenyl, fluorenediyl, fluorenetriyl, benzofluorenyl, benzofluorenediyl, benzofluorenetriyl, phenanthryl, phenanthrenediyl and phenanthrenetriyl groups.

The (n+1)-valent heteroaromatic group having 3 to 20 carbon atoms for X is not particularly limited, and includes a (n+1)-valent heteroaromatic group containing at least one hetero atom selected from an oxygen atom, a nitrogen atom and a sulfur atom. As specific examples of the (n+1)-valent heteroaromatic group, there can be mentioned imidazolyl, imidazolediyl, imidazoletriyl, pyrazolyl, pyrazolediyl, pyrazoletriyl, thiazolyl, thiazolediyl, thiazoletriyl, isothiazolyl, isothiazolediyl, isothiazoletriyl, oxazolyl, oxazolediyl, oxazoletriyl, isoxazolyl, isoxazolediyl, isoxazoletriyl, pyridyl, pyridinediyl, pyridinetriyl, 2-methylpyridyl, 3-methylpyridyl, 4-methylpyridyl, methylpyridinediyl, methylpyridinetriyl, 2-methoxypyridyl, 3-methoxylpyridyl, 4-methoxypyridyl, methoxypyridinediyl, methoxylpyridinetriyl, 2-cyanopyridyl, 3-cyanopyridyl, 4-cyanopyridyl, cyanopyridinediyl, cyanopyridinetriyl, pyrimidyl, pyrimidinediyl, pyrimidinetriyl, pyrazyl, pyrazinediyl, pyrazinetriyl, 1,3,5-triazyl, 1,3,5-triazinediyl, 1,3,5-triazinetriyl, benzimidazolyl, benzimidazolediyl, benzimidazoletriyl, indazolyl, indazolediyl, indazoletriyl, benzthiazolyl, benzthiazolediyl, benzthiazoletriyl, benzisothiazolyl, benzisothiazolediyl, benzisothiazoletriyl, 2,1,3-benzthiadiazolyl, 2,1,3-benzthiadiazolediyl, 2,1,3-benzthiadiazoletriyl, benzoxazolyl, benzoxazolediyl, benzoxazoletriyl, benzisoxazolyl, benzisoxazolediyl, benzisoxazoletriyl, 2,1,3-benzoxadiazolyl, 2,1,3-benzoxadiazolediyl, 2,1,3-benzoxadiazoletriyl, quinolyl, quinolinediyl, quinolinetriyl, isoquinolyl, isoquinolinediyl, isoquinolinetriyl, quinoxalyl, quinoxalinediyl, quinoxalinetriyl, quinazolyl, quinazolinediyl, quinazolinetriyl, acrydinyl, acrydinediyl, acrydinetriyl, 1,10-phenathrolyl, 1,10-phenathrolinediyl, 1,10-phenathrolinetriyl, pyrrolyl, pyrrolediyl, pyrroletriyl, furyl, furandiyl, furantriyl, thienyl, thiophenediyl, thiophenetriyl, indolyl, indolediyl, indoletriyl, benzothienyl, benzothiophenediyl, benzothiophenetriyl, 4-carbazolyl, carbazolediyl, carbazoletriyl, dibenzothienyl, dibenzothiophenediyl, dibenzothiophenetriyl, dibenzofuranyl, dibenzofurandiyl and dibenzofurantriyl groups.

The (n+1)-valent heteroarylphenyl group having 9 to 26 carbon atoms for X is not particularly limited, and, as specific examples thereof, there can be mentioned pyridylphenylyl, pyridylphenyldiyl, pyridylphenyltriyl, imidazolylphenylyl, imidazolylphenyldiyl, imidazolylphenyltriyl, benzimidazolylphenylyl, benzimidazolylphenyldiyl, benzimidazolylphenyltriyl, benzthiazolylphenylyl, benzthiazolylphenyldiyl, benzthiazolylphenyltriyl, triazylphenyl, triazylphenyldiyl, triazylphenyltriyl, pyrrolylphenyl, pyrrolylphenyldiyl, pyrrolylphenyltriyl, furanylphenyl, furanylphenyldiyl, furanylphenyltriyl, dibenzofuranylphenyl, dibenzofuranylphenyldiyl, dibenzofuranylphenyltriyl, dibenzothienylphenyl, dibenzothienylphenyldiyl and dibenzothienylphenyltriyl groups.

The straight, branched or cyclic alkyl group having 3 to 18 carbon atoms, which X may have as a substituent, is not particularly limited. The alkyl group includes, for example, those which are listed as examples of the straight, branched or cyclic alkyl group having 3 to 18 carbon atoms for the above-mentioned $Ar^1$ through $Ar^4$.

The straight, branched or cyclic alkoxy group having 3 to 18 carbon atoms, which X may have as a substituent, is not particularly limited. The alkoxy group includes, for example, those which are listed as examples of the straight, branched or cyclic alkoxy group having 3 to 18 carbon atoms for the above-mentioned $Ar^1$ through $Ar^4$.

The halogenated alkyl group having 1 to 3 carbon atoms, which X may have as a substituent, is not particularly limited. The halogenated alkyl group includes, for example, those which are listed as examples of the halogenated alkyl group having 1 to 3 carbon atoms for the above-mentioned $Ar^1$ through $Ar^4$.

The halogenated alkoxy group having 1 to 3 carbon atoms, which X may have as a substituent, is not particularly limited. The halogenated alkoxy group includes, for example, those which are listed as examples of the halogenated alkoxy group having 1 to 3 carbon atoms for the above-mentioned $Ar^1$ through $Ar^4$.

The aryl group having 6 to 12 carbon atoms, which X may have as a substituent, is not particularly limited. The aryl group includes, for example, phenyl, 2-methylphenyl, 3-methylphenyl, 4-methylphenyl, 2-methoxyphenyl, 3-methoxyphenyl, 4-methoxyphenyl, 2-cyanophenyl, 3-cyanophenyl, biphenylyl and naphthyl groups.

The aryloxy group having 6 to 18 carbon atoms, which X may have as a substituent, is not particularly limited. The aryloxy group includes, for example, those which are listed as examples of the aryloxy group having 6 to 18 carbon atoms for the above-mentioned $Ar^1$ through $Ar^4$.

The heteroaryl group having 3 to 20 carbon atoms, which X may have as a substituent, is not particularly limited. The heteroaryl group includes, for example, those which are listed as examples of the heteroaryl group having 3 to 20 carbon atoms for the above-mentioned $Ar^1$ through $Ar^4$.

The trialkylsilyl group having 3 to 18 carbon atoms, which X may have as a substituent, is not particularly limited. The trialkylsilyl group includes, for example, those which are listed as examples of the trialkylsilyl group having 3 to 18 carbon atoms for the above-mentioned $Ar^1$ through $Ar^4$.

The triarylsilyl group having 18 to 40 carbon atoms, which X may have as a substituent, is not particularly limited. The triarylsilyl group includes, for example, those which are listed as examples of the triarylsilyl group having 18 to 40 carbon atoms for the above-mentioned $Ar^1$ through $Ar^4$.

As specific examples of X, there can be mentioned phenyl, 4-methylphenyl, 3-methylphenyl, 2-methylphenyl, 4-ethylphenyl, 3-ethylphenyl, 2-ethylphenyl, 4-n-propylphenyl, 4-isopropylphenyl, 2-isopropylphenyl, 4-n-butylphenyl, 4-isobutylphenyl, 4-sec-butylphenyl, 4-tert-butylphenyl, 4-n-pentylphenyl, 4-isopentylphenyl, 4-neopentylphenyl, 4-n-hexylphenyl, 4-n-octylphenyl, 4-n-decylphenyl, 4-n-dodecylphenyl, 4-cyclopentylphenyl, 4-cyclohexylphenyl, 4-tritylphenyl, 3-tritylphenyl, 4-triphenylsilylphenyl, 3-triphenylsilylphenyl, 2,4-dimethylphenyl, 2,5-dimethylphenyl, 3,4-dimethylphenyl, 3,5-dimethylphenyl, 2,6-dimethylphenyl, 2,3,5-trimethylphenyl, 2,3,6-trimethylphenyl, 3,4,5-trimethylphenyl, 4-methoxyphenyl, 3-methoxyphenyl, 2-methoxyphenyl, 4-ethoxyphenyl, 3-ethoxyphenyl, 2-ethoxyphenyl, 4-n-propoxyphenyl, 3-n-propoxyphenyl, 4-isopropoxyphenyl, 2-isopropoxyphenyl, 4-n-butoxyphenyl, 4-isobutoxyphenyl, 2-sec-butoxyphenyl, 4-n-pentyloxyphenyl, 4-isopentyloxyphenyl, 2-isopentyloxyphenyl, 4-neopentyloxyphenyl, 2-neopentyloxyphenyl, 4-n-hexyloxyphenyl, 2-(2-ethylbutyl)oxyphenyl, 4-n-octyloxyphenyl, 4-n-decyloxyphenyl, 4-n-dodecyloxyphenyl, 4-n-tetradecyloxyphenyl, 4-cyclohexyloxyphenyl, 2-cyclohexyloxyphenyl, 4-phenoxyphenyl, 3-phenoxyphenyl, 2-methyl-4-methoxyphenyl, 2-methyl-5-methoxyphenyl, 3-methyl-4-methoxyphenyl, 3-methyl-5-methoxyphenyl, 3-ethyl-5-methoxyphenyl, 2-methoxy-4-methylphenyl, 3-methoxy-4-methylphenyl, 2,4-dimethoxyphenyl, 2,5-dimethoxyphenyl, 2,6-dimethoxyphenyl, 3,4-dimethoxyphenyl, 3,5-dimethoxyphenyl, 3,5-diethoxyphenyl, 3,5-di-n-butoxyphenyl, 2-methoxy-4-ethoxyphenyl, 2-methoxy-6-ethoxyphenyl, 3,4,5-trimethoxyphenyl, 4-cyanophenyl, 3-cyanophenyl, 4-fluorophenyl, 3-fluorophenyl, 2-fluorophenyl, 2,3-difluorophenyl, 2,4-difluorophenyl, 2,5-difluorophenyl, 2,6-difluorophenyl, 3,4-difluorophenyl, 3,5-difluorophenyl, 4-biphenylyl, 3-biphenylyl, 2-biphenylyl, 2-methyl-1,1'-biphenyl-4-yl, 3-methyl-1,1'-biphenyl-4-yl, 2'-methyl-1,1'-biphenyl-4-yl, 3'-methyl-1,1'-biphenyl-4-yl, 4'-methyl-1,1'-biphenyl-4-yl, 2,6-dimethyl-1,1'-biphenyl-4-yl, 2,2'-dimethyl-1,1'-biphenyl-4-yl, 2,3'-dimethyl-1,1'-biphenyl-4-yl, 2,4'-dimethyl-1,1'-biphenyl-4-yl, 3,2'-dimethyl-1,1'-biphenyl-4-yl, 2',3'-dimethyl-1,1'-biphenyl-4-yl, 2',4'-dimethyl-1,1'-biphenyl-4-yl, 2',5'-dimethyl-1,1'-biphenyl-4-yl, 2',6'-dimethyl-1,1'-biphenyl-4-yl, 1-naphthyl, 2-naphthyl, 2-methylnaphthalene-1-yl, 4-methylnaphthalene-1-yl, 6-methylnaphthalene-2-yl, 4-(1-naphthyl)phenyl, 4-(2-naphthyl)phenyl, 3-(1-naphthyl)phenyl, 3-(2-naphthyl)phenyl, 3-methyl-4-(1-naphthyl)phenyl, 3-methyl-4-(2-naphthyl)phenyl, 4-(2-methylnaphthan-1-yl)phenyl, 3-(2-methylnaphthan-1-yl)phenyl, 4-phenylnaphthalen-1-yl, 4-(2-methylphenyl)naphthalen-1-yl, 4-(3-methylphenyl)naphthalen-1-yl, 4-(4-methylphenyl)naphthalen-1-yl, 6-phenylnaphthalen-2-yl, 4-(2-methylphenyl)naphthalen-2-yl, 4-(3-methylphenyl)naphthalen-2-yl, 4-(4-methylphenyl)naphthalen-2-yl, 2-fluorenyl, 9,9-dimethyl-2-fluorenyl, 9,9-diethyl-2-fluorenyl, 9,9-di-n-propyl-2-fluorenyl, 9,9-di-n-octyl-2-fluorenyl, 9,9-diphenyl-2-fluorenyl, 9-phenanthryl, 2-phenanthryl, benzofluorenyl, 1-imidazolyl, 2-phenyl-1-imidazolyl, 2-phenyl-3,4-dimethyl-1-imidazolyl, 2,3,4-triphenyl-1-imidazolyl, 2-(2-naphthyl)-3,4-diphenyl-1-imidazolyl, 2-(2-naphthyl)-3,4-diphenyl-1-imidazolyl, 1-methyl-2-imidazolyl, 1-ethyl-2-imidazolyl, 1-phenyl-2-imidazolyl, 1-methyl-4-phenyl-2-imidazolyl, 1,4,5-trimethyl-2-imidazolyl, 1-methyl-4,5-diphenyl-2-imidazolyl, 1-phenyl-4,5-dimethyl-2-imidazolyl, 1,4,5-triphenyl-2-imidazolyl, 1-phenyl-4,5-dibiphenylyl-2-imidazolyl, 1-methyl-3-pyrazolyl, 1-phenyl-3-pyrazolyl, 1-methyl-4-pyrazolyl, 1-phenyl-4-pyrazolyl, 1-methyl-5-pyrazolyl, 1-phenyl-5-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-pyridyl, 3-methyl-2-pyridyl, 4-methyl-2-pyridyl, 5-methyl-2-pyridyl, 6-methyl-2-pyridyl, 3-pyridyl, 4-methyl-3-pyridyl, 4-pyridyl, 2-pyrimidyl, 2,2'-bipyridin-3-yl, 2,2'-bipyridin-4-yl, 2,2'-bipyridin-5-yl, 2,3'-bipyridin-3-yl, 2,3'-bipyridin-4-yl, 2,3'-bipyridin-5-yl, 5-pyrimidyl, pyrazinyl, 1,3,5-triazyl, 4,6-diphenyl-1,3,5-triazin-2-yl, 1-benzimidazolyl, 2-methyl-1-benzimidazolyl, 2-phenyl-1-benzimidazolyl, 1-methyl-2-benzimidazolyl, 1-phenyl-2-benzimidazolyl, 1-methyl-5-benzimidazolyl, 1,2-dimethyl-5-benzimidazolyl, 1-methyl-2-phenyl-5-benzimidazolyl, 1-phenyl-5-benzimidazolyl, 1,2-diphenyl-5-benzimidazolyl, 1-methyl-6-benzimidazolyl, 1,2-dimethyl-6-benzimidazolyl, 1-methyl-2-phenyl-6-benzimidazolyl, 1-phenyl-6-benzimidazolyl, 1,2-diphenyl-6-benzimidazolyl, 1-methyl-3-indazolyl, 1-phenyl-3-indazolyl, 2-benzothiazolyl, 4-benzothiazolyl, 5-benzothiazolyl, 6-benzothiazolyl, 7-benzothiazolyl, 3-benzoisothiazolyl, 4-benzoisothiazolyl, 5-benzoisothiazolyl, 6-benzoisothiazolyl, 7-benzoisothiazolyl, 2,1,3-benzothiadiazol-4-yl, 2,1,3-benzothiadiazol-5-yl, 2-benzoxazolyl, 4-benzoxazolyl, 5-benzoxazolyl, 6-benzoxazolyl, 7-benzoxazolyl, 3-benzoisoxazolyl, 4-benzoisoxazolyl, 5-benzoisoxazolyl, 6-benzoisoxazolyl, 7-benzoisoxazolyl, 2,1,3-benzoxadiazolyl-4-yl, 2,1,3-benzoxadiazolyl-5-yl, 2-quinolyl, 3-quinolyl, 5-quinolyl, 6-quinolyl, 1-isoquinolyl, 4-isoquinolyl, 5-isoquinolyl, 2-quinoxalyl, 3-phenyl-2-quinoxalyl, 6-quinoxalyl, 2,3-dimethyl-6-quinoxalyl, 2,3-diphenyl-6-quinoxalyl, 2-quinazolyl, 4-quinazolyl, 2-acrydinyl, 9-acrydinyl, 1,10-phenanthrolin-3-yl, 1,10-phenanthrolin-5-yl, 2-thienyl, 3-thienyl, 2-furanyl, 3-furanyl, 1-methylindol-2-yl, 1-phenylindol-2-yl, 2-benzothienyl, 2-dibenzothienyl, 4-dibenzothienyl, 2-dibenzofuranyl, 4-dibenzofuranyl, 4-(2-pyridyl)phenyl, 4-(3-pyridyl)phenyl, 4-(4-pyridyl)phenyl, 3-(2-pyridyl)phenyl, 3-(3-pyridyl)phenyl, 3-(4-pyridyl)phenyl, 4-(2-phenylimidazol-1-yl)phenyl, 4-(1-phenylimidazol-2-yl)phenyl, 4-(2,3,4-triphenylimidazol-1-yl)phenyl, 4-(1-methyl-4,5-diphenylimidazol-2-yl)phenyl, 4-(2-methylbenzimidazol-1-yl)phenyl, 4-(2-phenylbenzimidazol-1-yl)phenyl, 4-(1-methylbenzimidazol-2-yl)phenyl, 3-(2-methylbenzimidazol-1-yl)phenyl, 3-(2-phenylbenzimidazol-1-yl)phenyl, 3-(1-methylbenzimidazol-2-yl)phenyl, 3-(2-phenylbenzimidazol-1-yl)phenyl, 4-(3,5-diphenyltriazin-1-yl)phenyl, 4-(2-thienyl)phenyl, 4-(2-furanyl)phenyl, 5-phenylthiophen-2-yl, 5-phenylpyridin-2-yl, 4-phenylpyridin-2-yl, 5-phenylpyridin-3-yl, 4-(9-carbazolyl)phenyl and 3-(9-carbazolyl)phenyl.

Specific examples of X further includes divalent counterpart aromatic groups and trivalent counterpart aromatic compounds of the above-listed univalent aromatic groups.

X is not limited to these univalent, divalent and trivalent aromatic groups.

In view of good characteristics of organic EL devices made from the 4-aminocarbazole compound of formula (1), X is preferably selected from (n+1)-valent benzene, (n+1)-valent biphenyl, (n+1)-valent natphthalene, (n+1)-valent phenthrene, (n+1)-valent fluorene, (n+1)-valent naphthylbenzene, (n+1)-valent pyridine, (n+1)-valent pyrimidine, (n+1)-valent 1,3,5-trizine, (n+1)-valent quinoline, (n+1)-valent dibenzothiophene, (n+1)-valent dibenzofurane, (n+1)-valent pyridylbenzene, (n+1)-valent imidazolylbenzene, (n+1)-valent benzimidazolylbenzene and (n+1)-valent benzthiazolylbenzene. These preferable aromatic rings may have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 12 carbon atoms, a heteroaryl group having 3 to 20 carbon atoms, a cyano group and a halogen atom.

X is more preferably selected from (n+1)-valent benzene, (n+1)-valent biphenyl, (n+1)-valent quinoline, (n+1)-valent dibenzothiophene, 2,4-diphenyl-1,3,5-trizine and (n+1)-valent pyridylphenylbenzene. X is especially preferably selected from a phenyl group, a quinolyl group, a dibenzothienyl group, a 2,4-diphenyl-1,3,5-trizinyl group and a pyridylphenyl group.

As described in the background art, in order to attain a high emitting efficiency in the organic EL device using a phosphorescent emitting material, it is required to use a hole transport material having a triplet level higher than a triplet level of the emitting material.

Thus, in the case when an organic EL device is made by using a hole transport material in combination with, for example, tris(2-phenylpyridine)iridium (hereinafter abbreviated to as "Ir(ppy)$_3$" when appropriate), which is typical phosphorescent material emitting green light and has a triplet of 2.42 eV (see non-patent document 1), it is required that the hole transport material used should have a triplet higher than 2.42 eV. Therefore, the triplet level of the 4-aminocarbazole compound of formula (1) is not particularly limited, but is preferably at least 2.43 eV, more preferably at least 2.50 eV.

Thus, in the case when an organic EL device is made by using a hole transport material in combination with, for example, bis[2-(4,6-difluorophenyl)pyridinato-N,C']iridium (III)-picolinate (hereinafter abbreviated to as "Flrpic" when appropriate), which is typical phosphorescent material emitting blue light and has a triplet of 2.65 eV (see Applied Physics Letters, 2003, vol. 82, p 2422), it is required that the hole transport material used should have a triplet higher than 2.65 eV. Therefore, the triplet level of the 4-aminocarbazole compound of formula (1) is not particularly limited, but is preferably at least 2.66 eV, more preferably at least 2.70 eV.

Preferable specific examples of the 4-aminocarbazole compound of formula (1) are listed in the following chemical formulae, but the 4-aminocarbazole compound should not be construed to be limited thereto.

(A1)
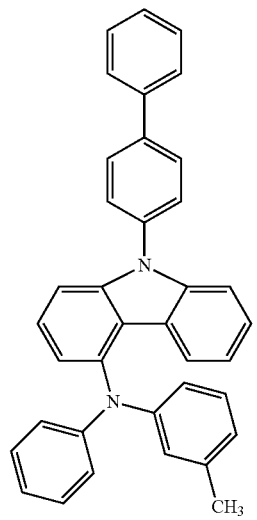
(A2)
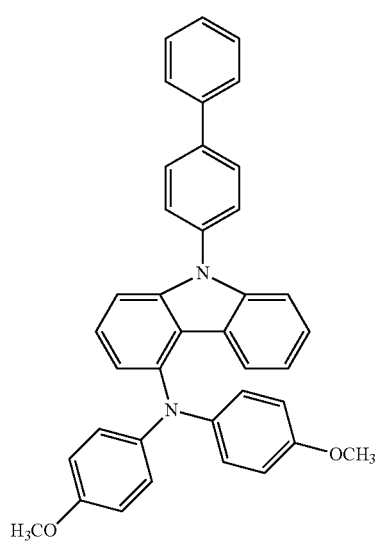
(A3)
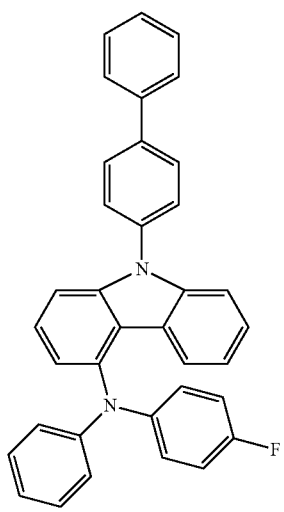
(A4)
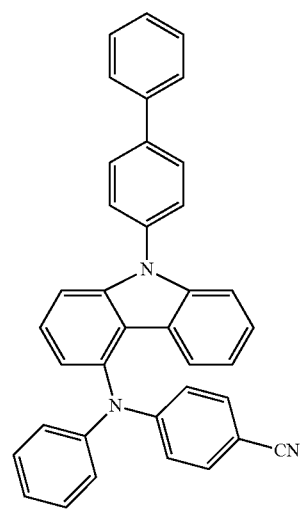
(A5)
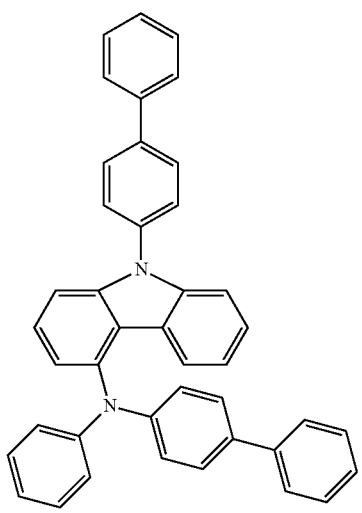
(A6)
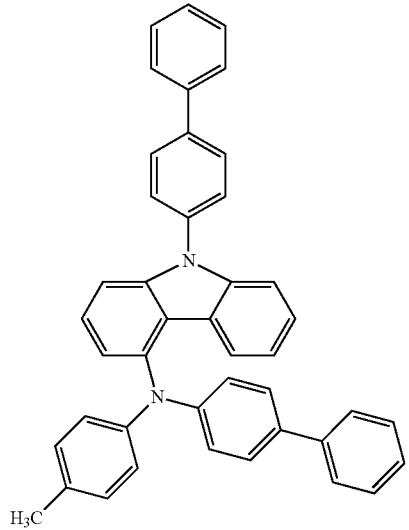

(A7)
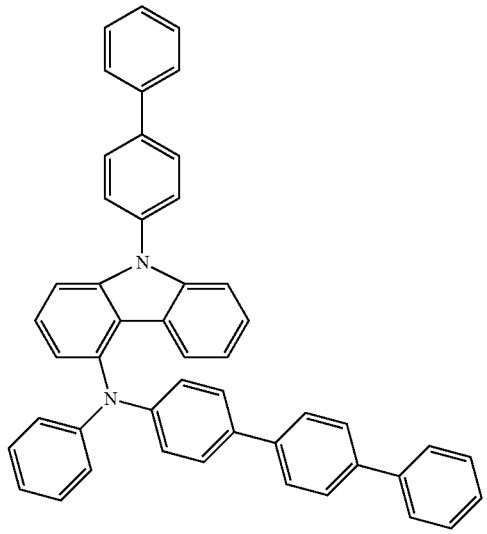
(A9)
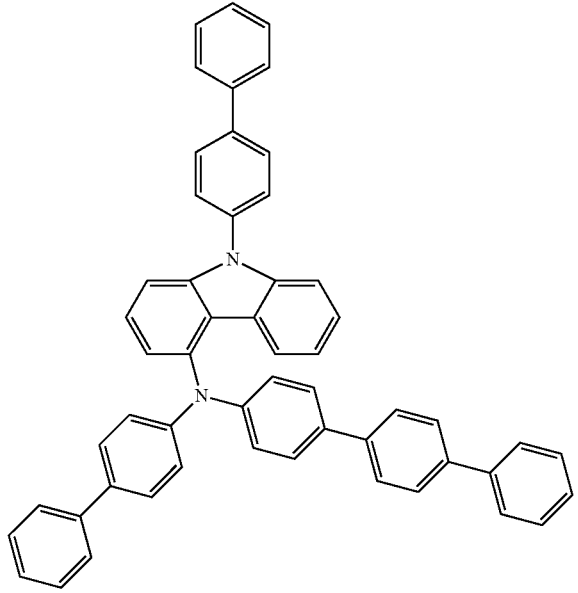
(A8)
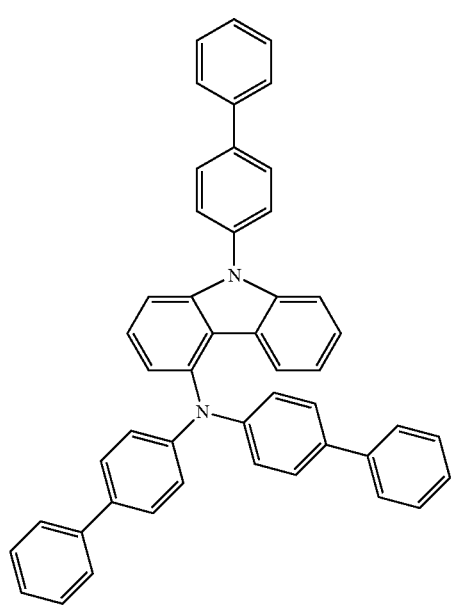
(A10)
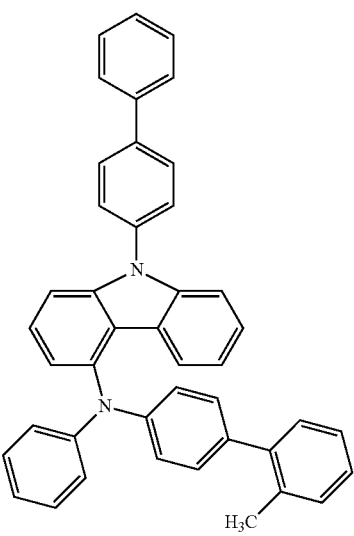

(A11)
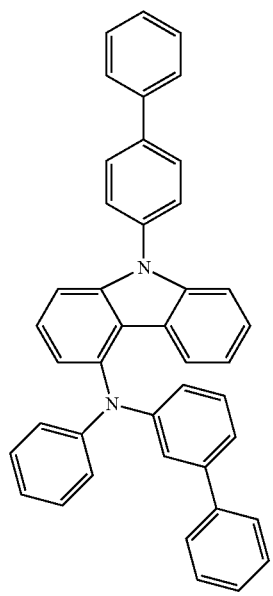
(A13)
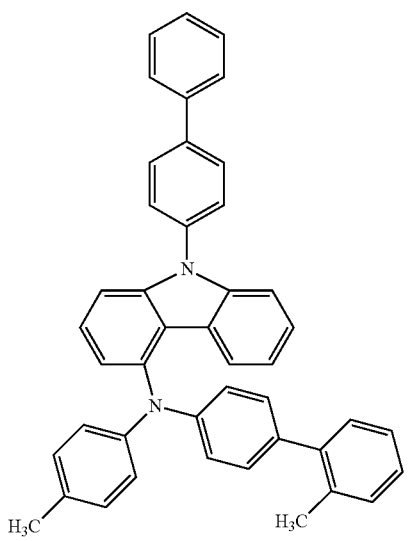
(A12)
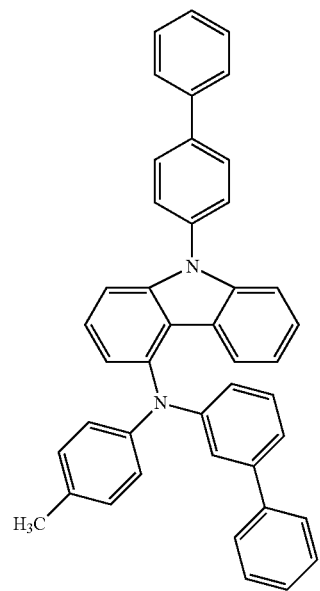
(A14)
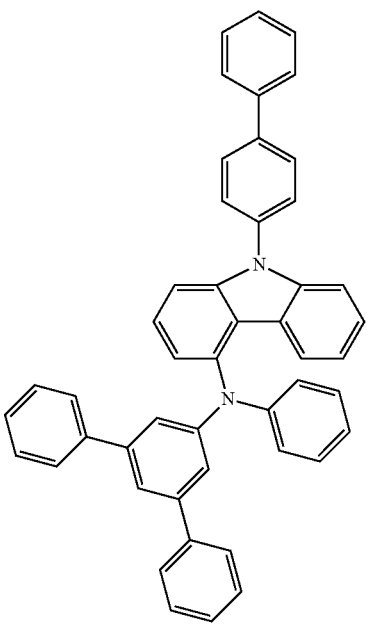

(A15)
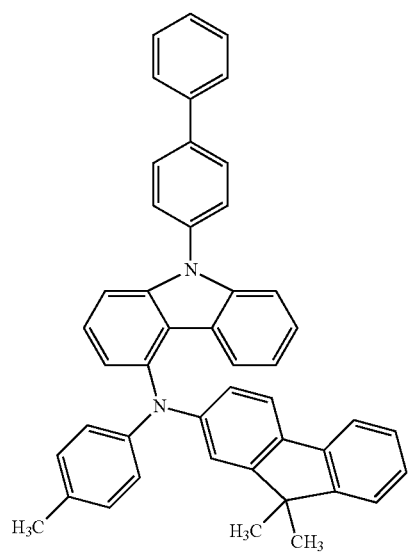
(A16)
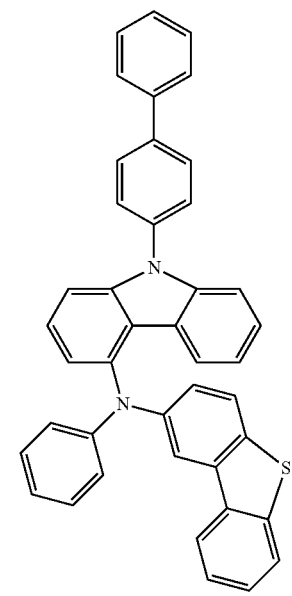
(A17)
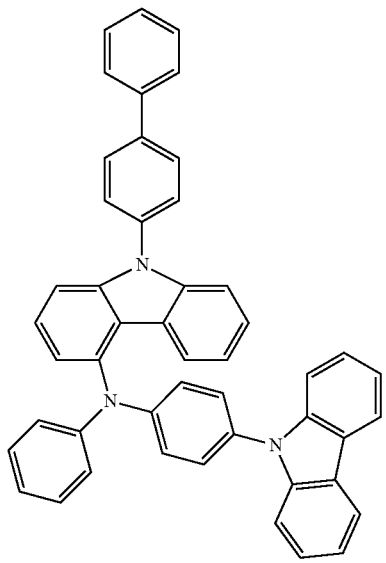
(A18)
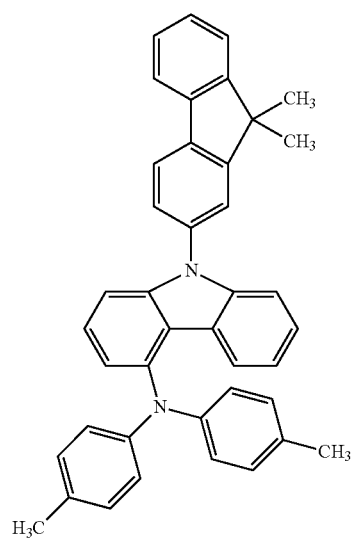
(A19)
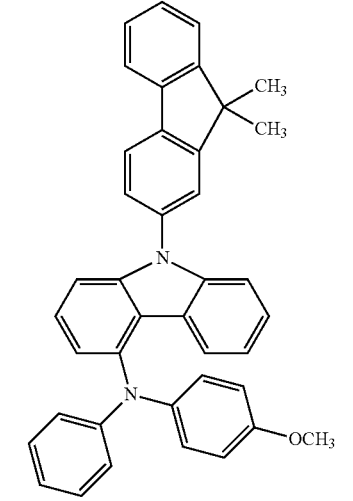

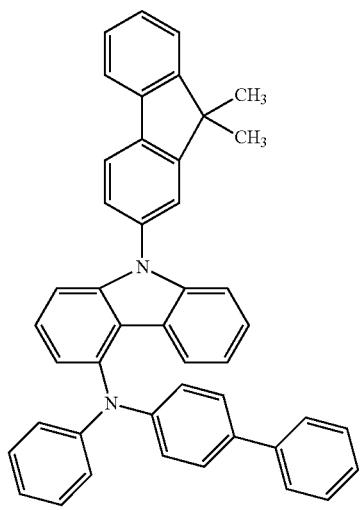
(A20)
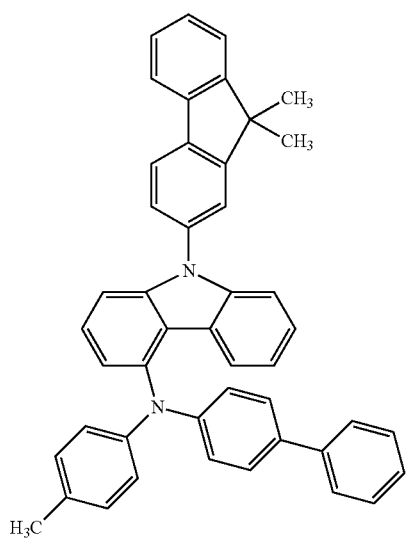
(A21)
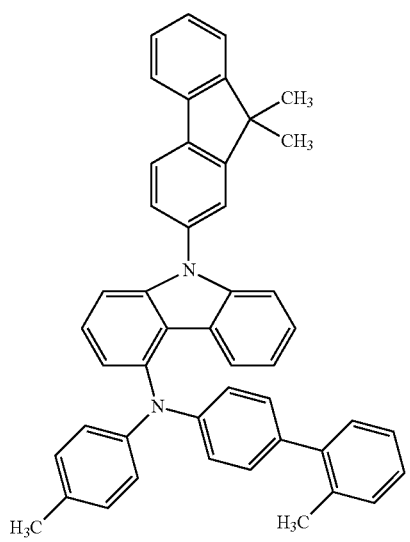
(A22)
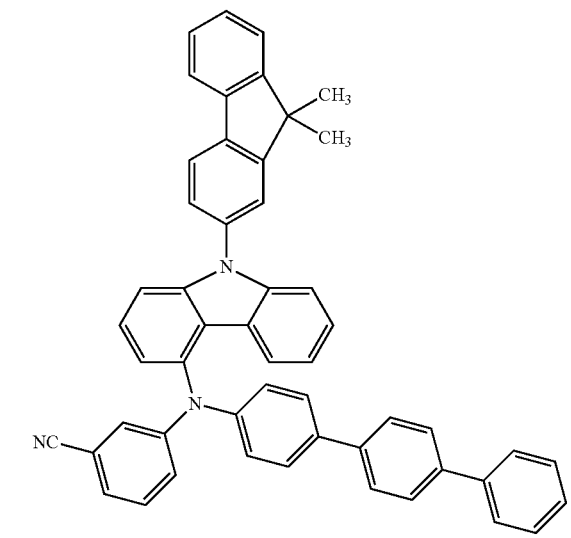
(A23)
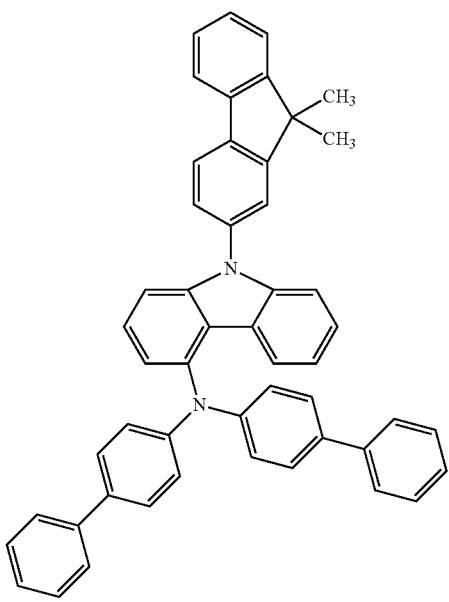
(A24)

(A25)
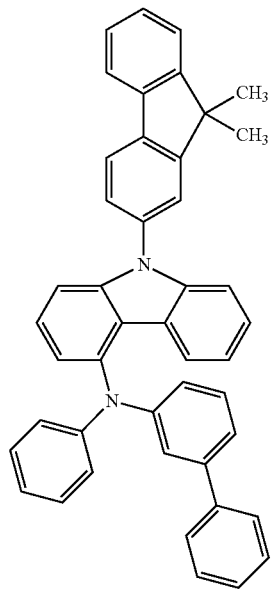
(A26)
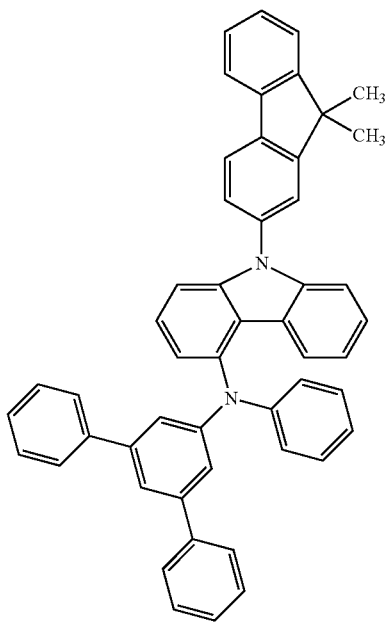
(A27)
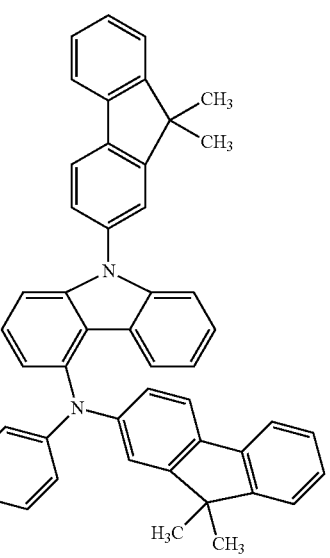
(A28)
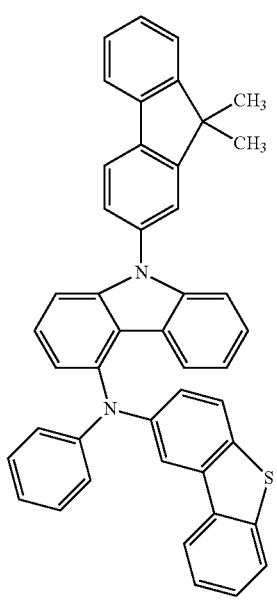

(A29)
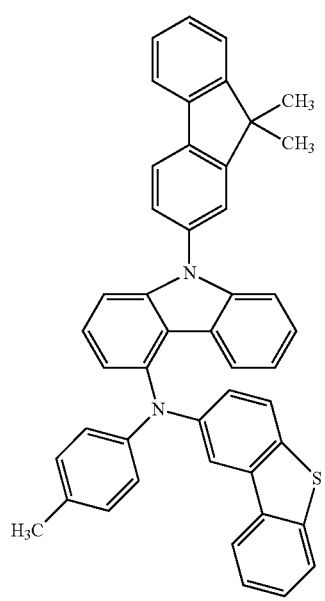
(A31)
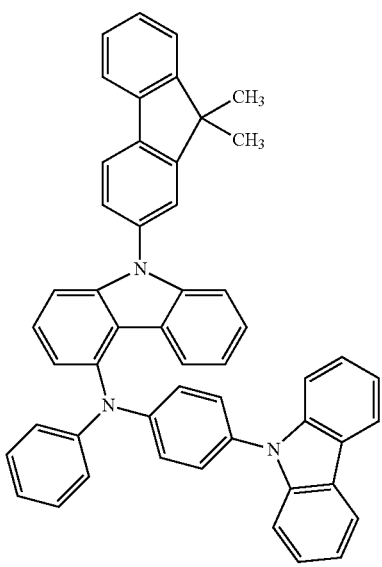
(A30)
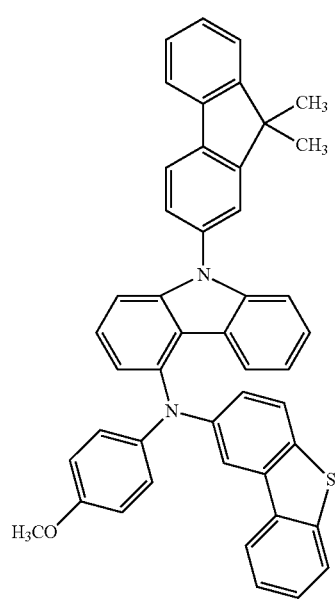
(A32)
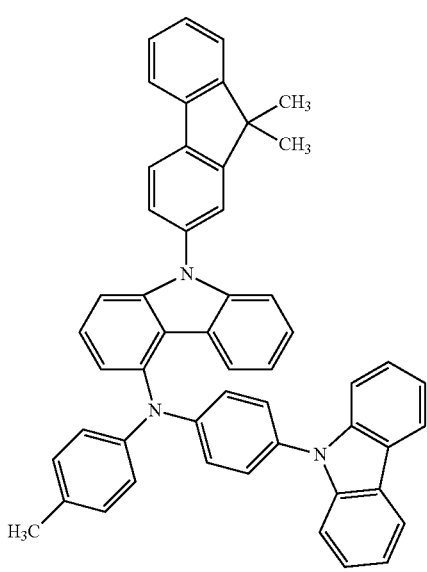

(A33)
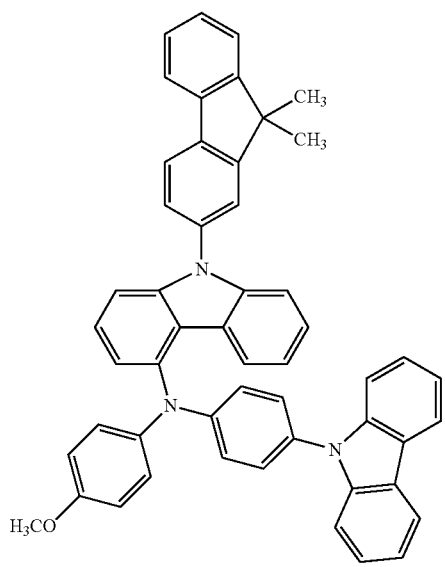
(A34)
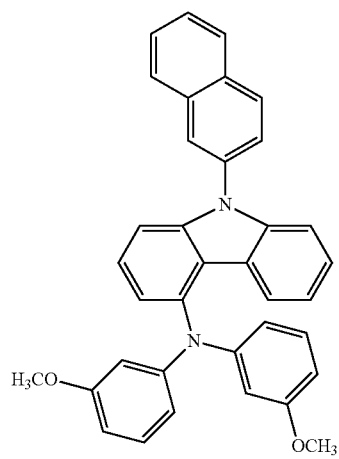
(A35)
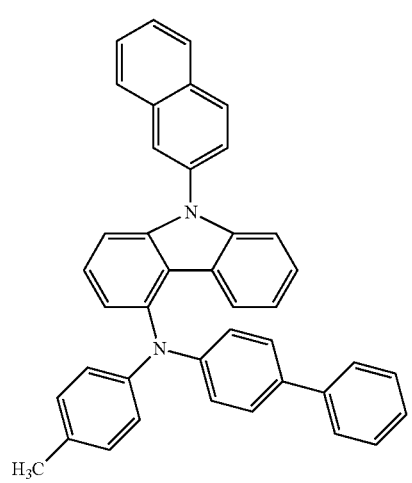
(A36)
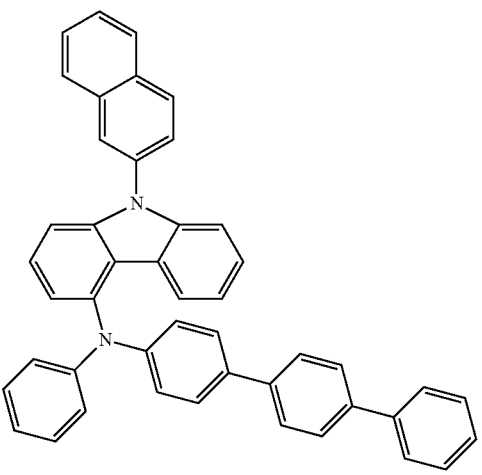
(A37)
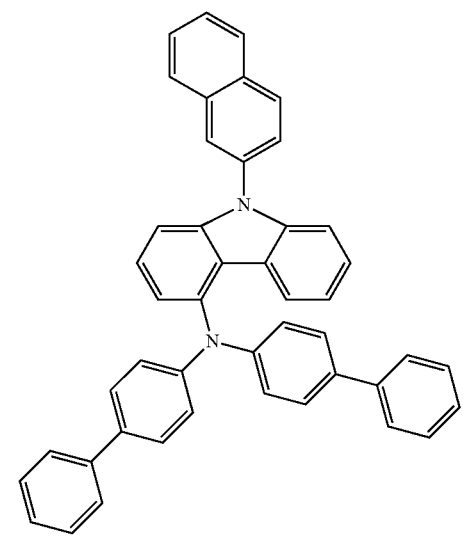
(A38)
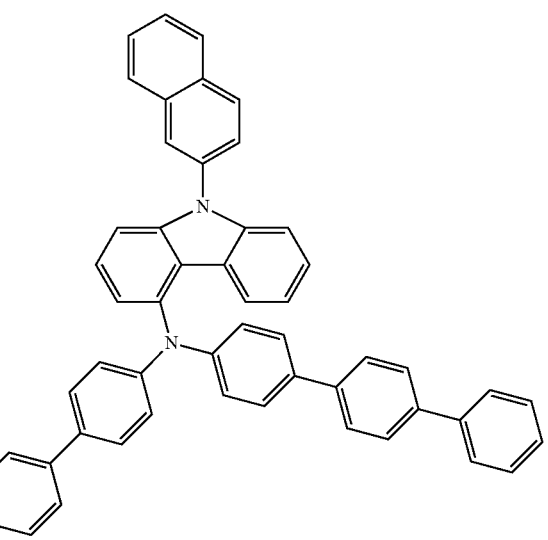

(A39)
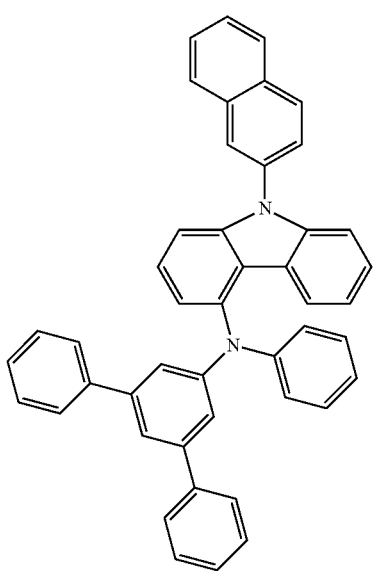
(A40)
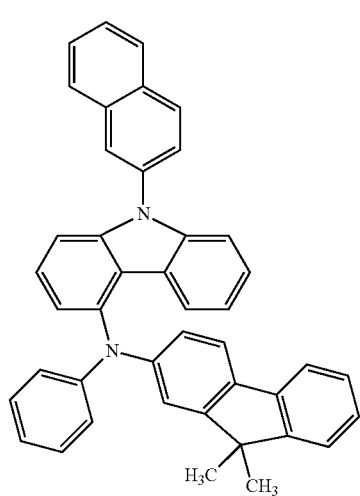
(A41)
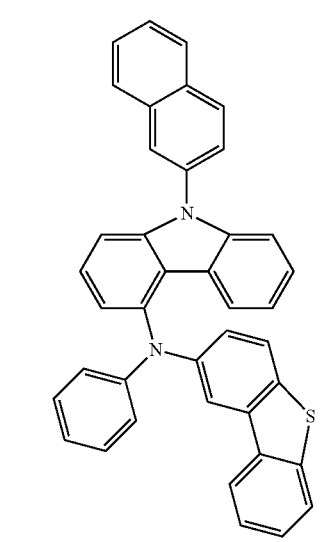
(A42)
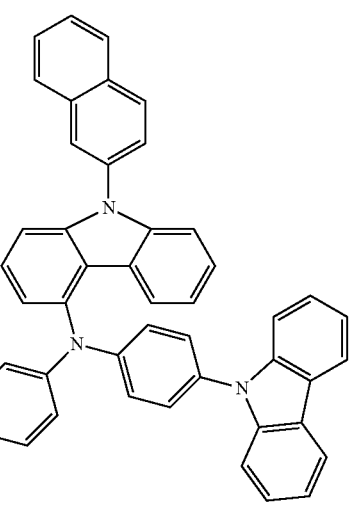
(A43)
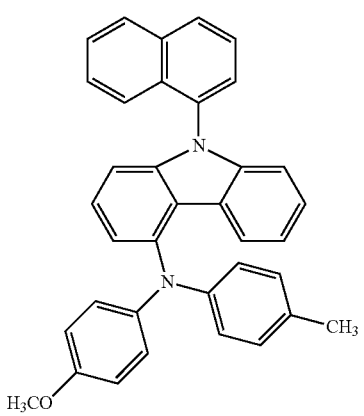
(A44)
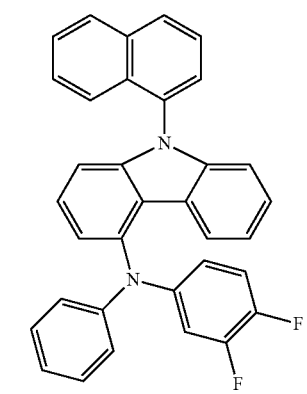

(A45)
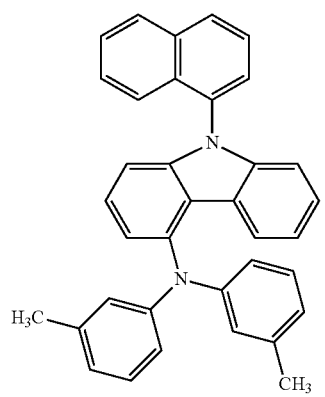
(A46)
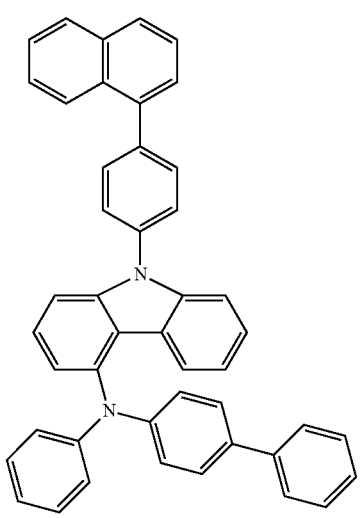
(A47)
(A48)
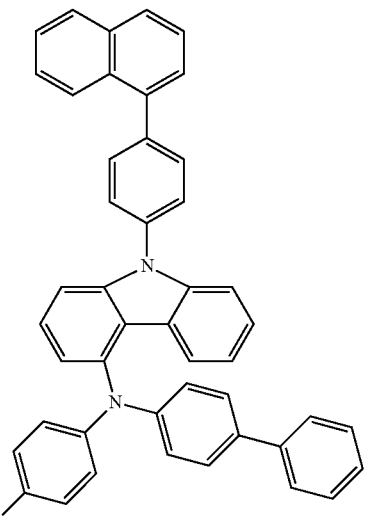
(A49)
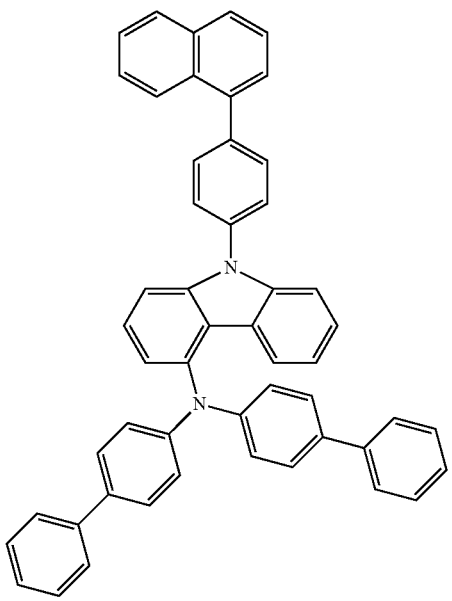

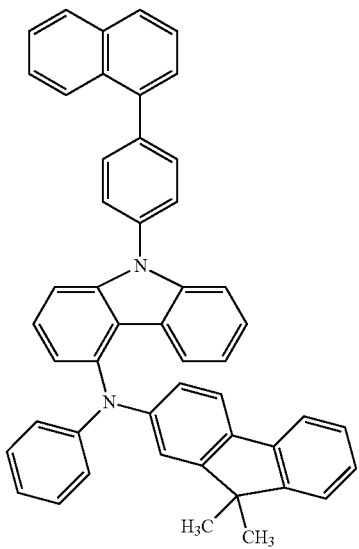 (A50)
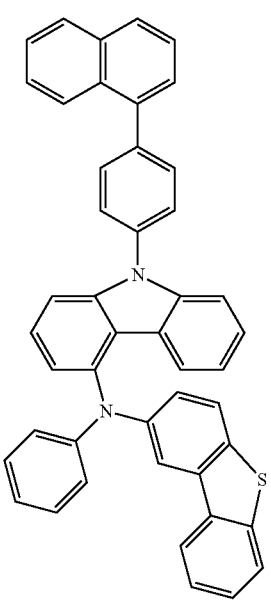 (A51)
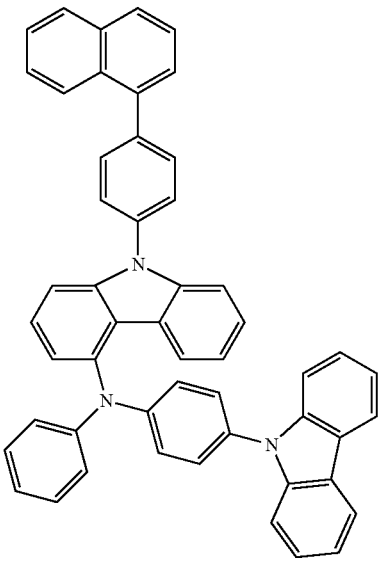 (A52)
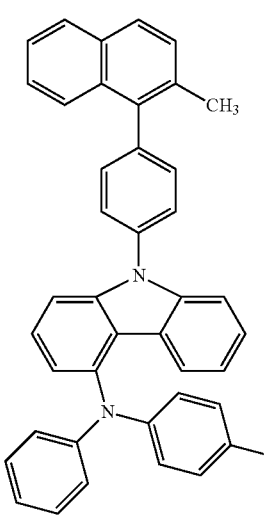 (A53)
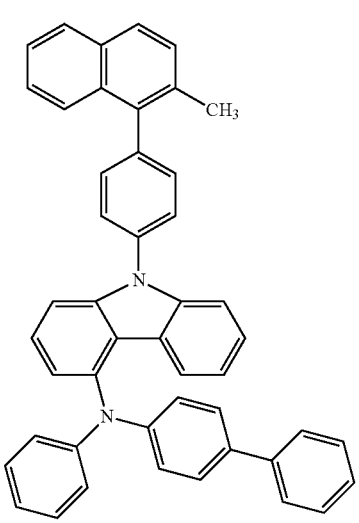 (A54)

(A55)
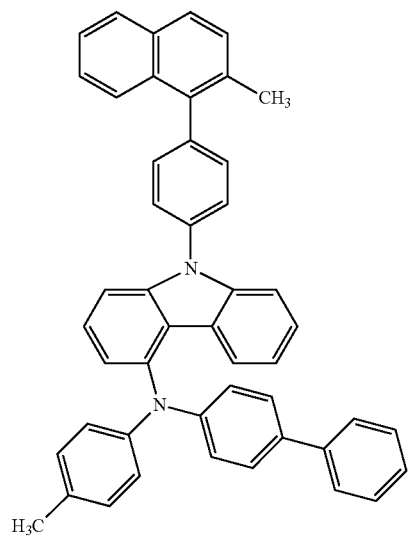
(A56)
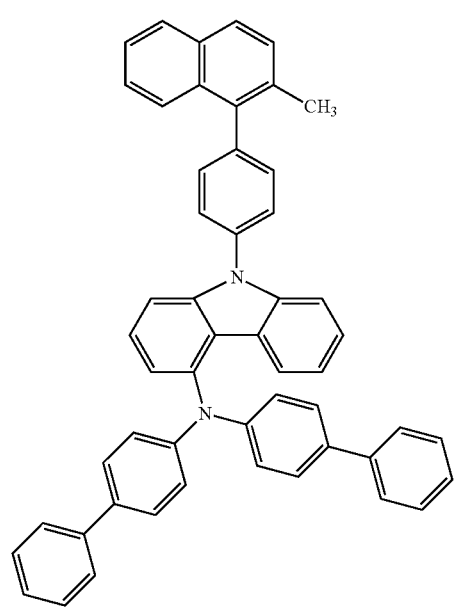
(A57)
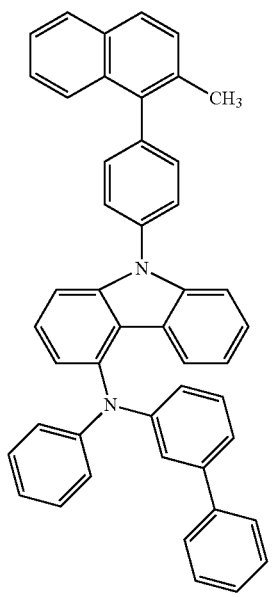
(A58)
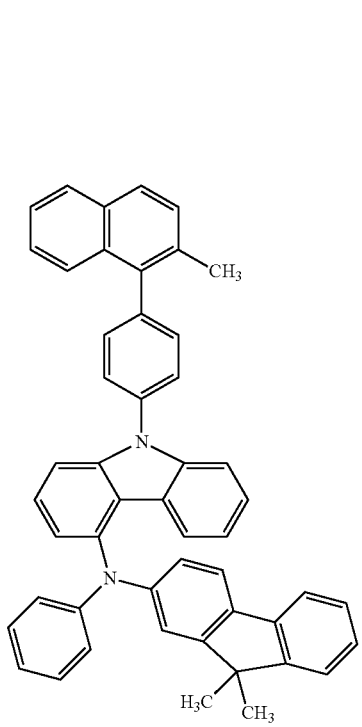

(A59) 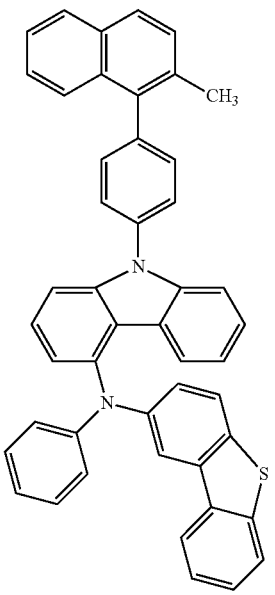
(A60) 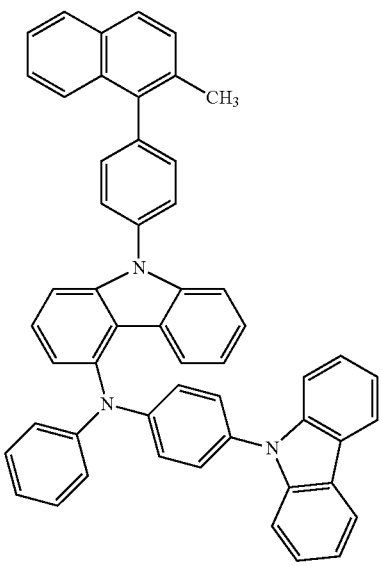
(A61) 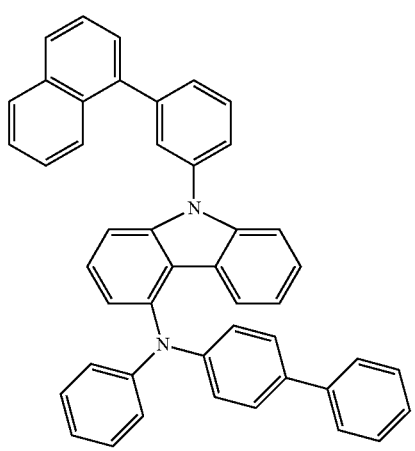
(A62) 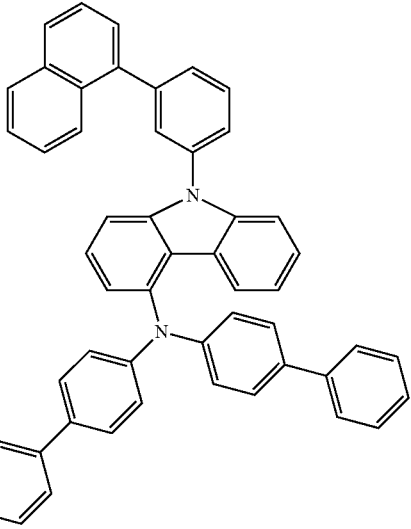
(A63) 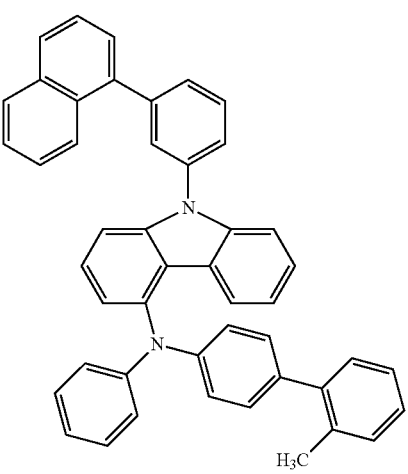
(A64) 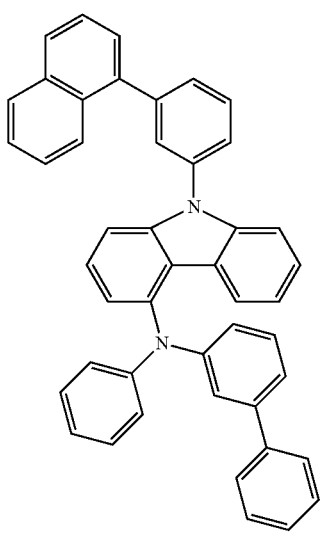

-continued
(A65)
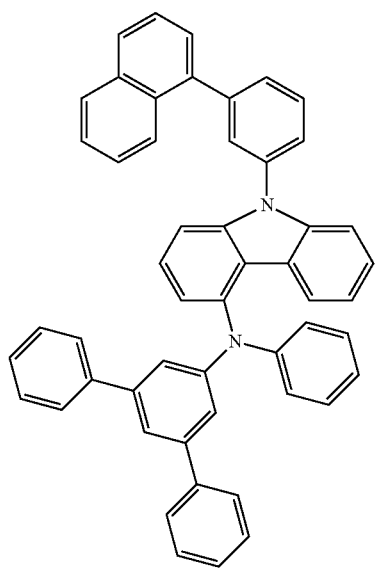
(A68)
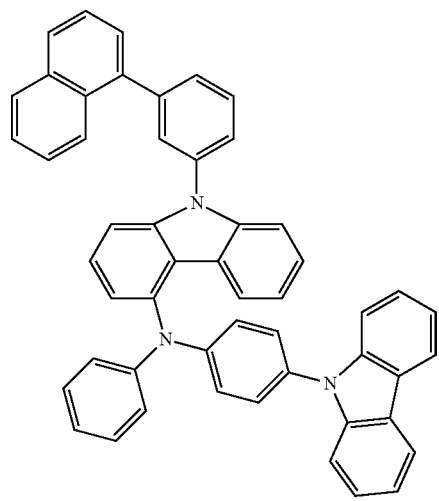
(A66)
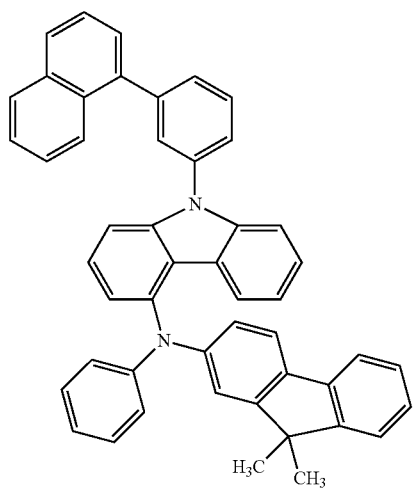
(A69)
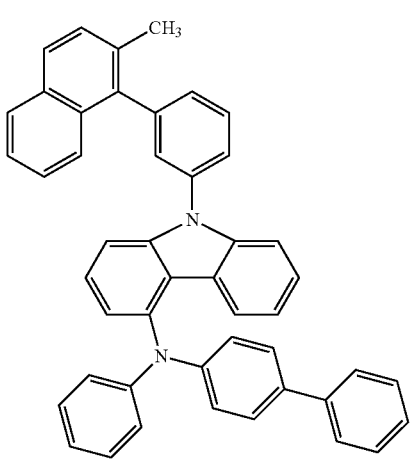
(A67)
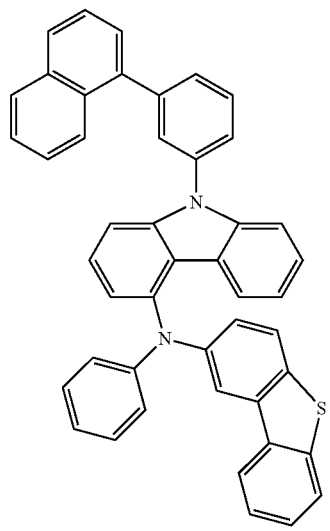
(A70)
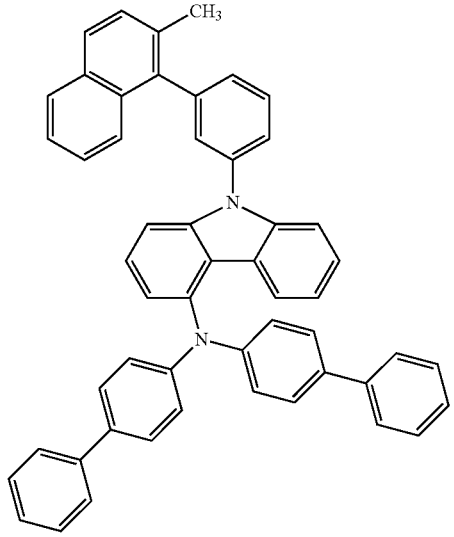

(A71) 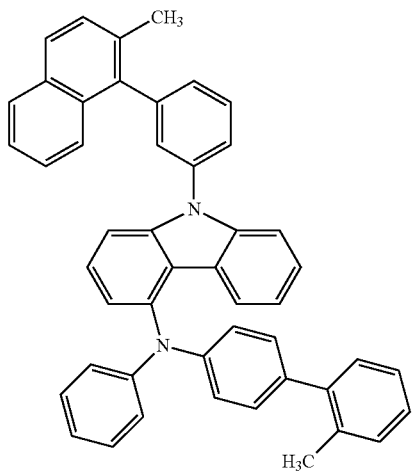
(A72) 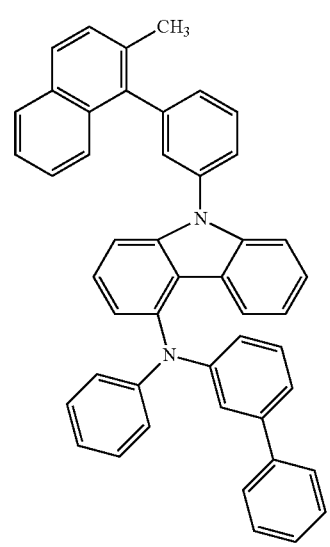
(A73) 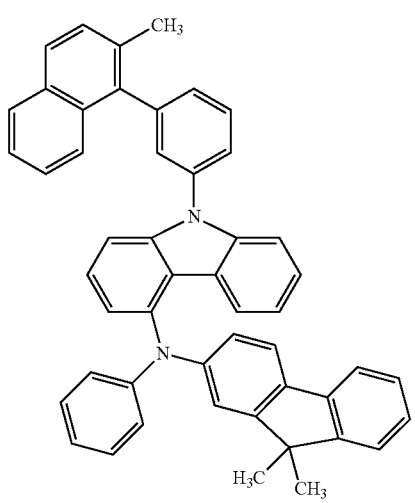
(A74) 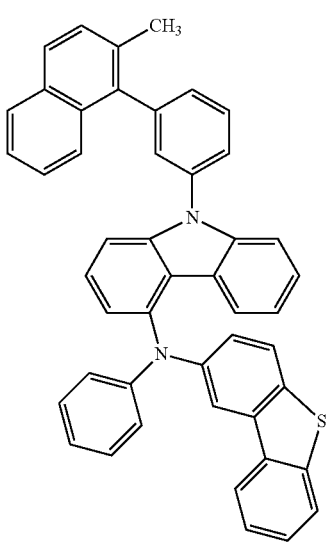
(A75) 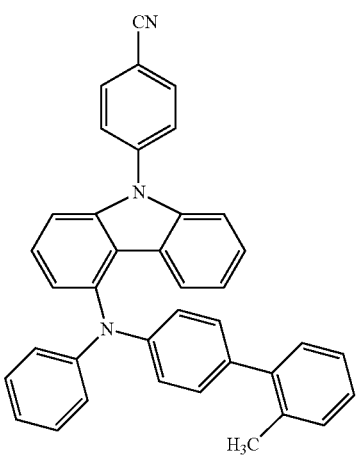
(A76) 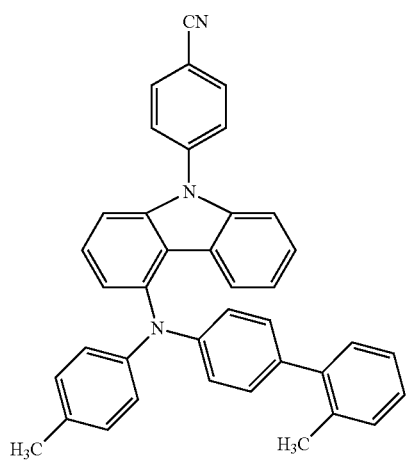

-continued
(A77)
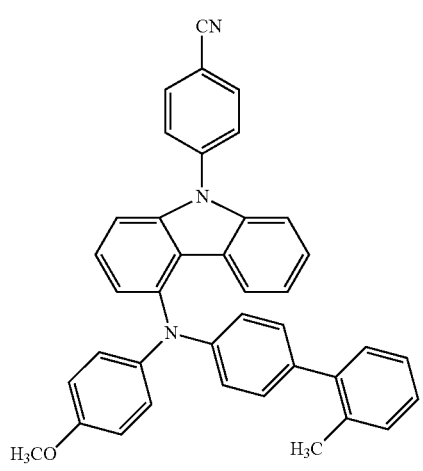
(A78)
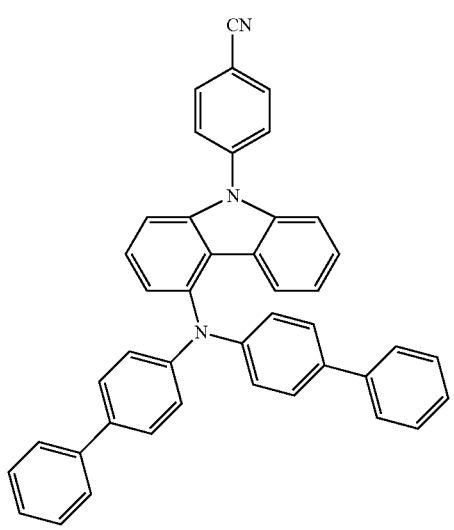
(A79)
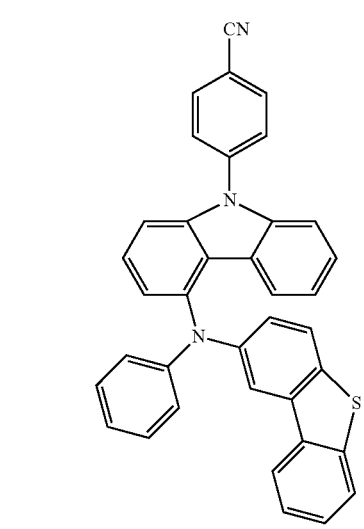
-continued
(A80)
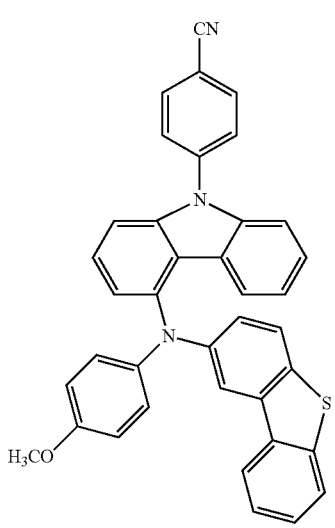
(A81)
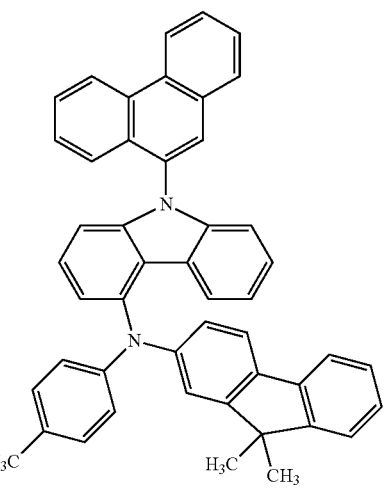
(A82)
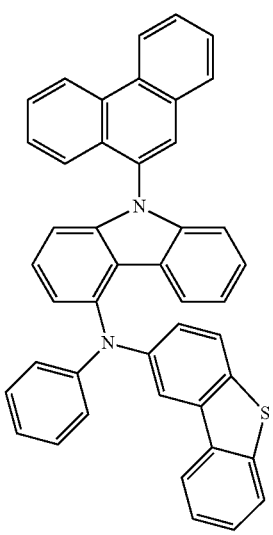

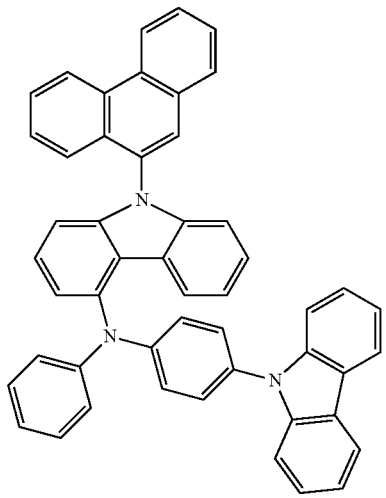
(A83)
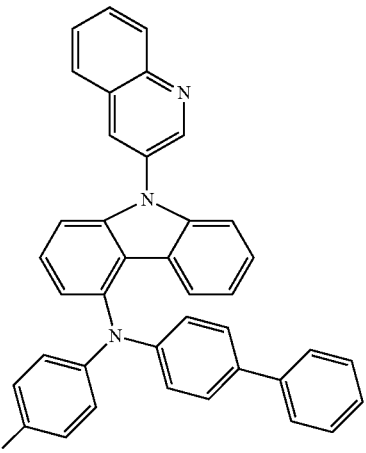
(A86)
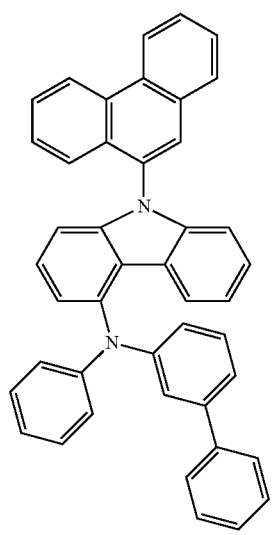
(A84)
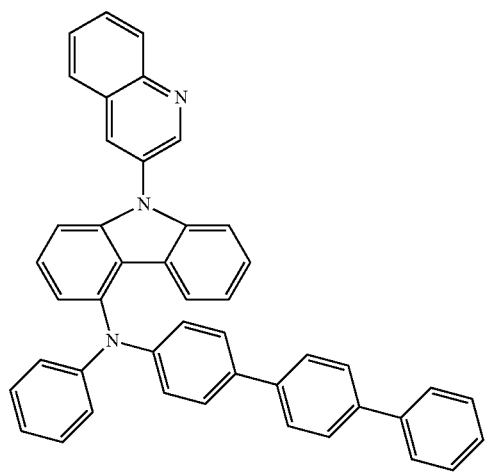
(A87)
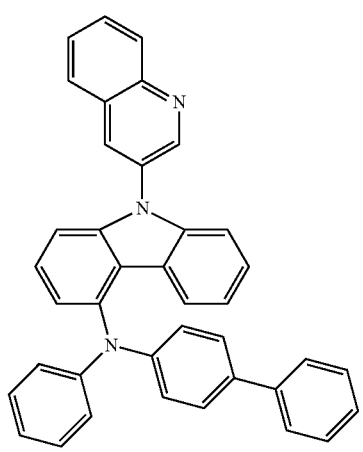
(A85)
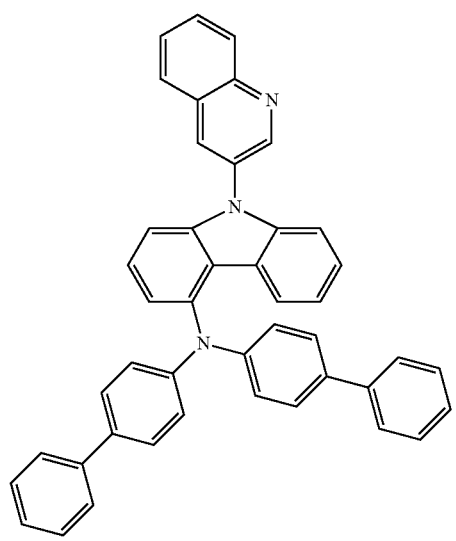
(A88)

-continued
(A89)
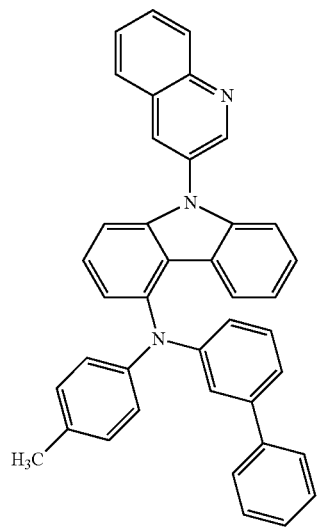
(A90)
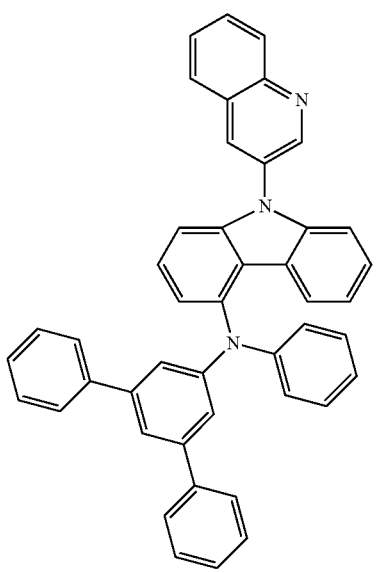
(A91)
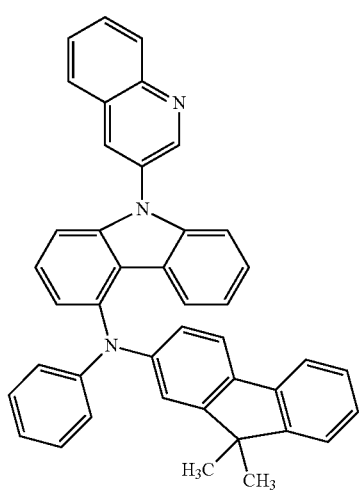
-continued
(A92)
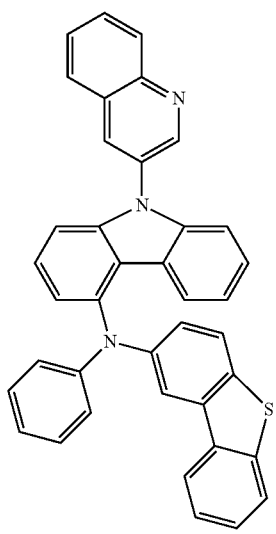
(A93)
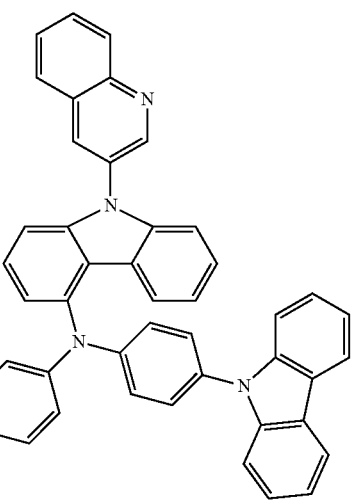
(A94)
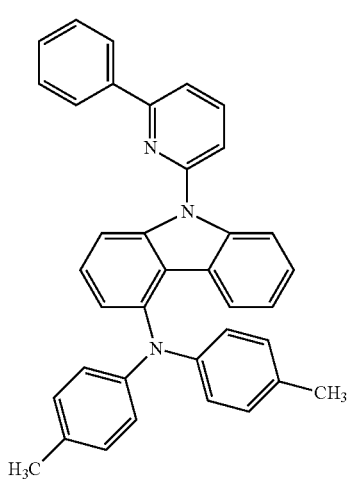

(A95) 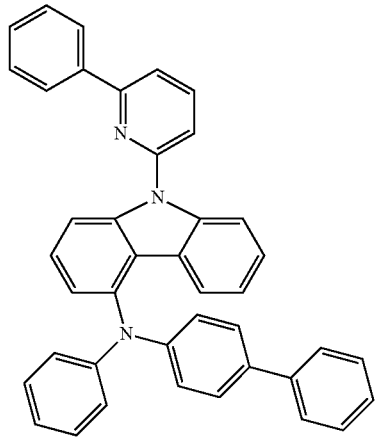
(A96) 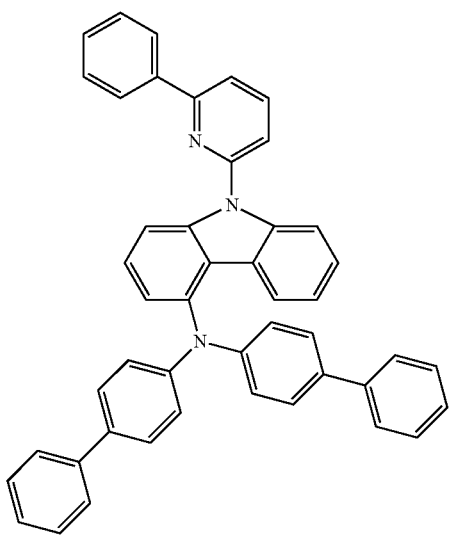
(A97) 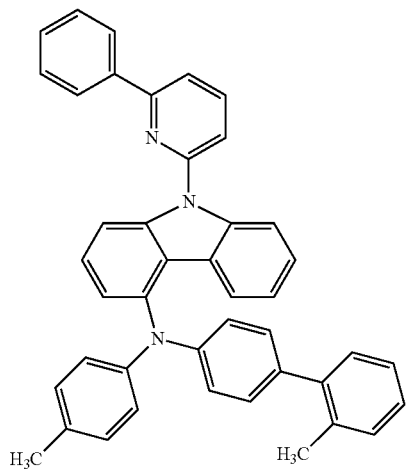
(A98) 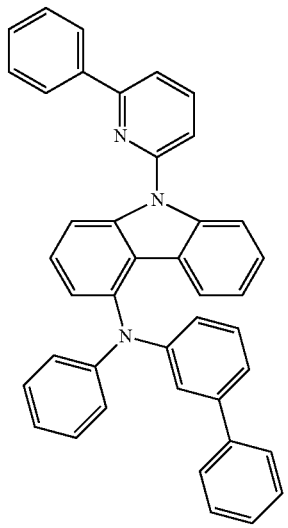
(A99) 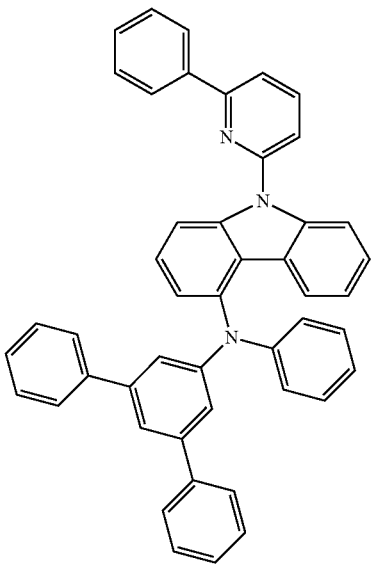
(A100) 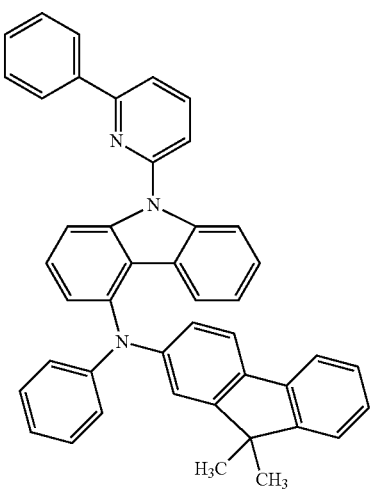

-continued
(A101)
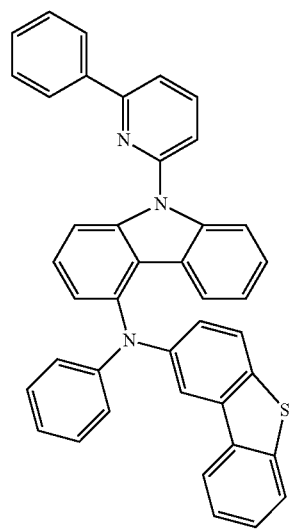
(A102)
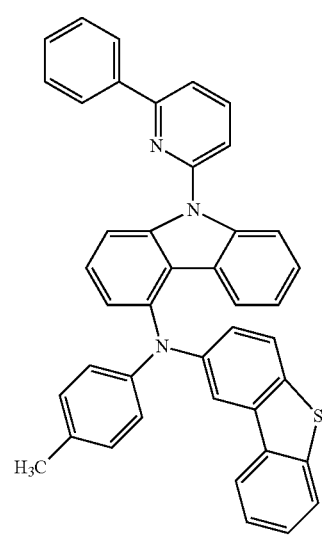
(A103)
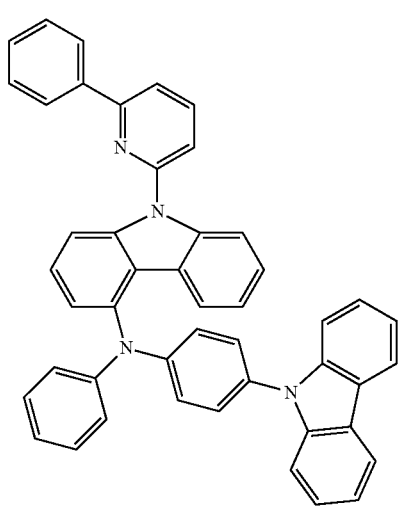
-continued
(A104)
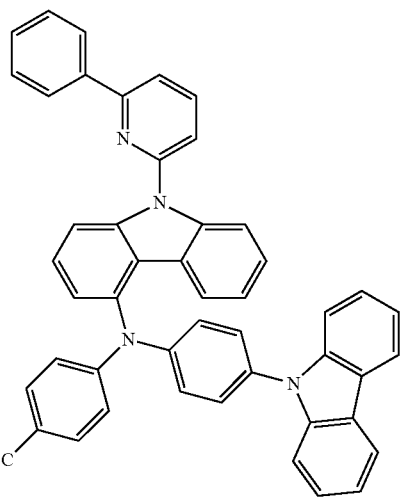
(A105)
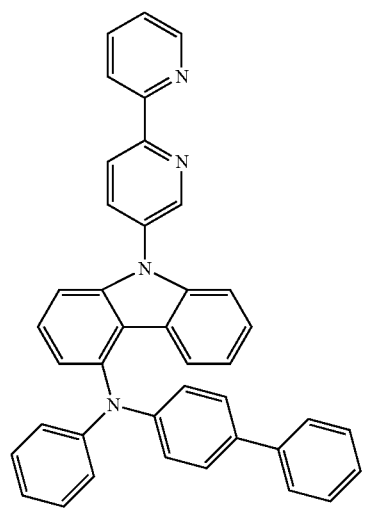
(A106)
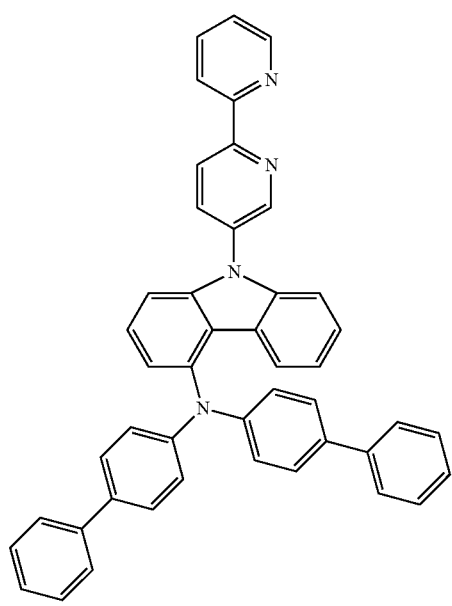

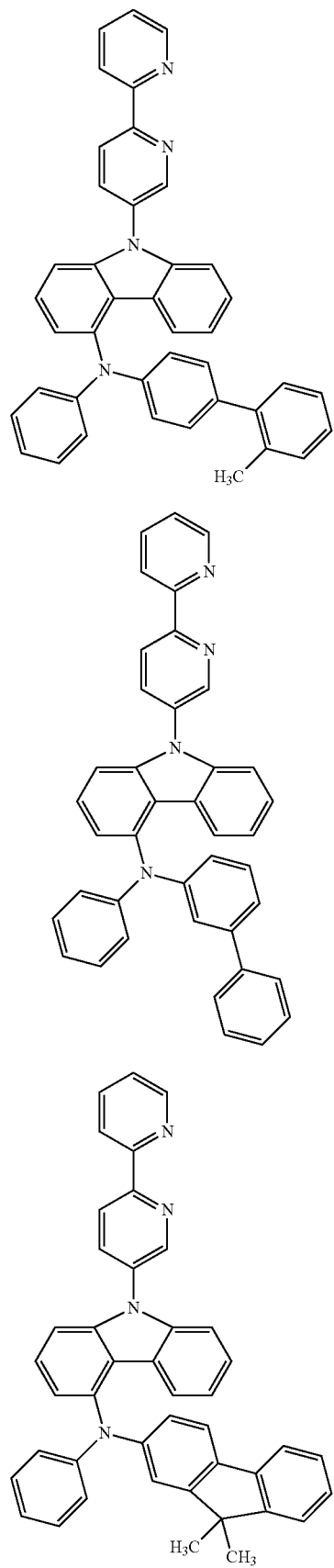
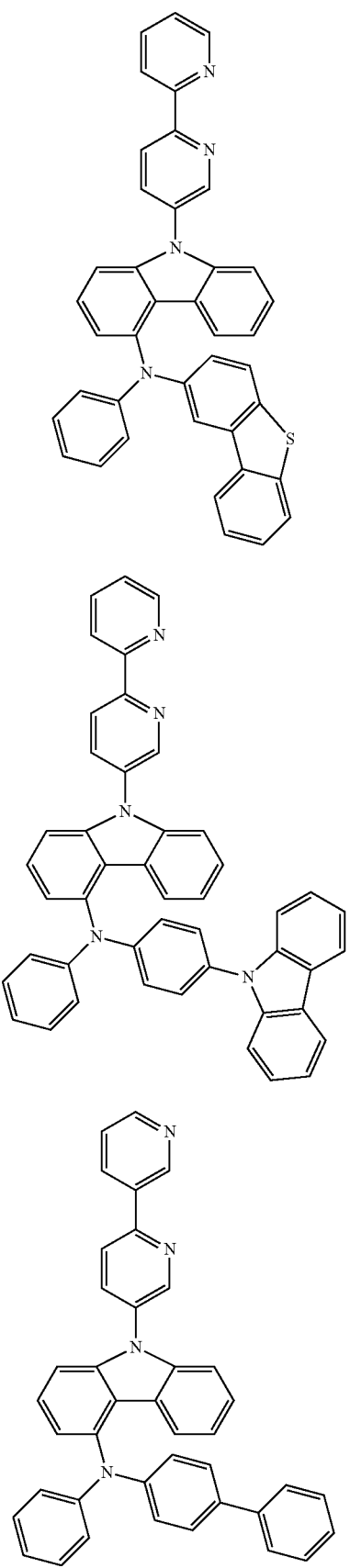

(A113)
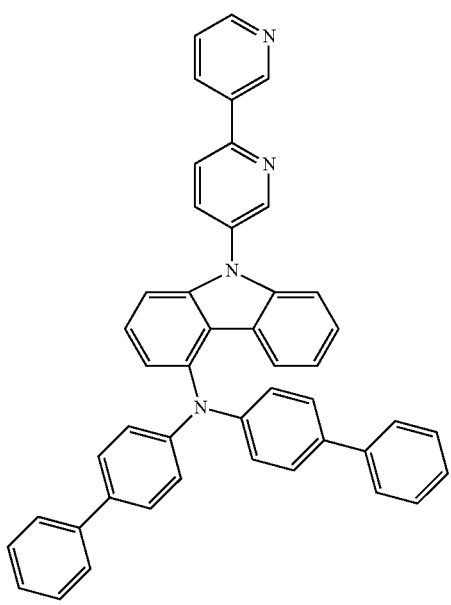
(A114)
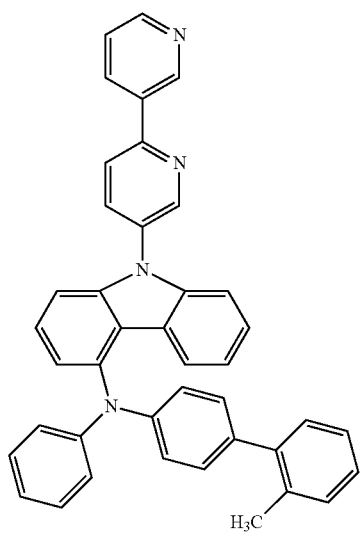
(A115)
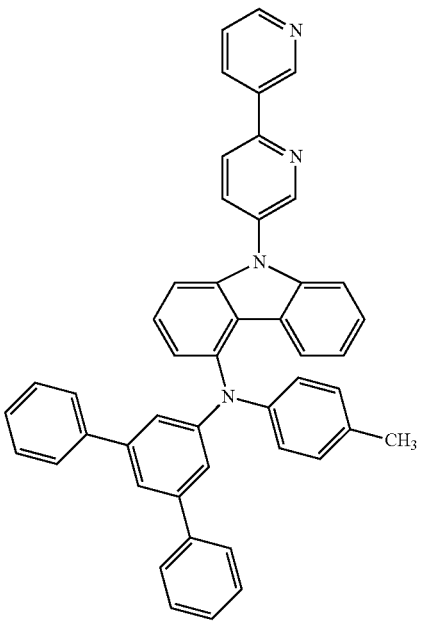
(A116)
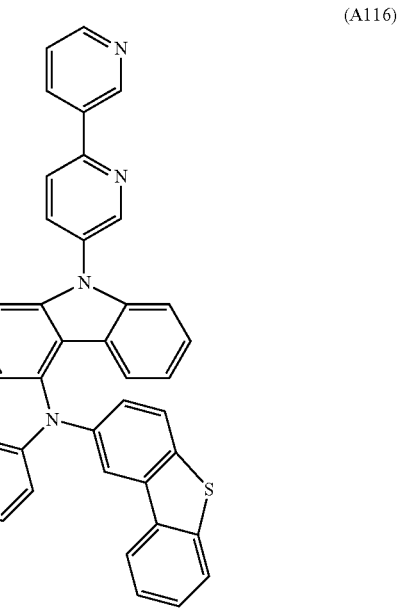
(A117)
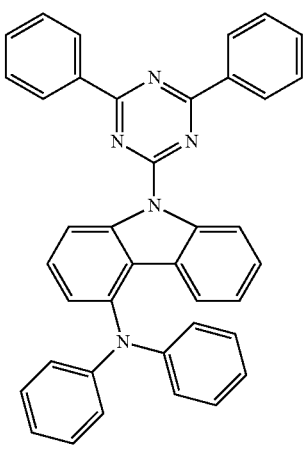

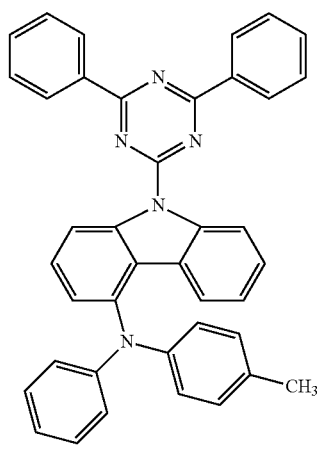 (A118)
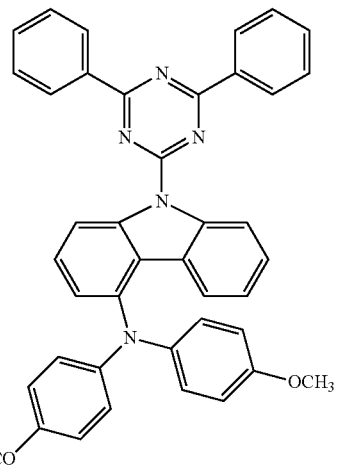 (A121)
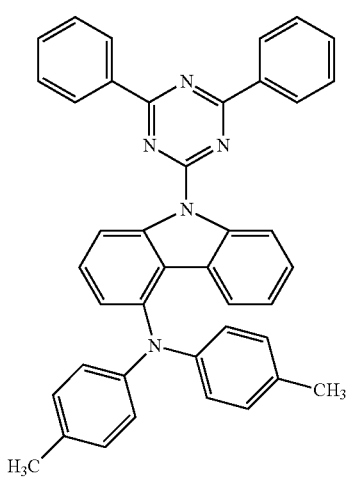 (A119)
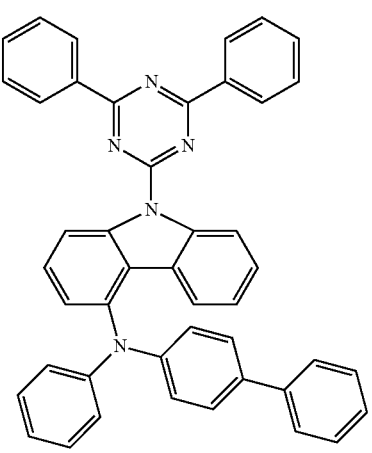 (A122)
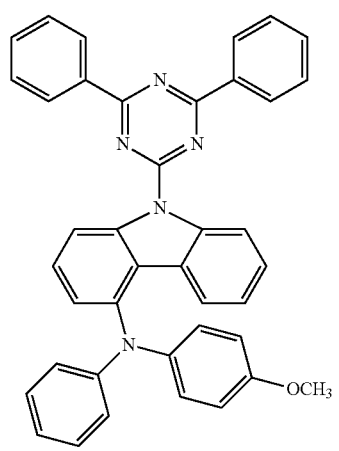 (A120)
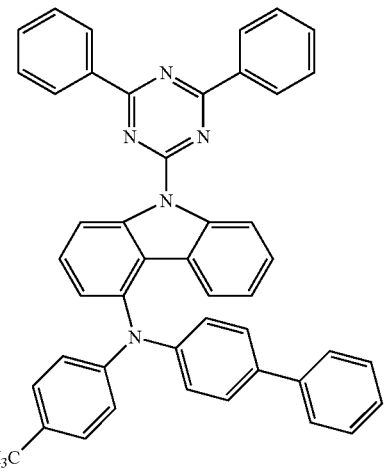 (A123)

(A124)
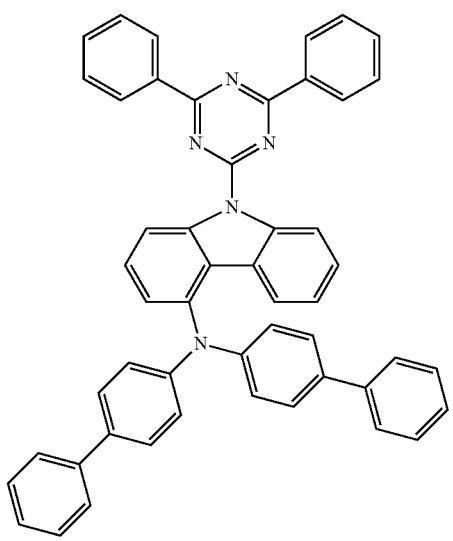
(A125)
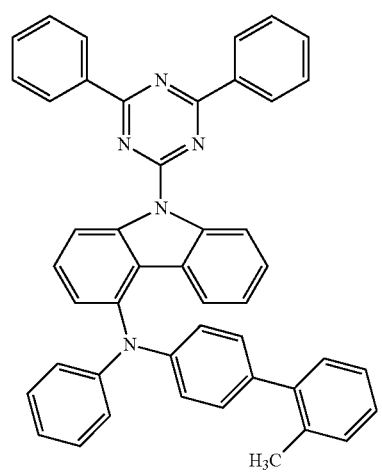
(A126)
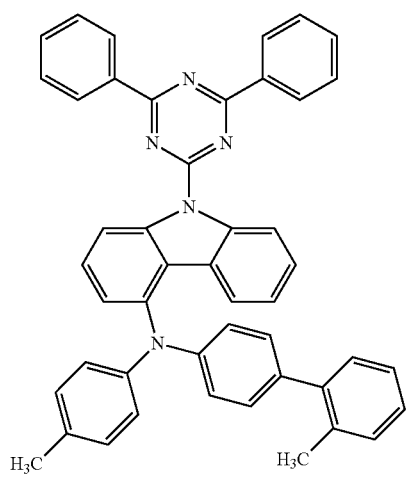
(A127)
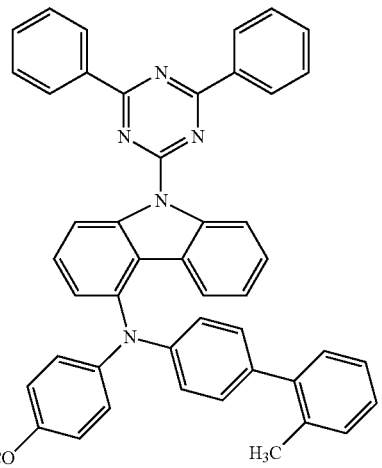
(A128)
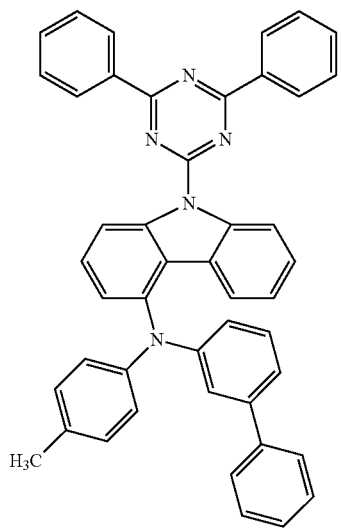
(A129)
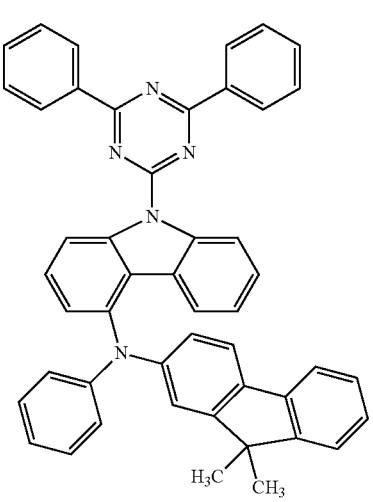

(A130) 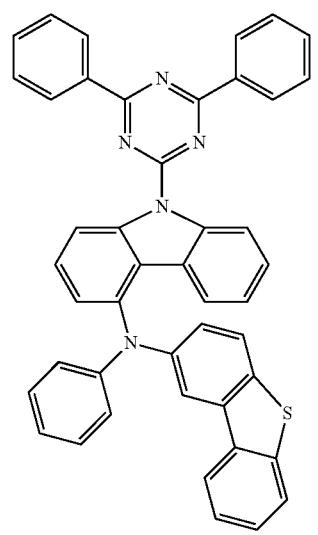
(A131) 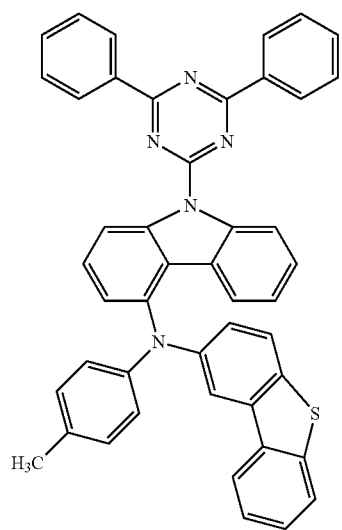
(A132) 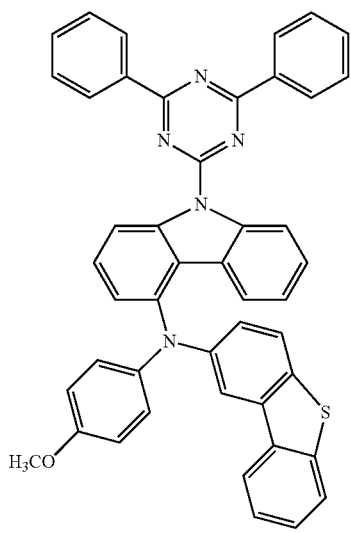
(A133) 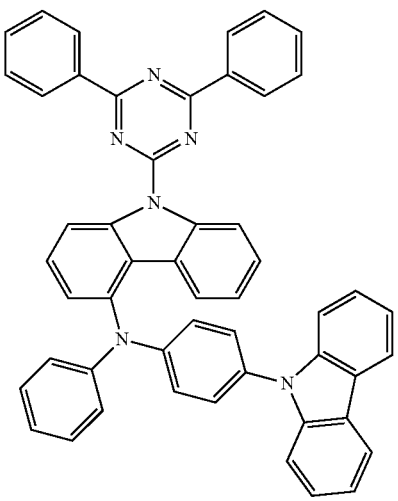
(A134)
(A135)

(A136) 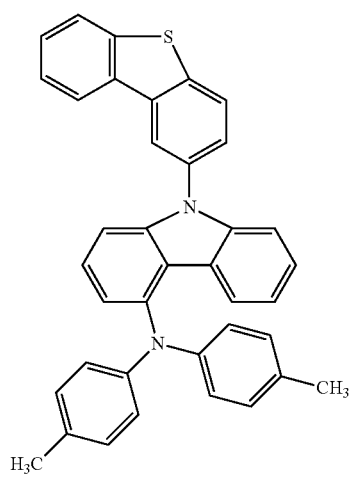
(A137) 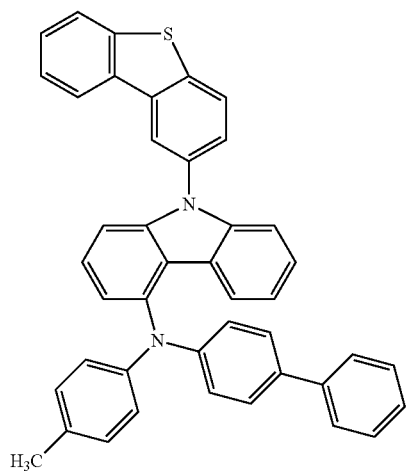
(A138) 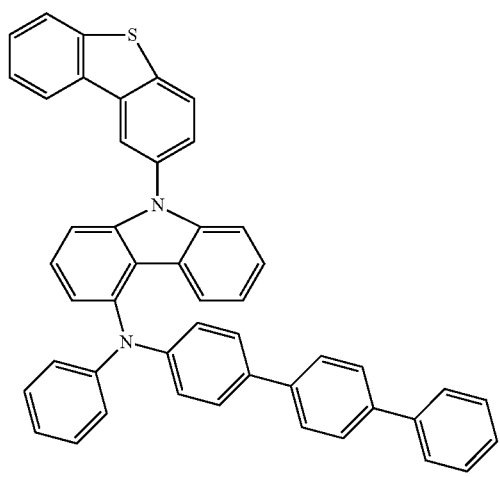
(A139) 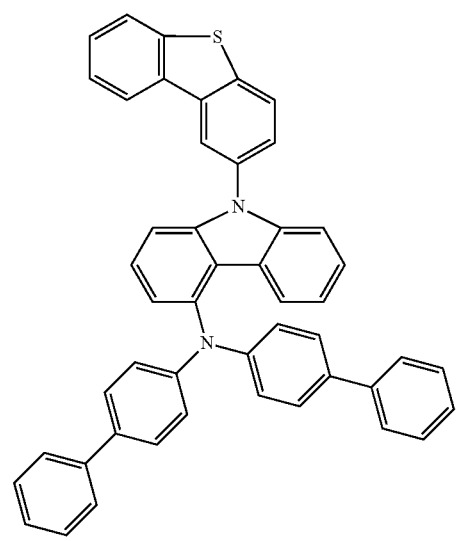
(A140) 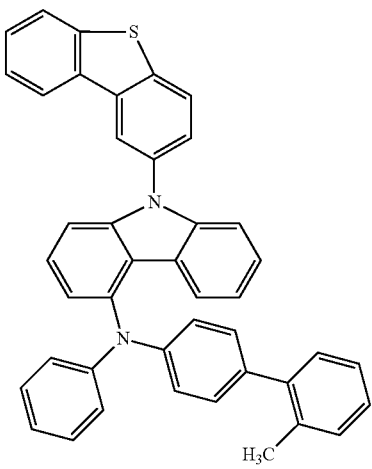
(A141) 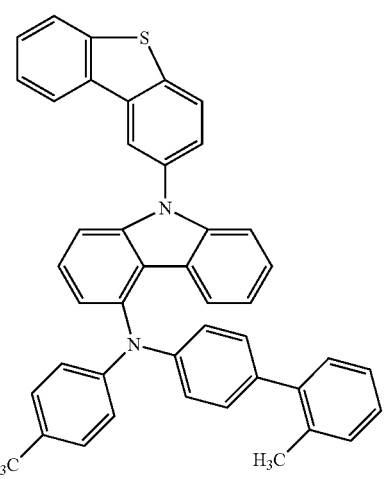

(A142)
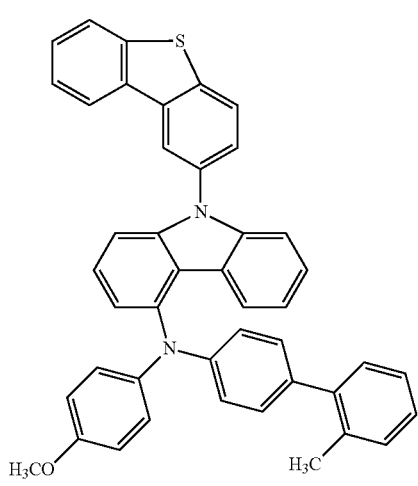
(A143)
(A144)
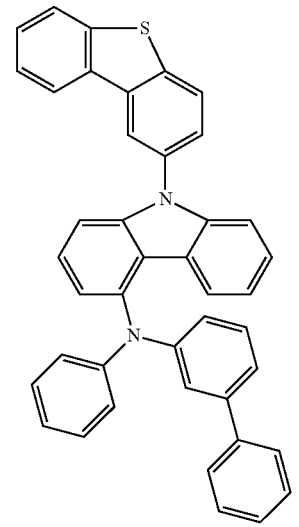
(A145)
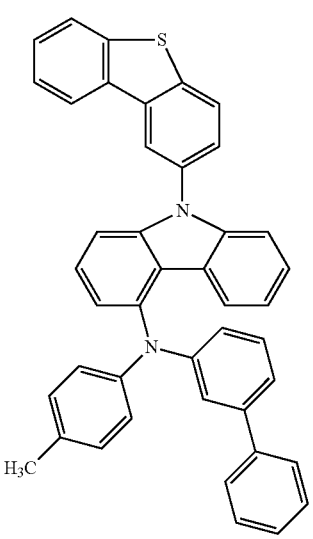
(A146)
(A147)
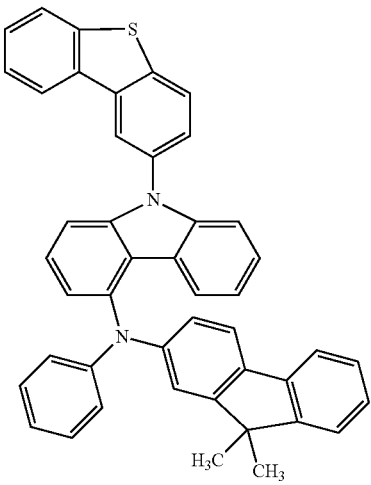

(A148)
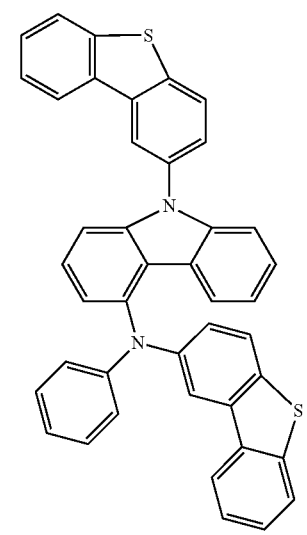
(A149)
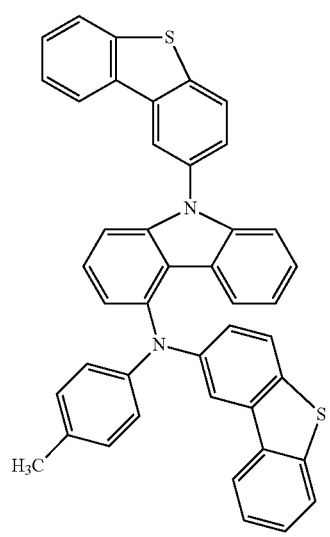
(A150)
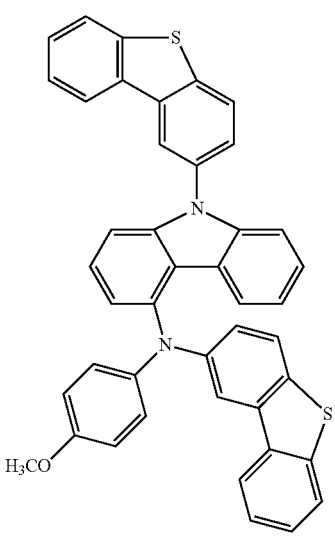
(A151)
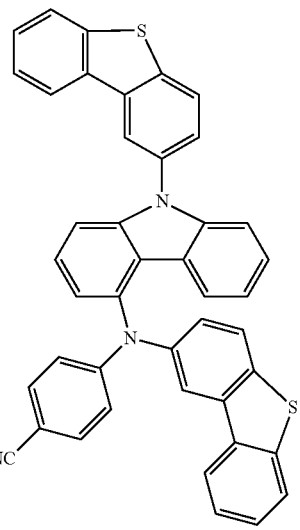
(A152)
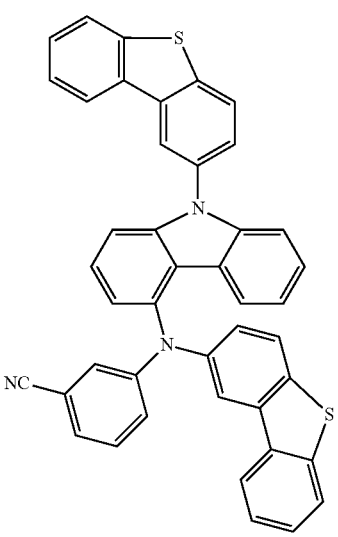
(A153)
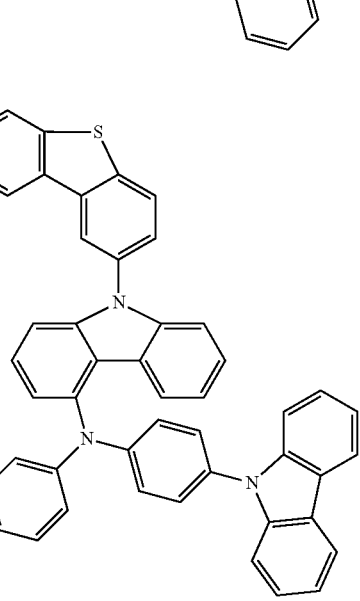

-continued
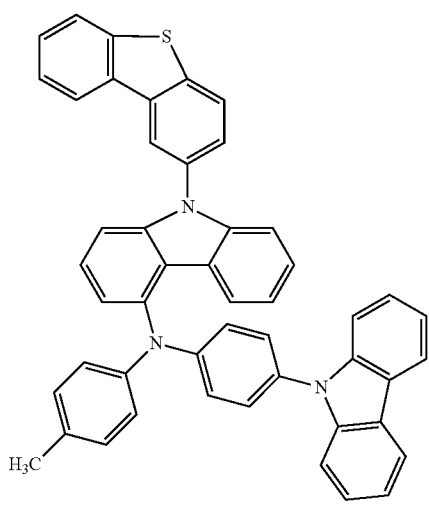
(A154)
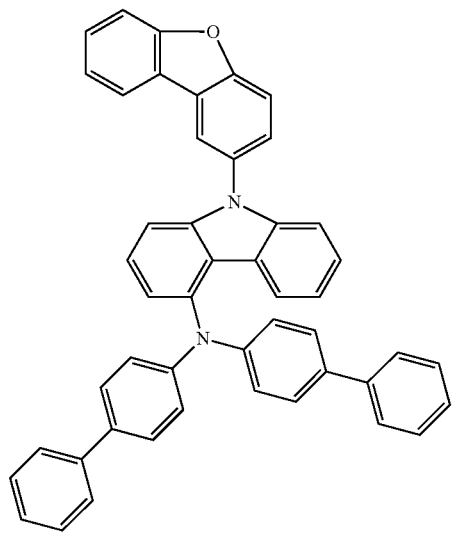
(A157)
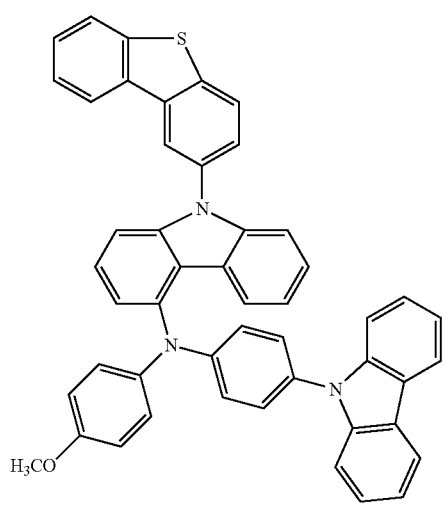
(A155)
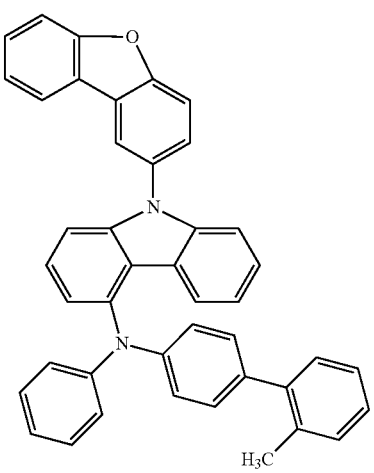
(A158)
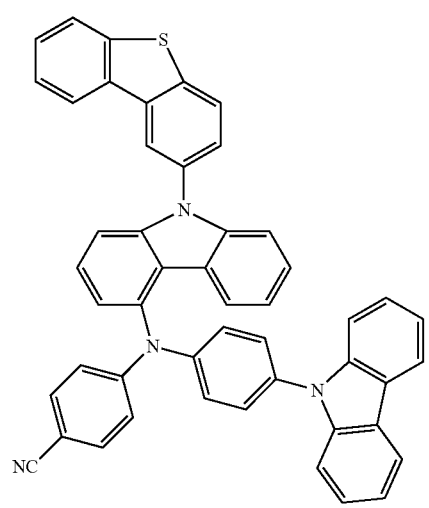
(A156)
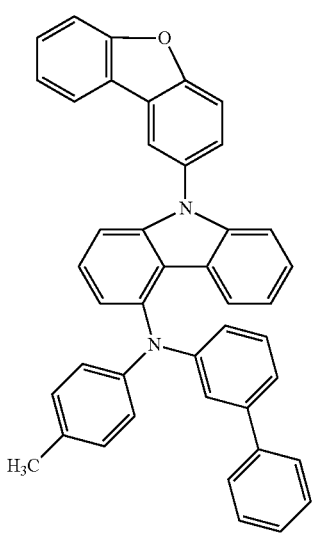
(A159)

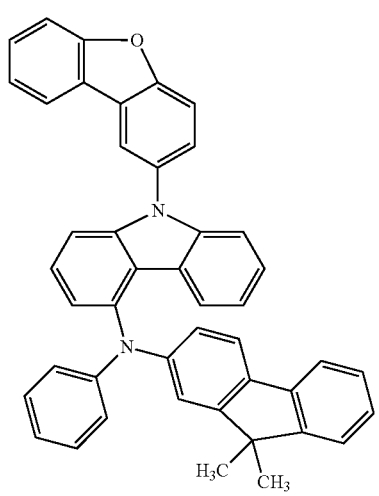
(A160)
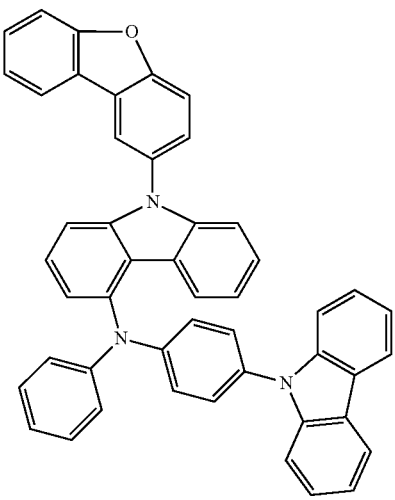
(A163)
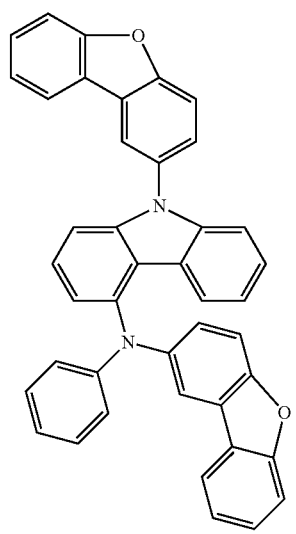
(A161)
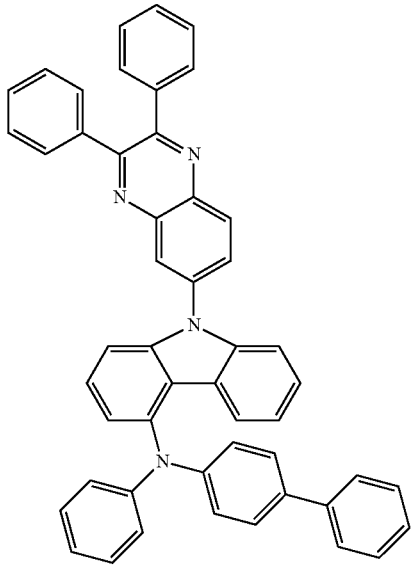
(A164)
(A162)

(A165)
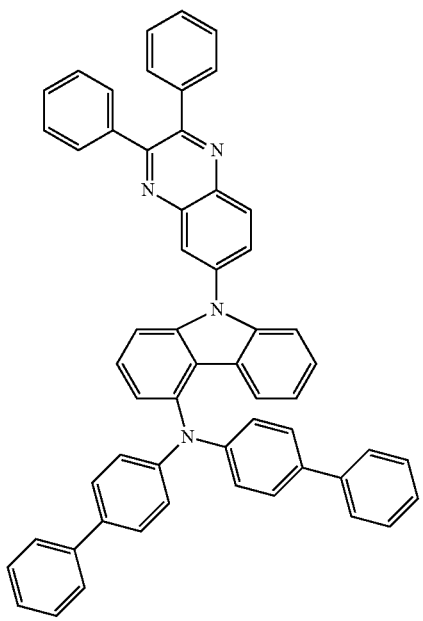
(A166)
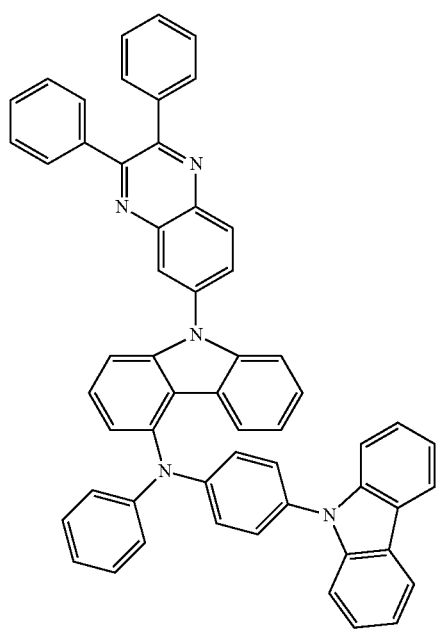
(A167)
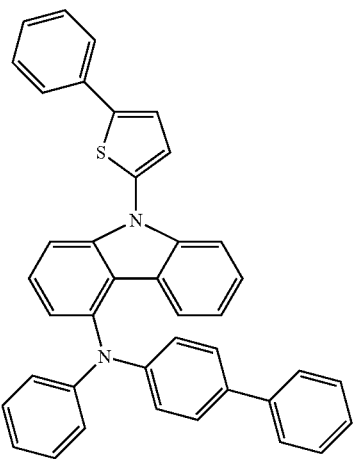
(A168)
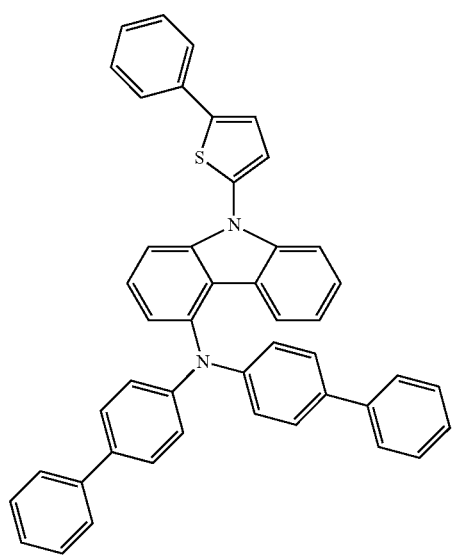
(A169)

81
-continued
(A170)
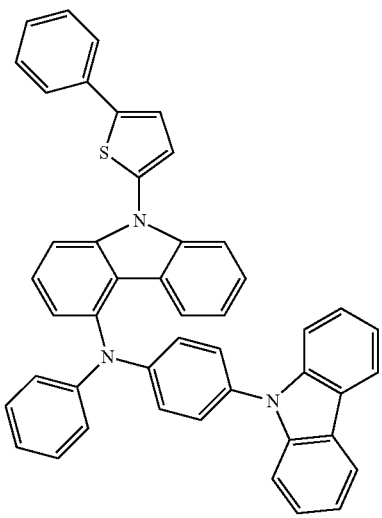
(A171)
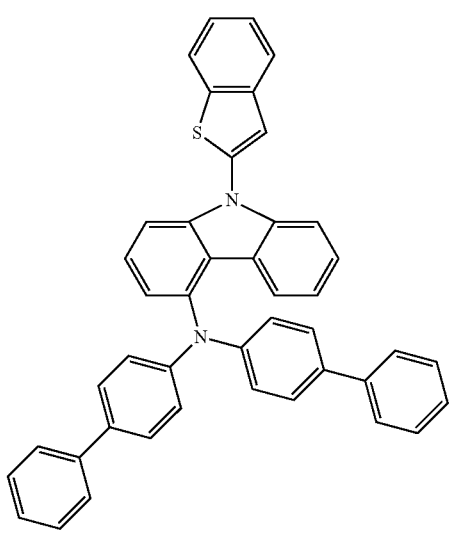
(A172)
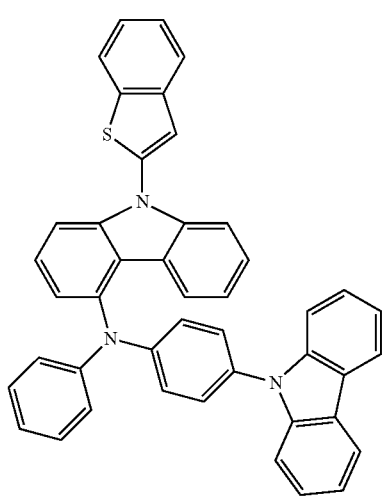
82
-continued
(A173)
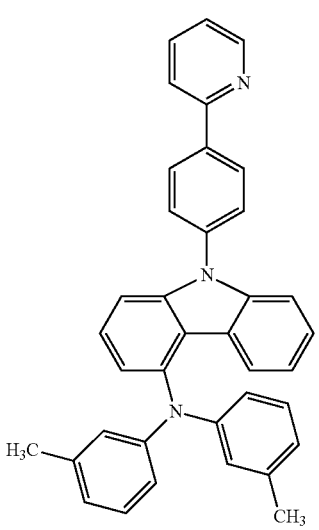
(A174)
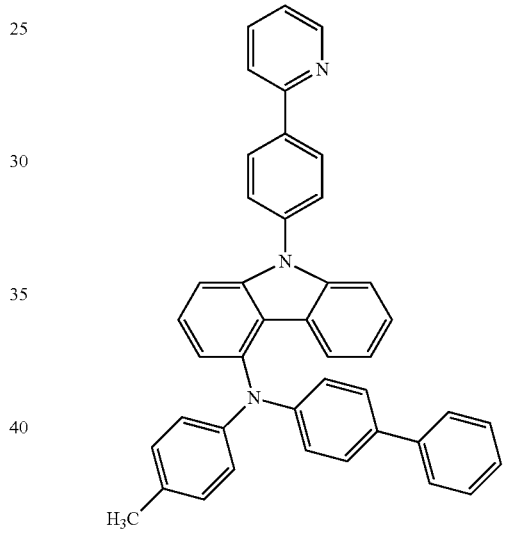
(A175)
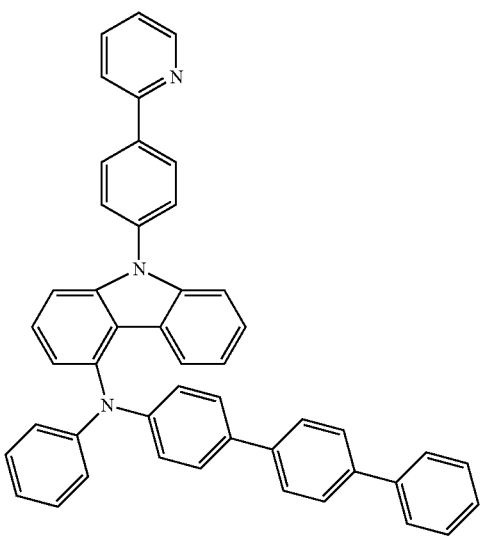

(A176)
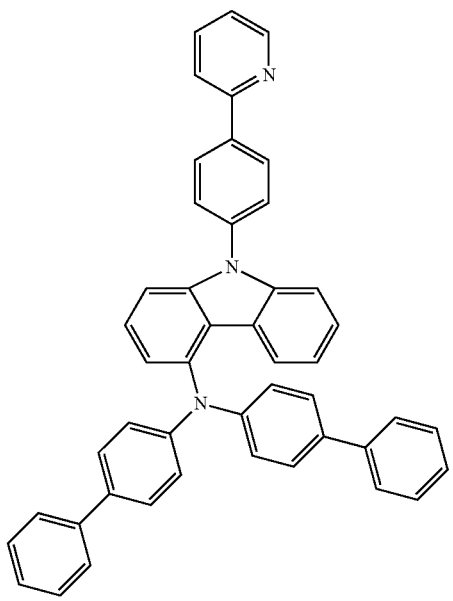
(A177)
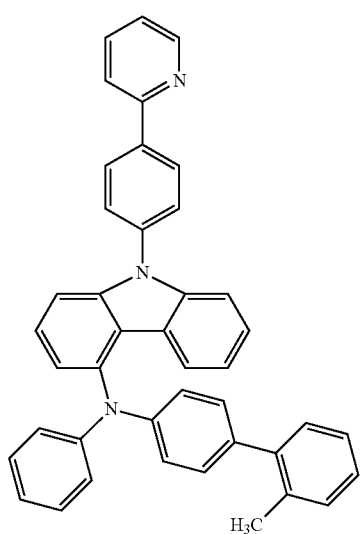
(A178)
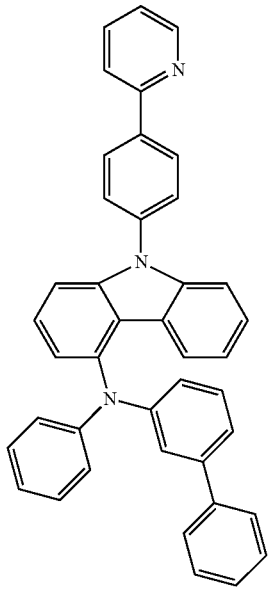
(A179)
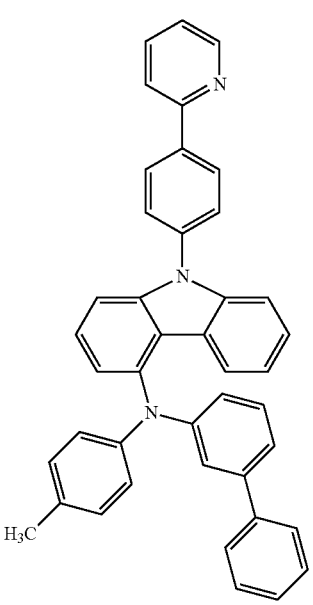

(A180)
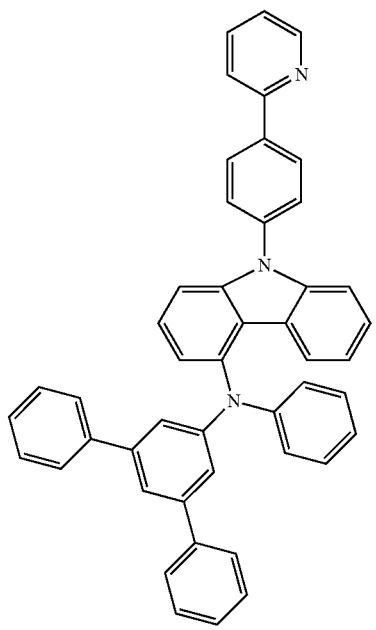
(A182)
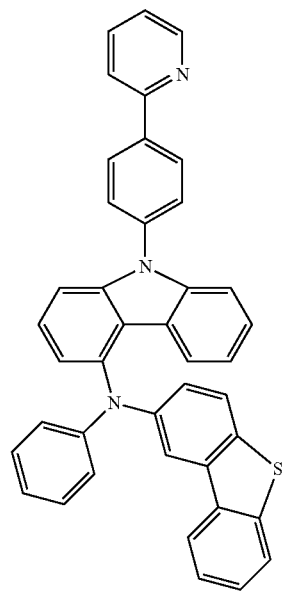
(A181)
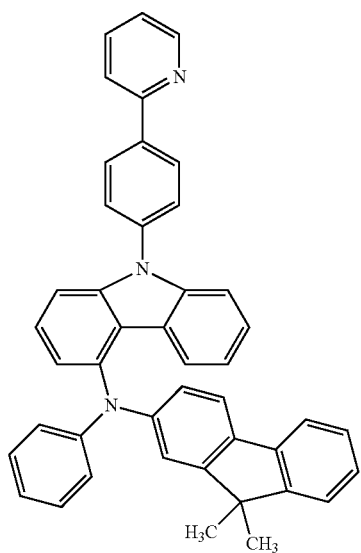
(A183)
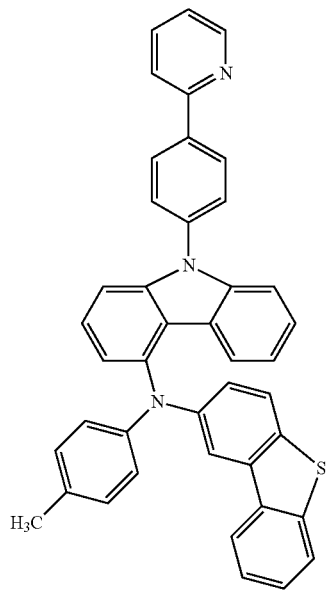

-continued
(A184)
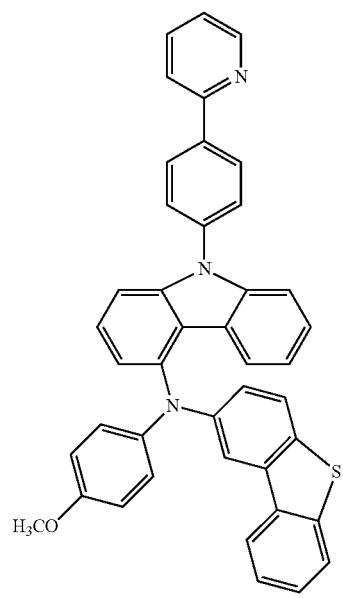
(A185)
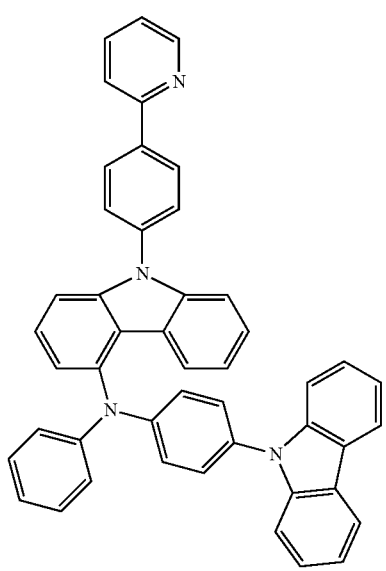
(A186)
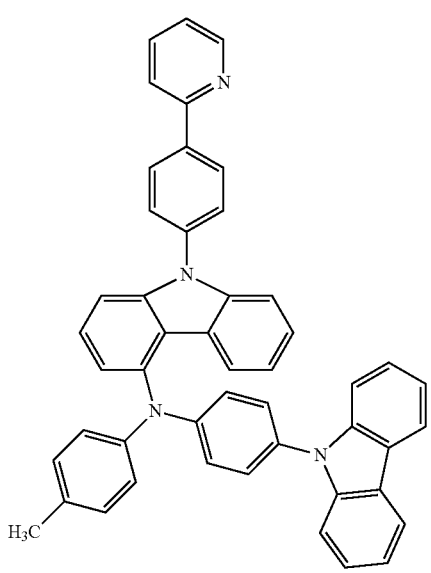
(A187)
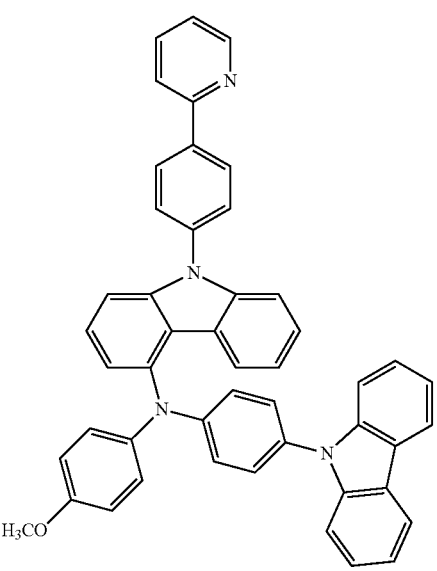
(A188)
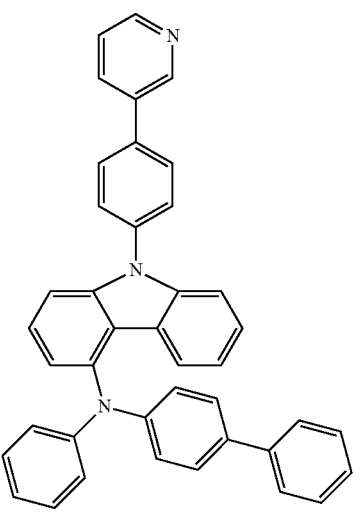

-continued
(A189)
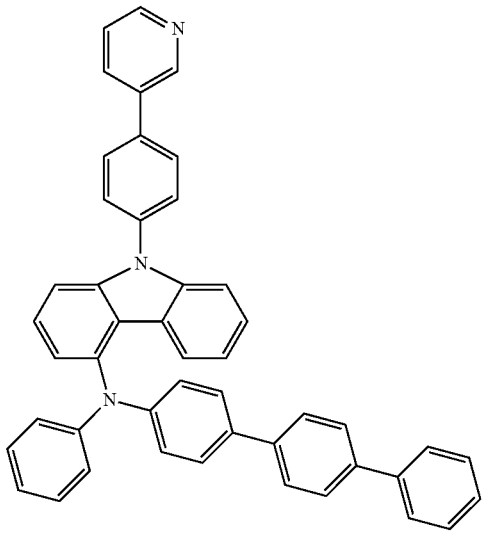
(A190)
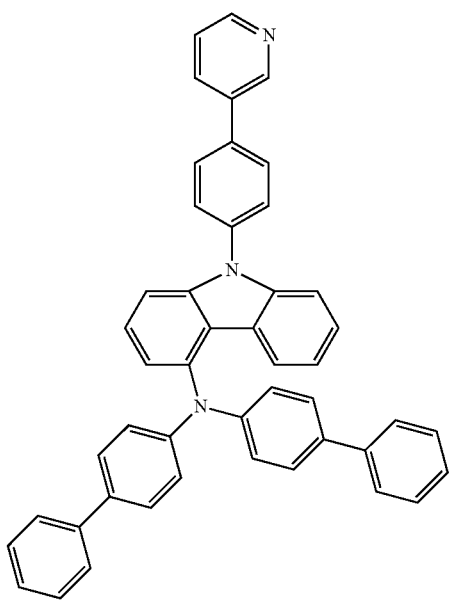
(A191)
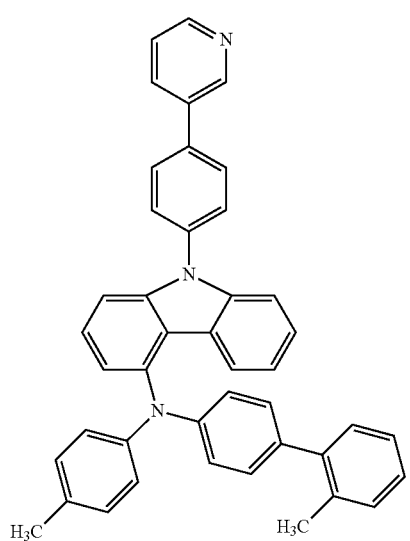
(A192)
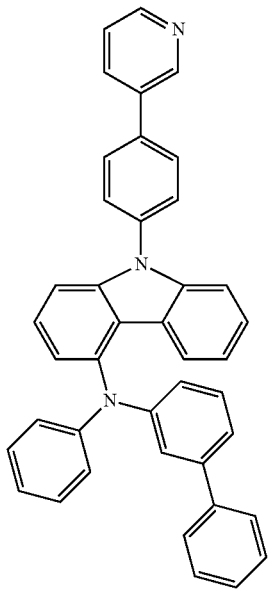
(A193)
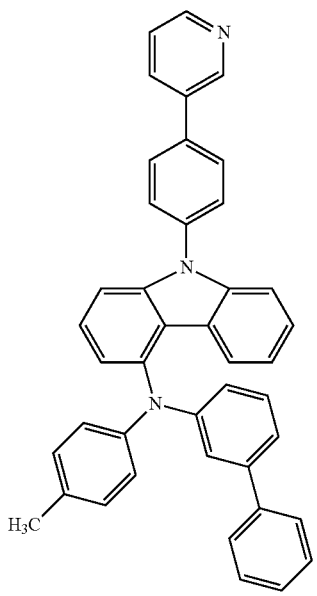

(A194)
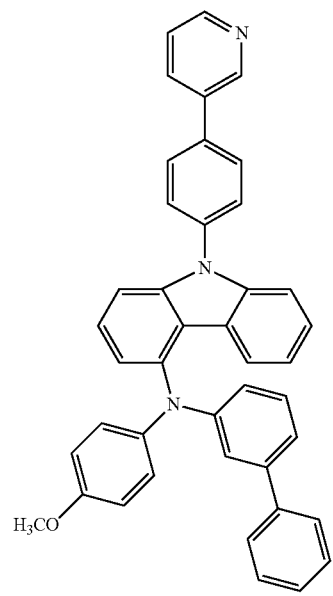
(A196)
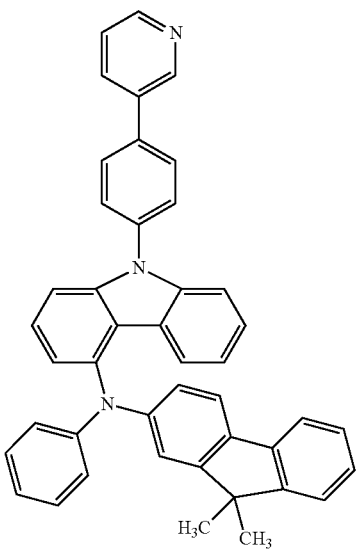
(A195)
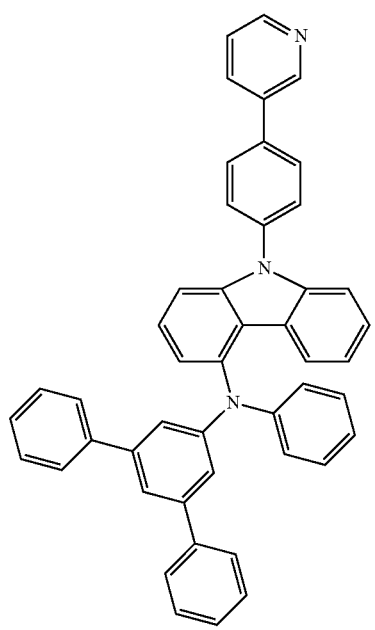
(A197)
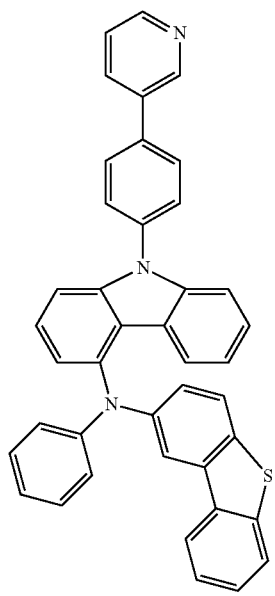

(A198)
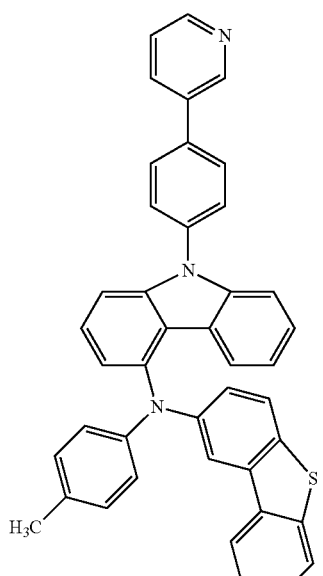
(A200)
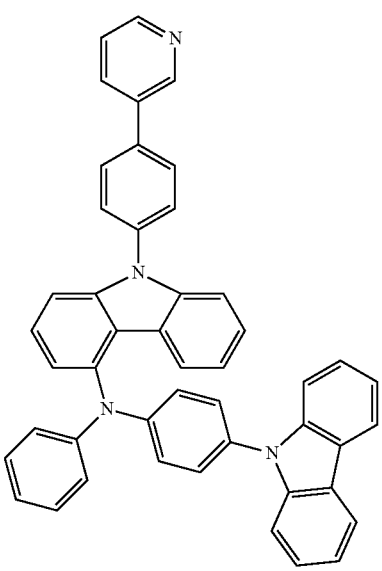
(A199)
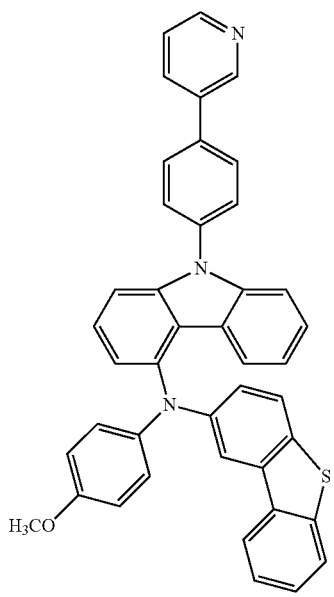
(A201)

-continued
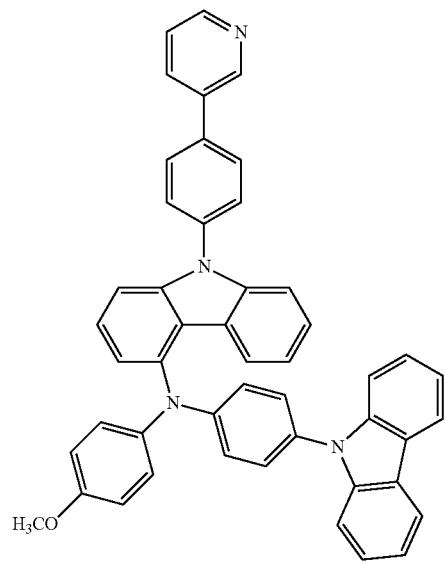
(A202)
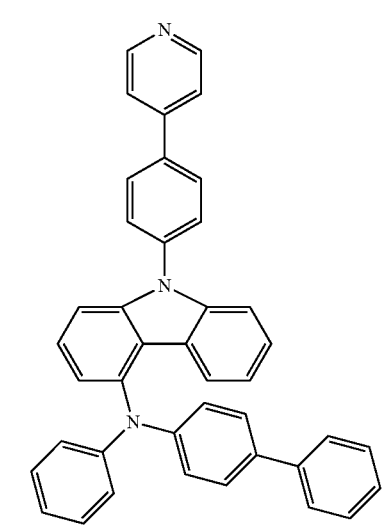
(A203)
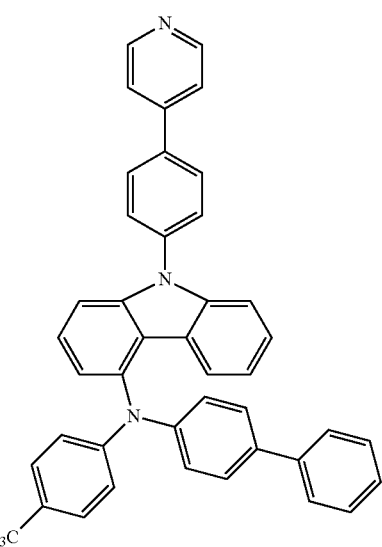
(A204)
-continued
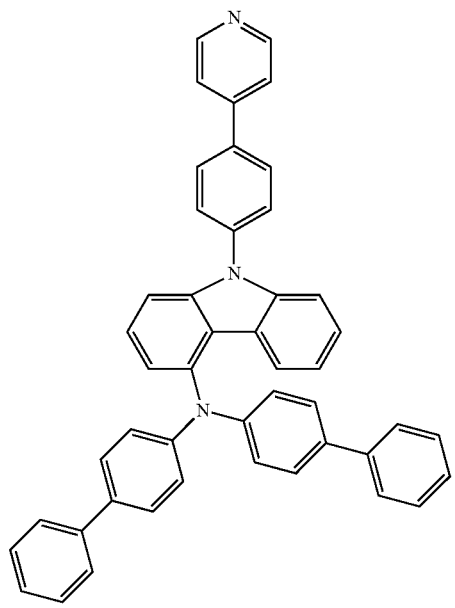
(A205)
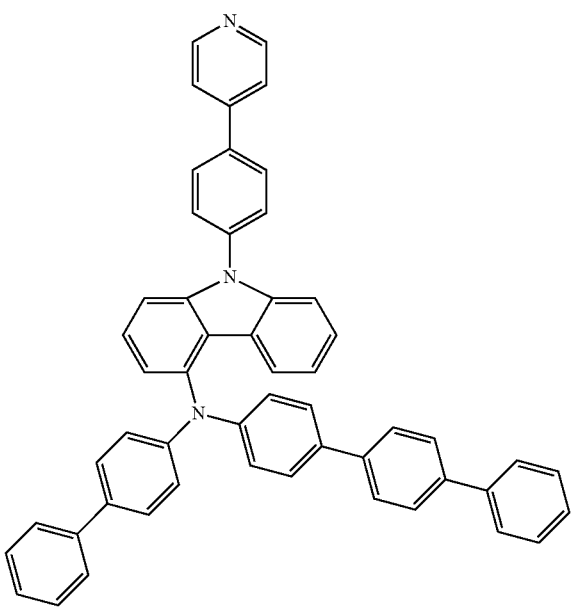
(A206)

-continued
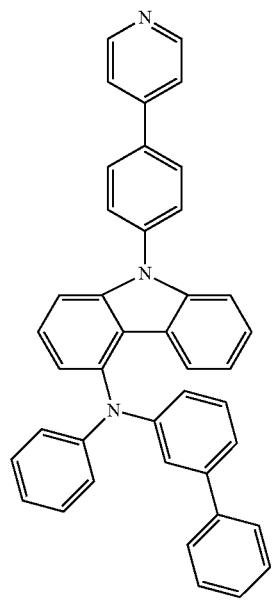
(A207)
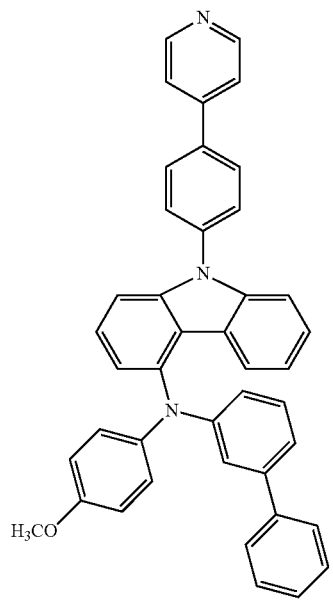
(A209)
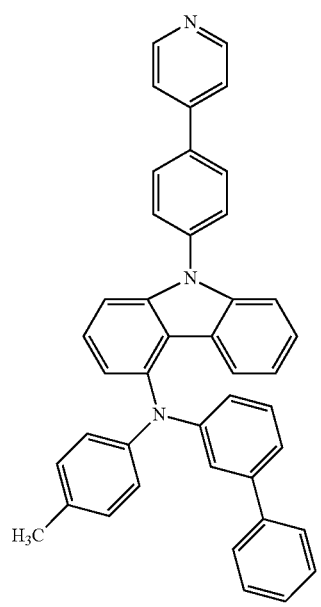
(A208)
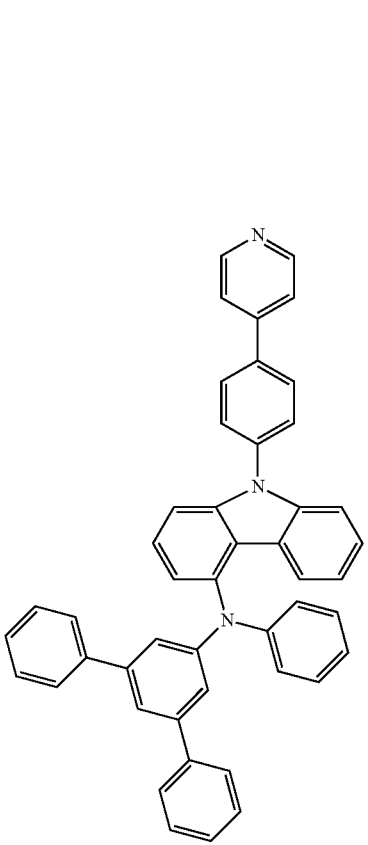
(A210)

99
100
(A211)
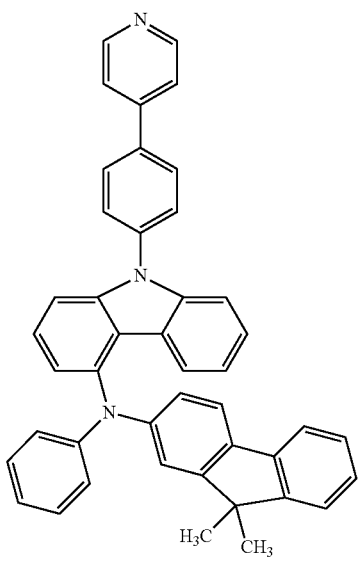
(A213)
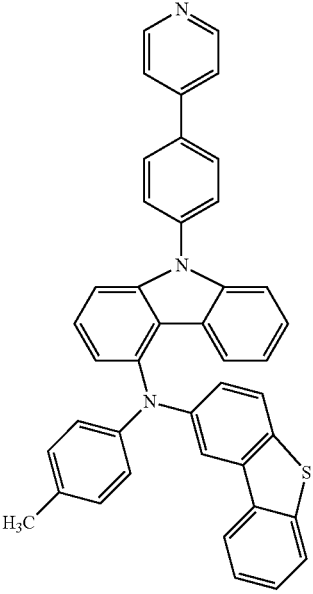
(A212)
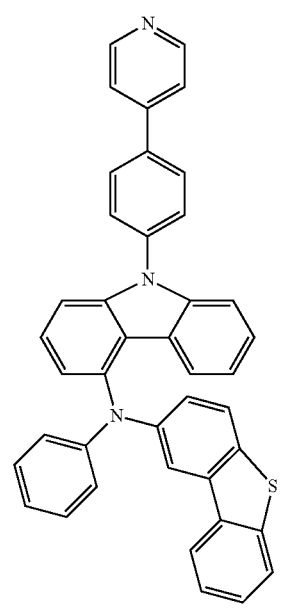
(A214)
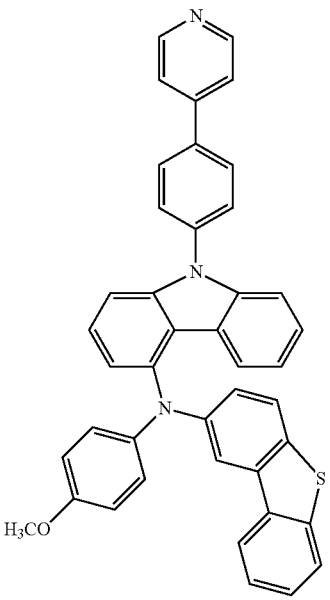

(A215)
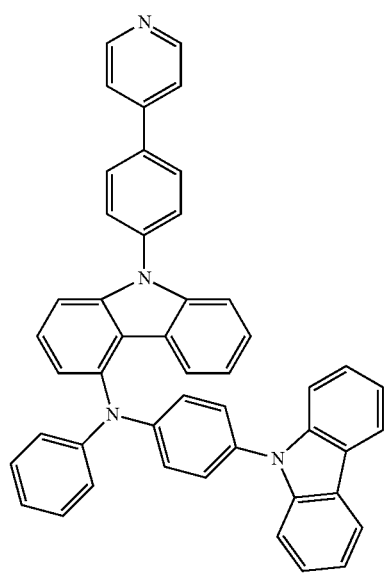
(A216)
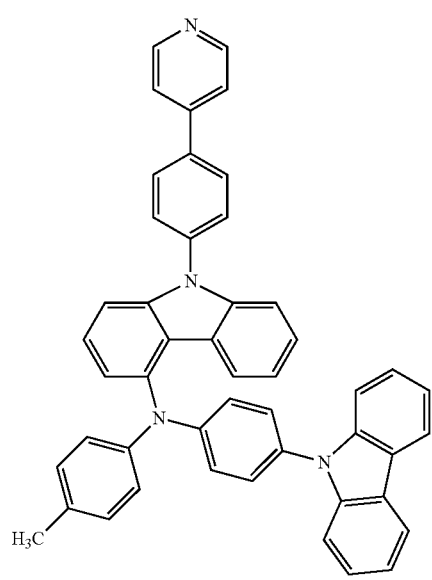
(A217)
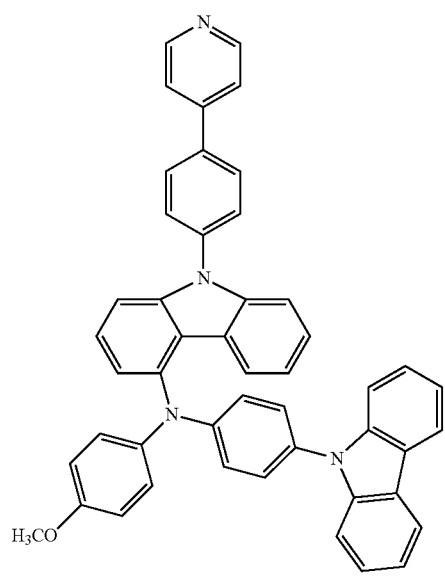
(A218)
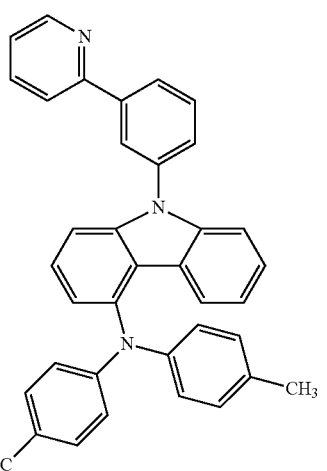
(A219)
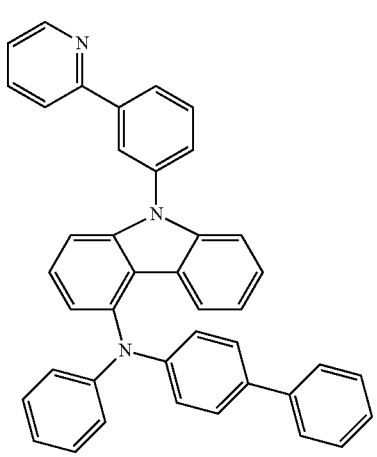

-continued
(A220)
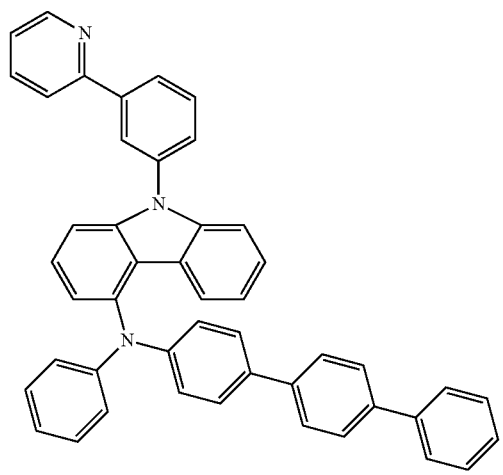
(A221)
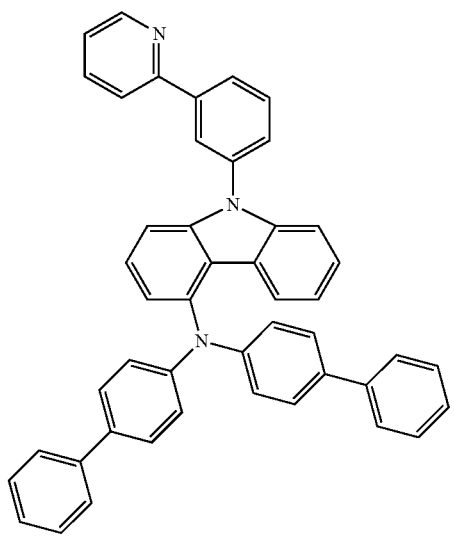
(A222)
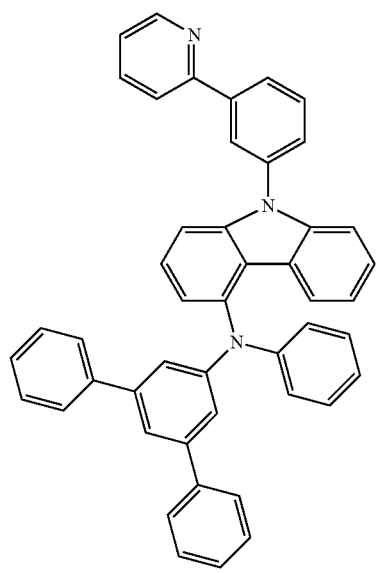
-continued
(A223)
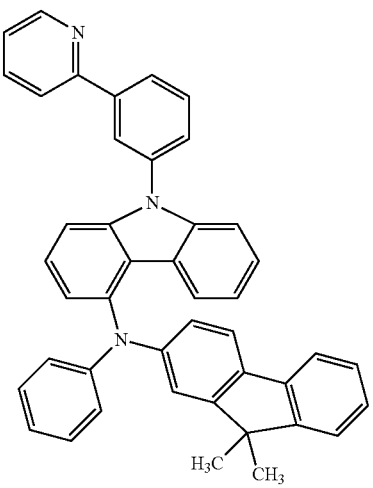
(A224)
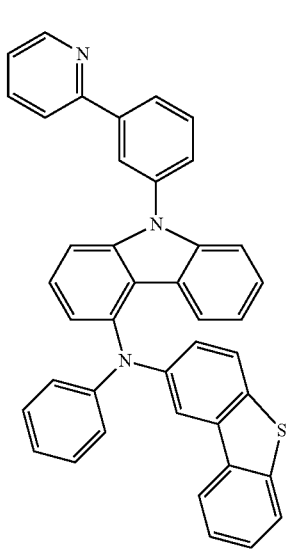
(A225)
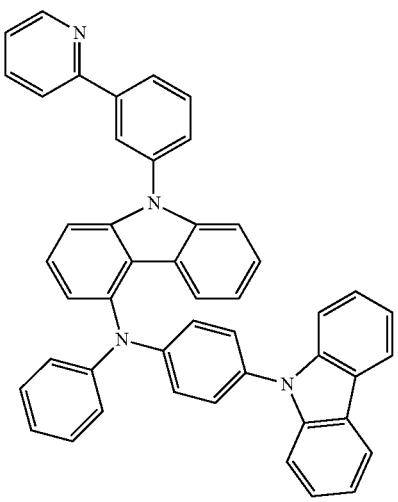

(A226)
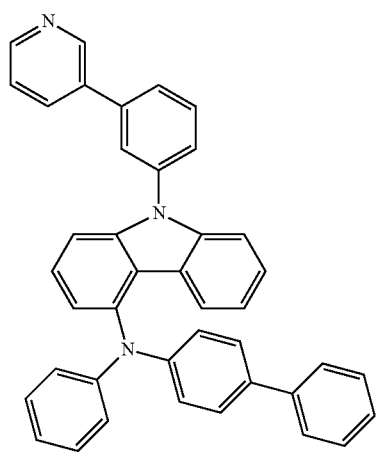
(A227)
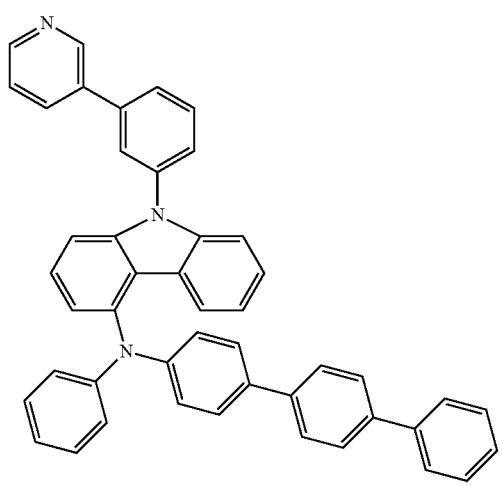
(A228)
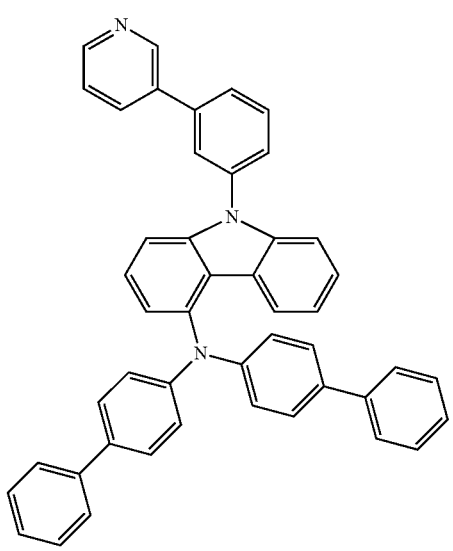
(A229)
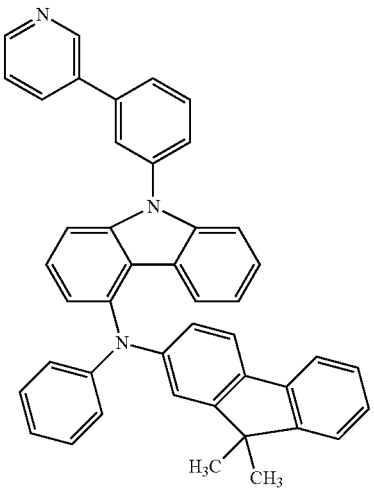
(A230)
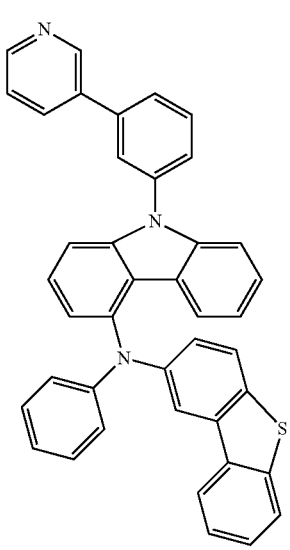
(A231)
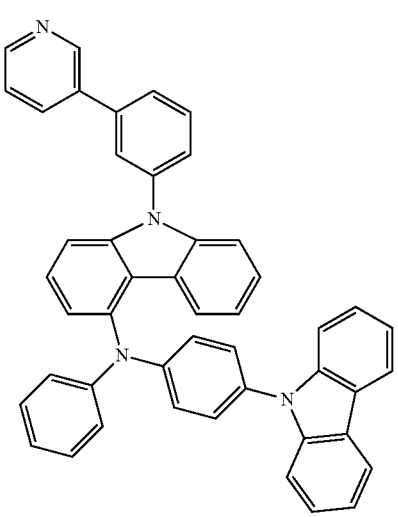

-continued
(A232)
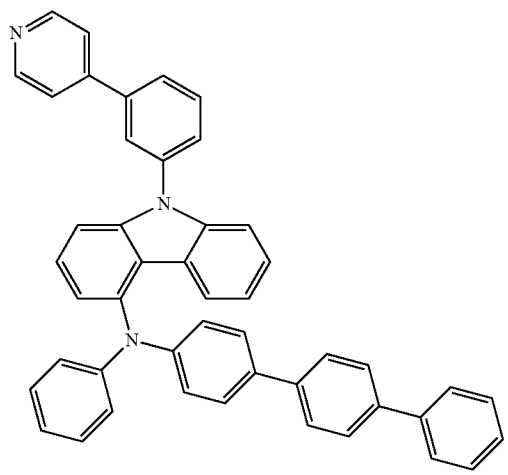
(A233)
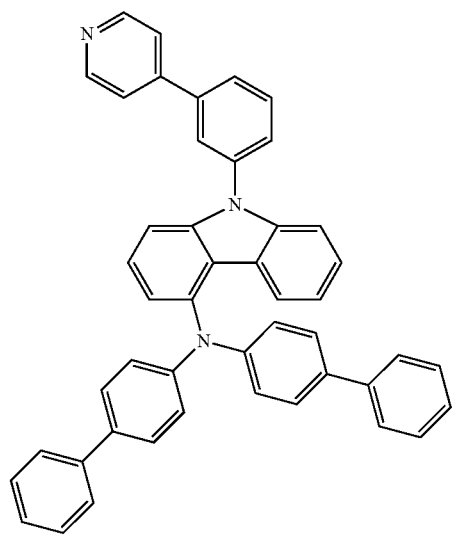
(A234)
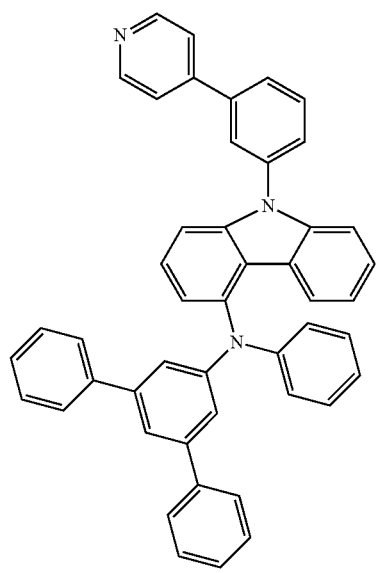
-continued
(A235)
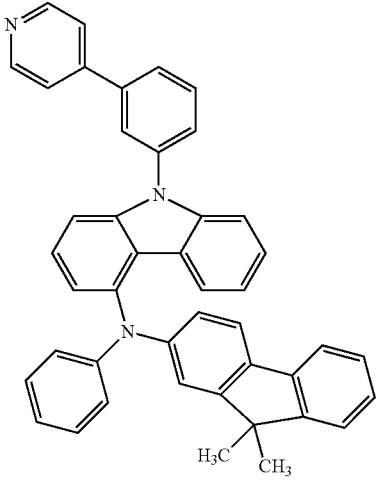
(A236)
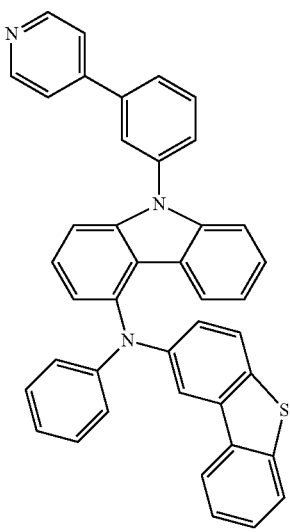
(A237)
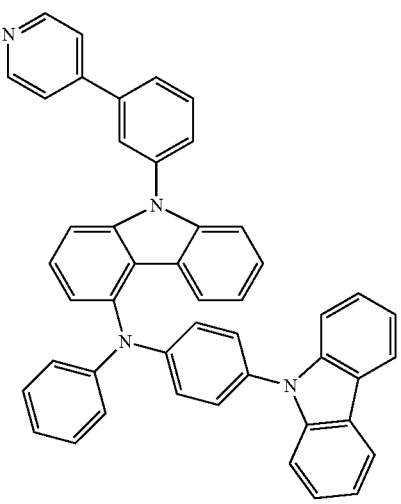

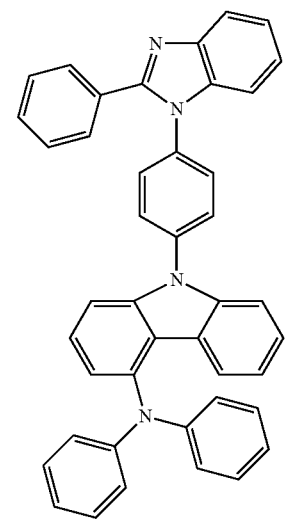
(A238)
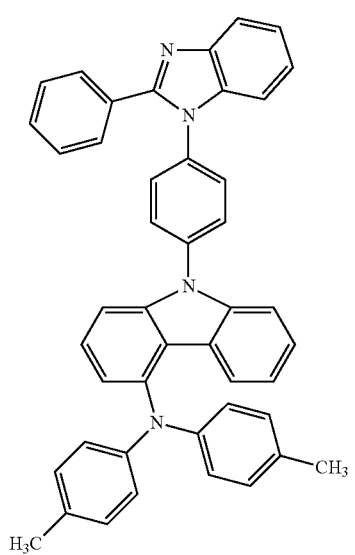
(A239)
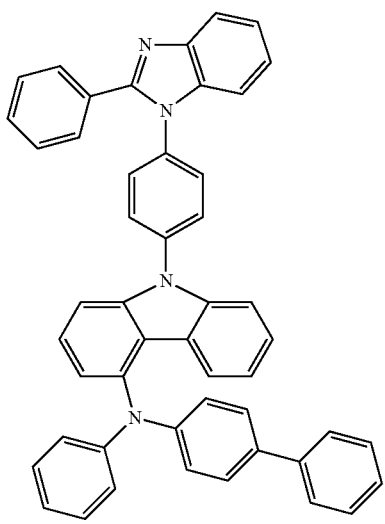
(A240)
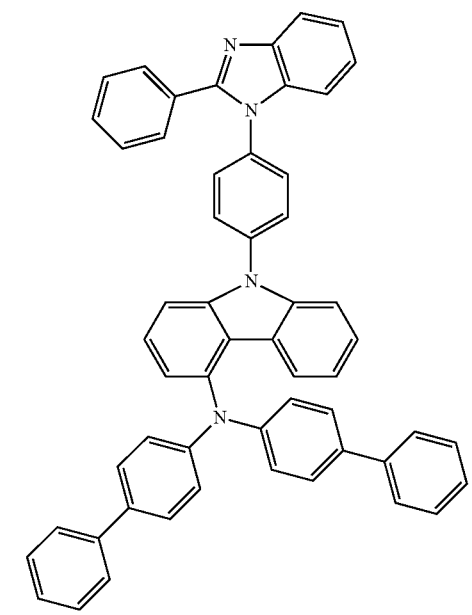
(A241)
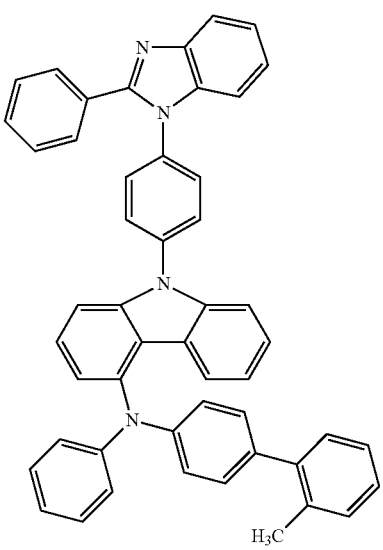
(A242)

(A243)
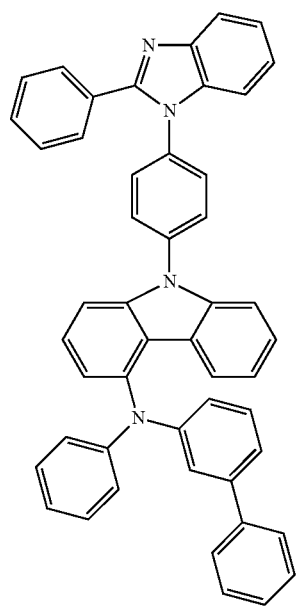
(A244)
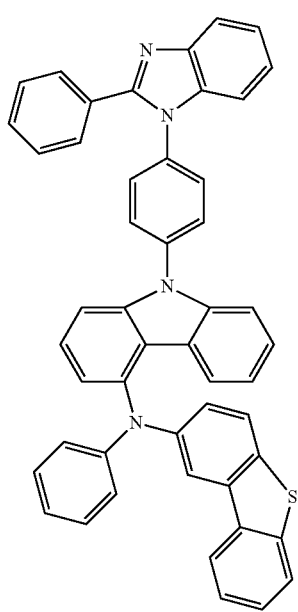
(A245)
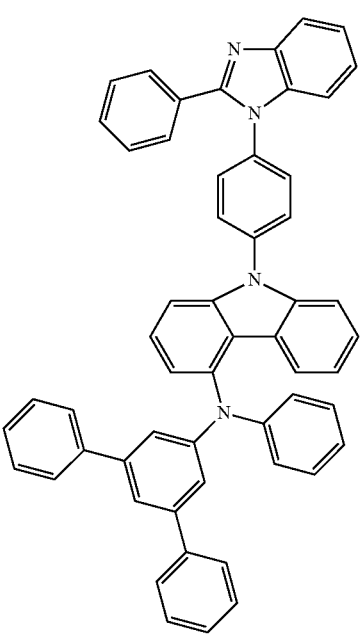
(A246)
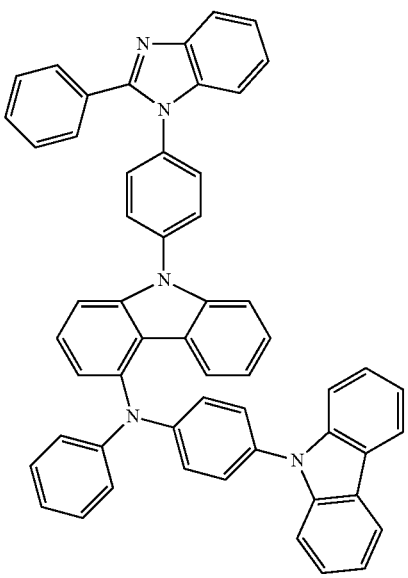

(A247)
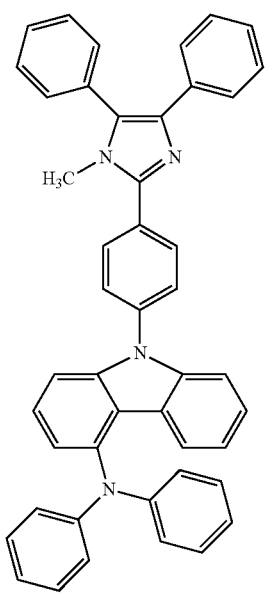
(A249)
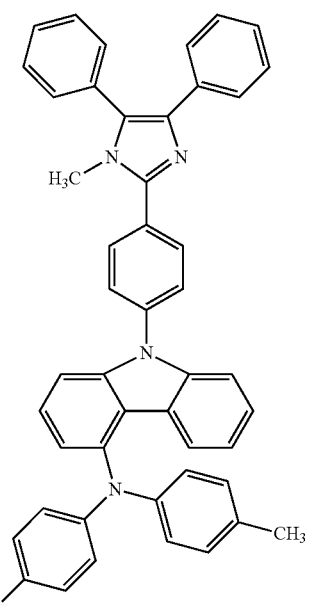
(A248)
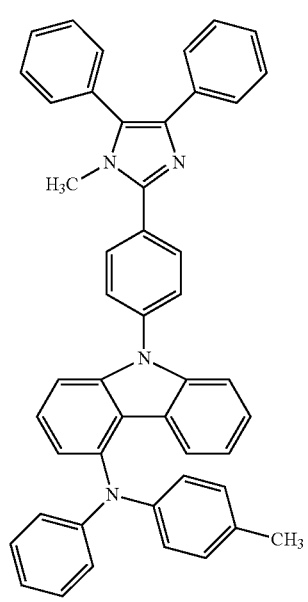
(A250)
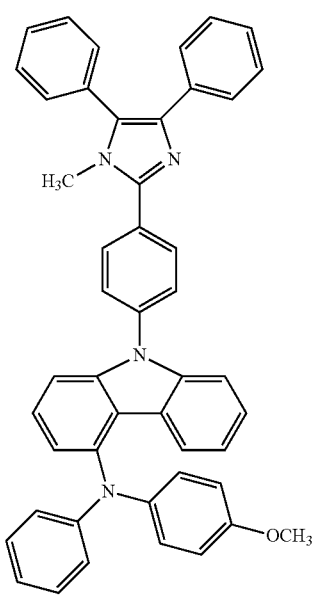

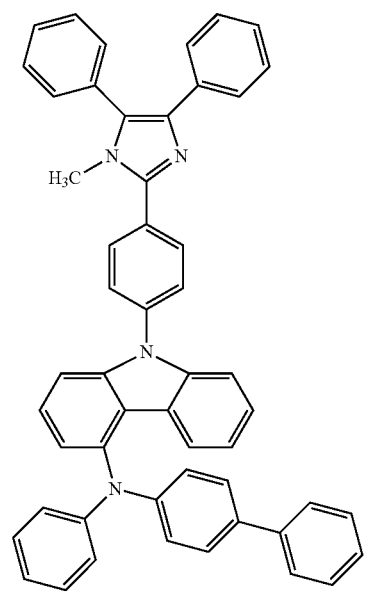 (A251)
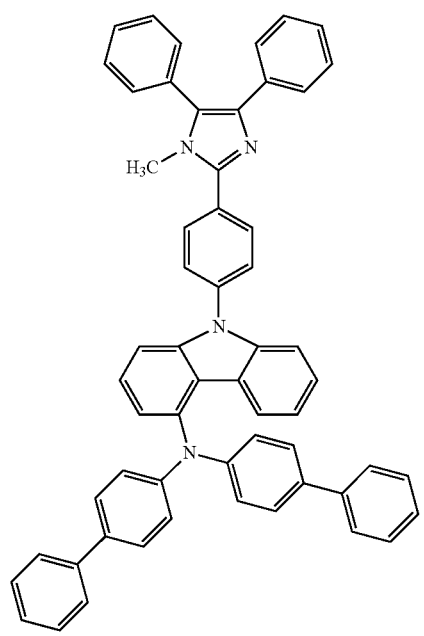 (A252)
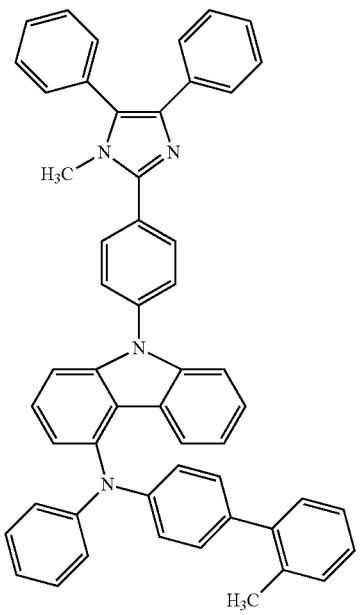 (A253)
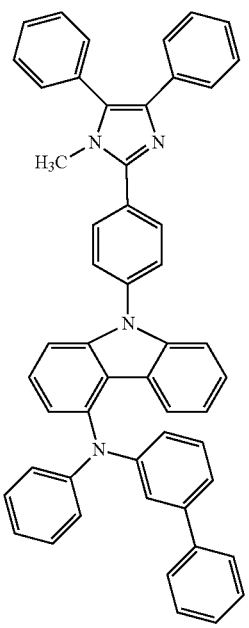 (A254)

-continued
(A255)
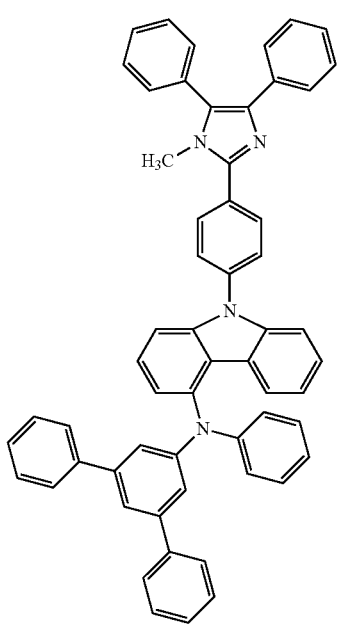
(A257)
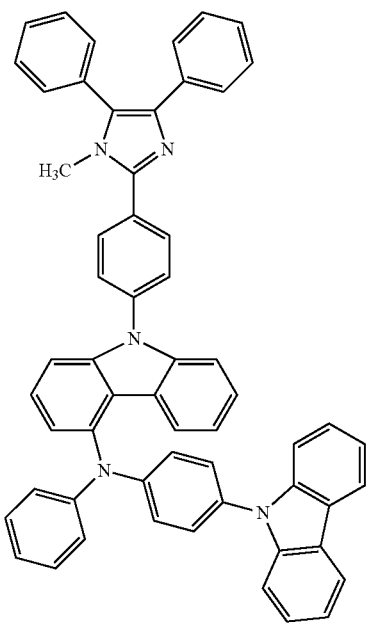
(A256)
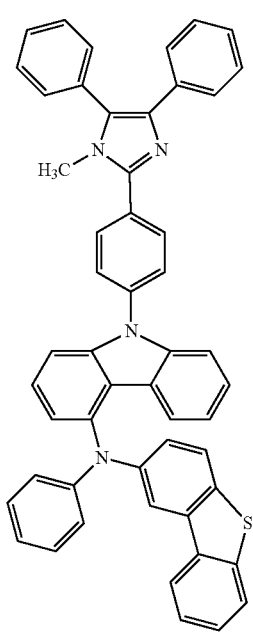
(A258)
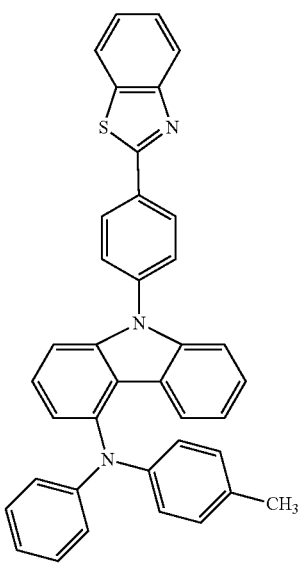

(A259)
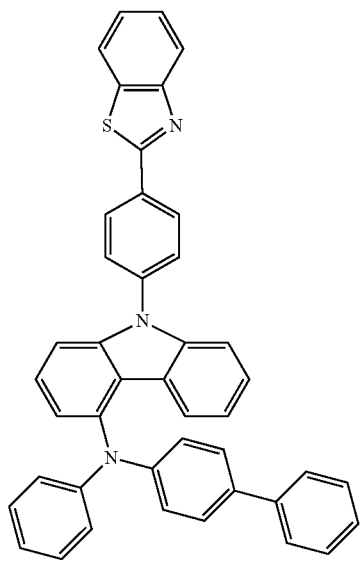
(A260)
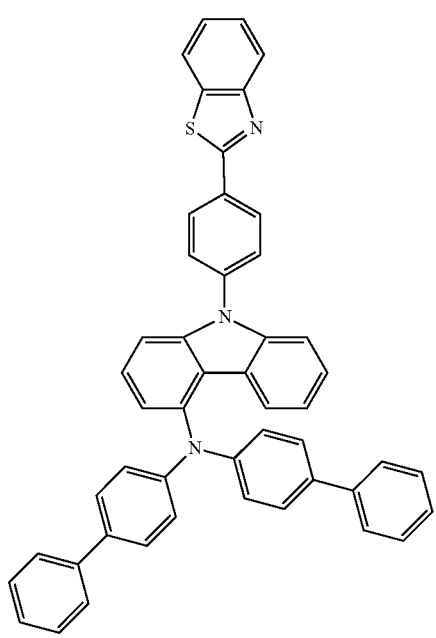
(A261)
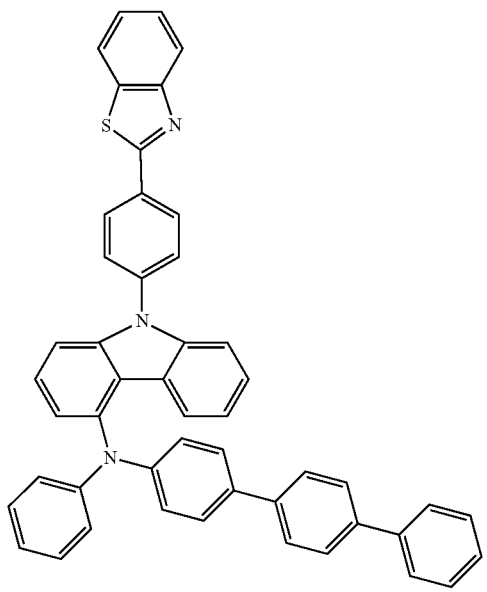
(A262)
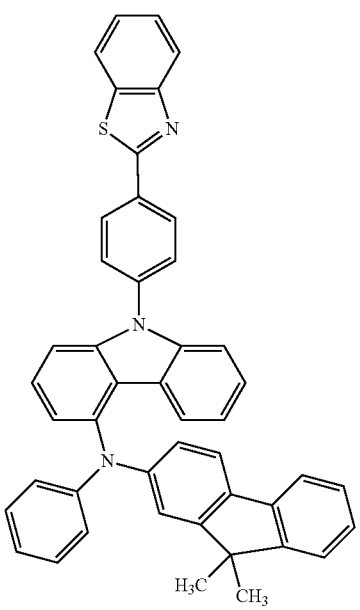

121
-continued
(A263)
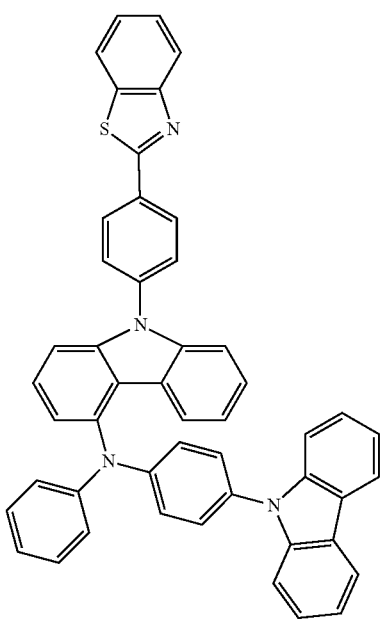
(A264)
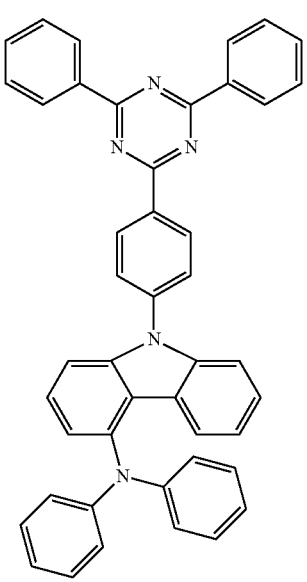
122
-continued
(A265)
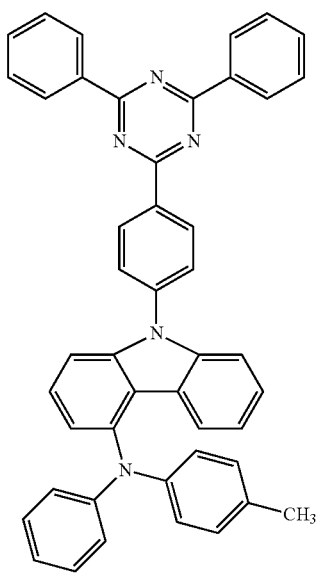
(A266)

-continued
(A267)
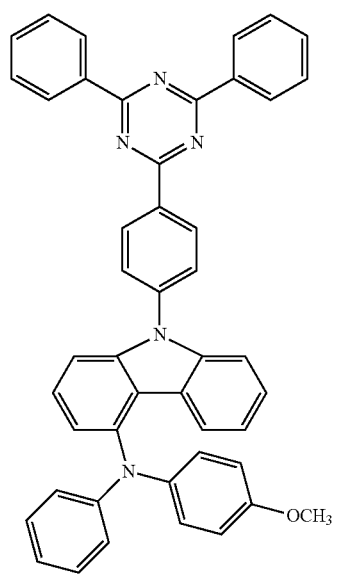
(A269)
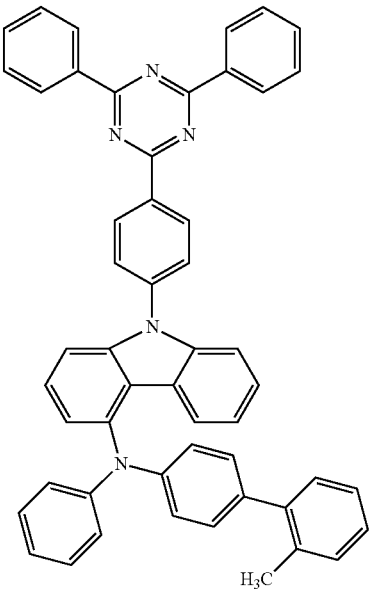
(A268)
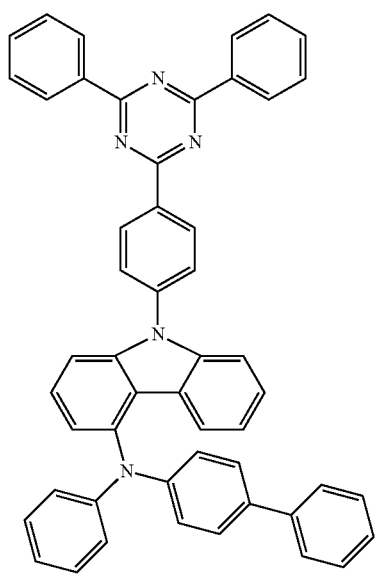
(A270)
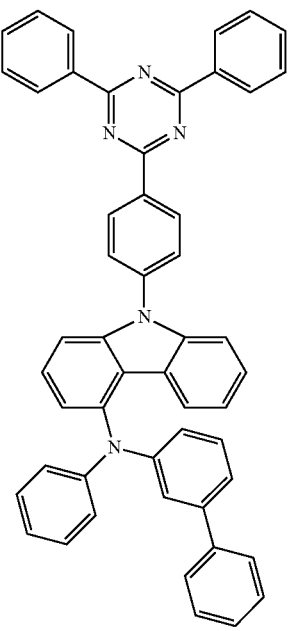

(A271)
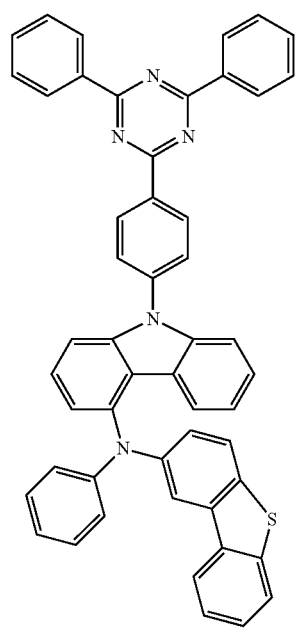
(A273)
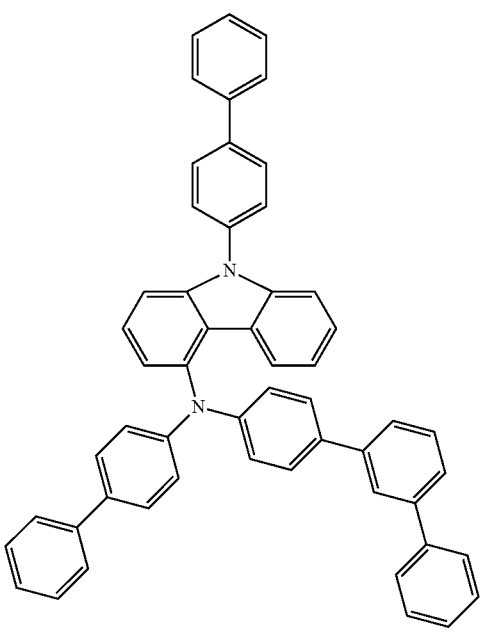
(A272)
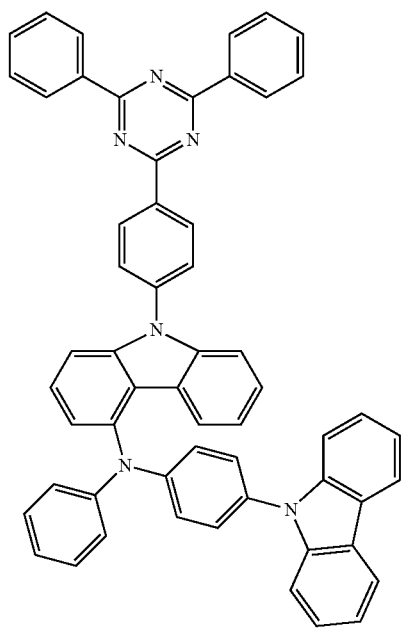
(A274)
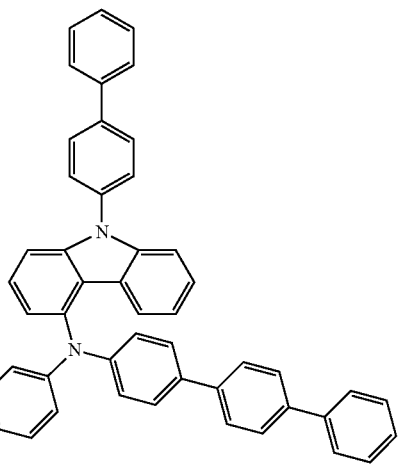

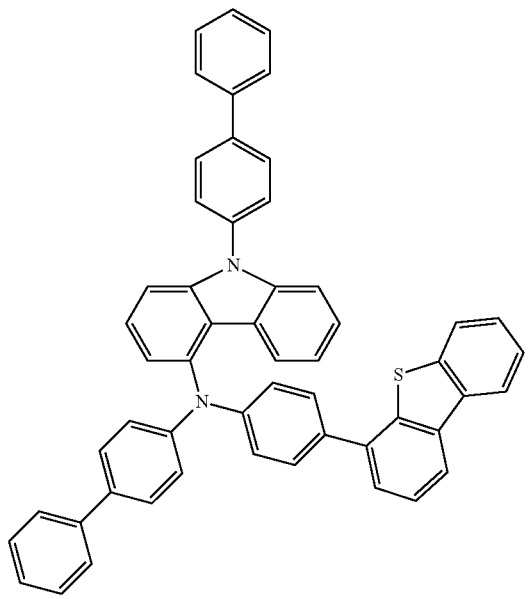
(A275)
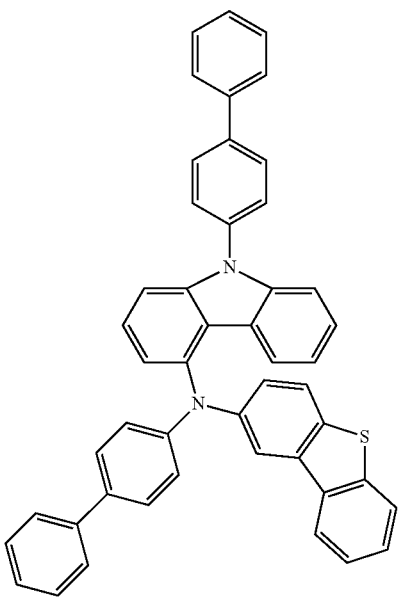
(A277)
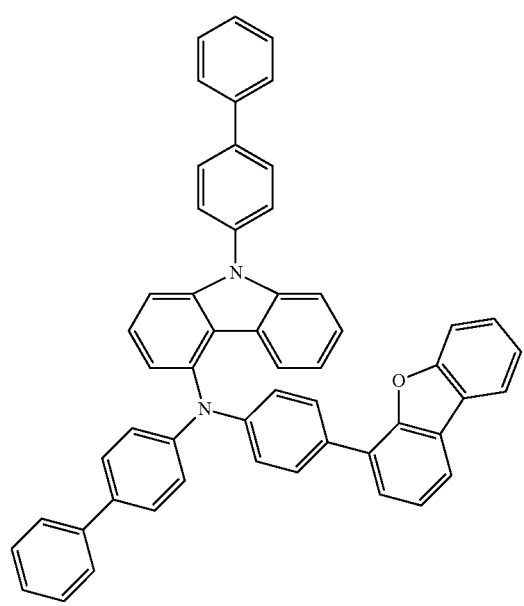
(A276)
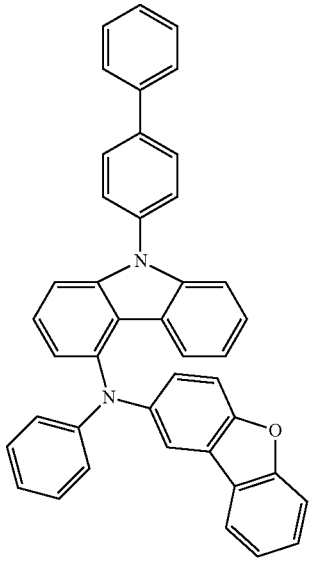
(A278)

(A279)
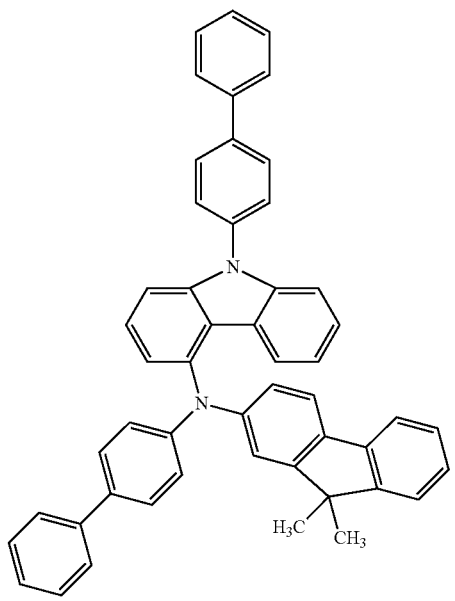
(A280)
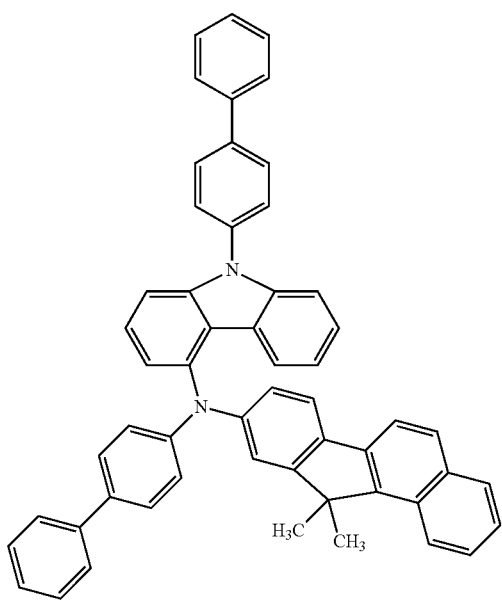
(A281)
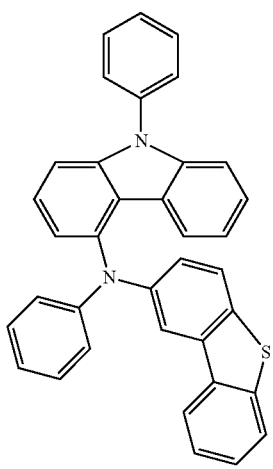
(A282)
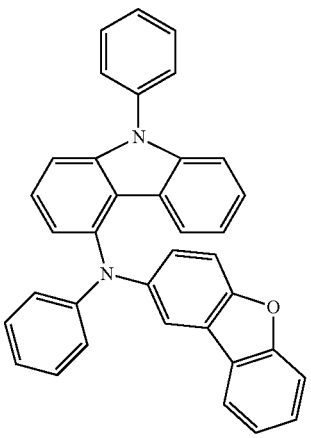
(A283)
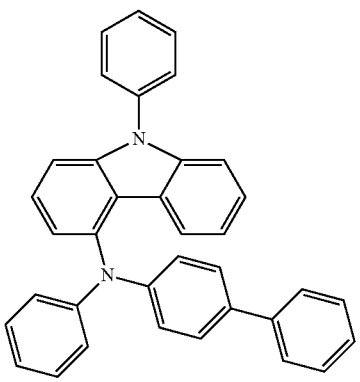

(A284)
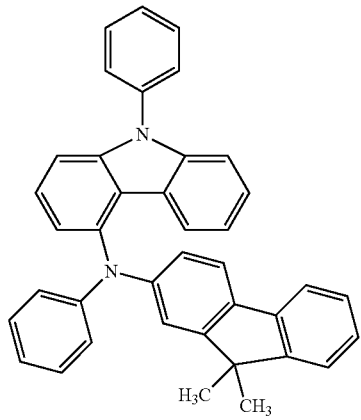
(A287)
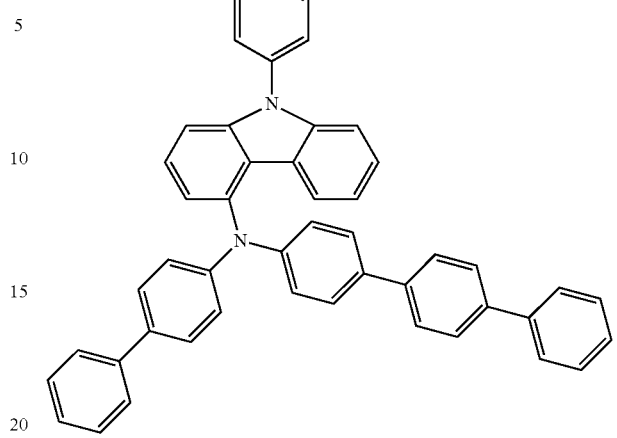
(A285)
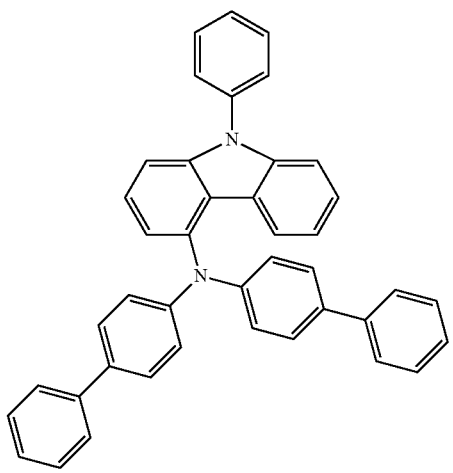
(A288)
(A286)
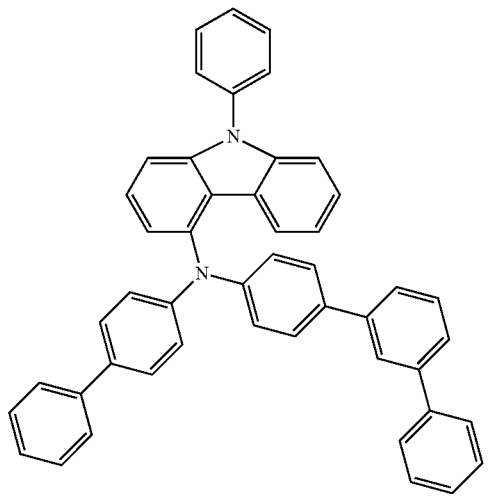
(A289)
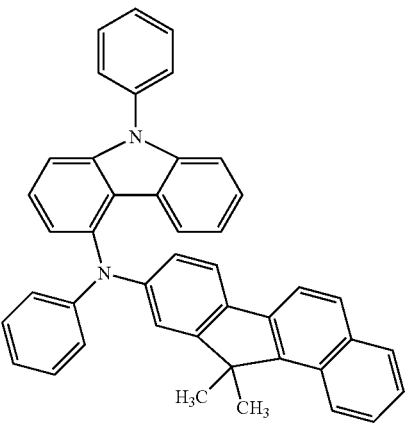

(A290)
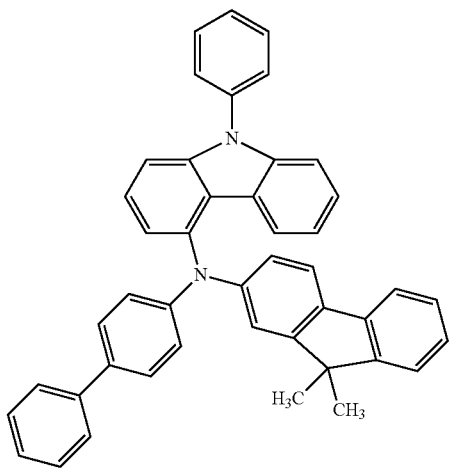
(A291)
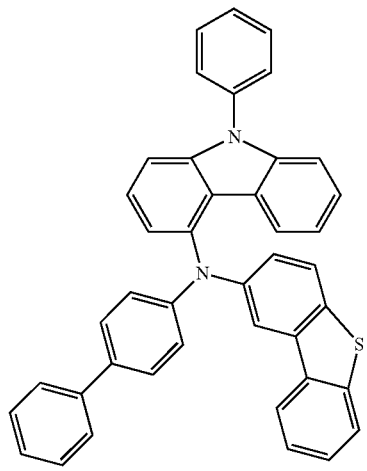
(A292)
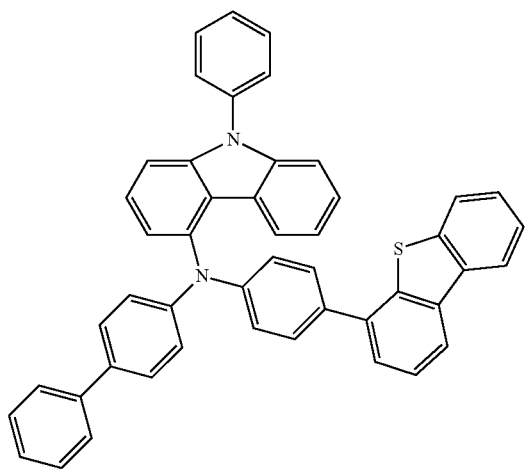
(A293)
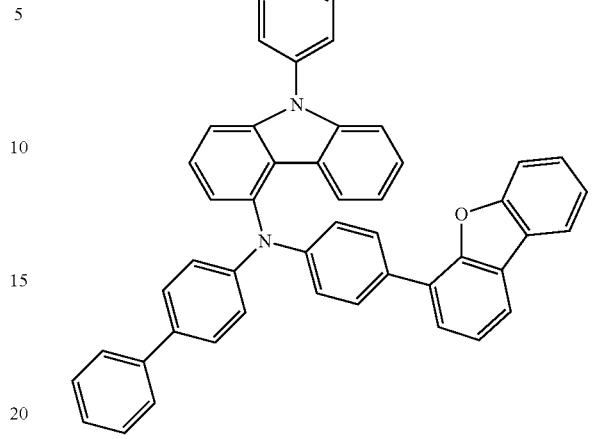
(A294)
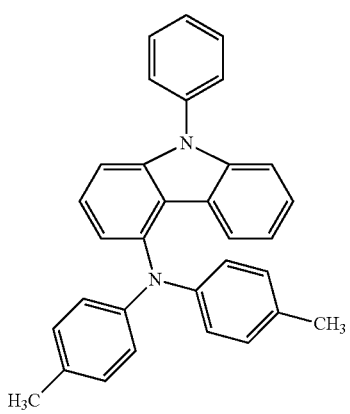
(A295)
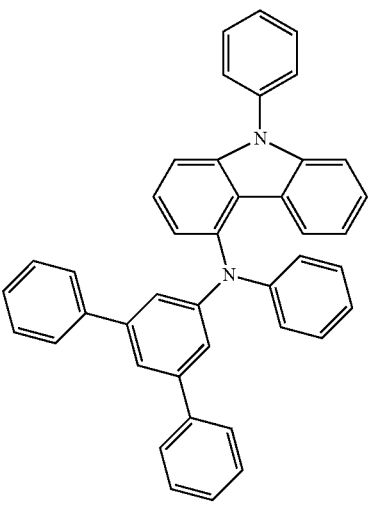

(A296)
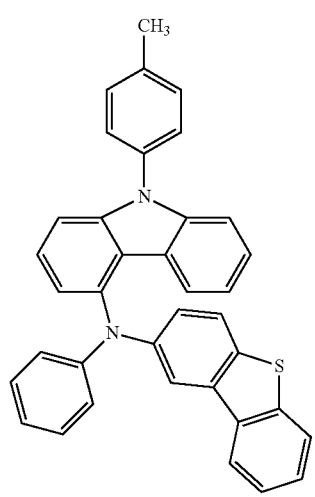
(A299)
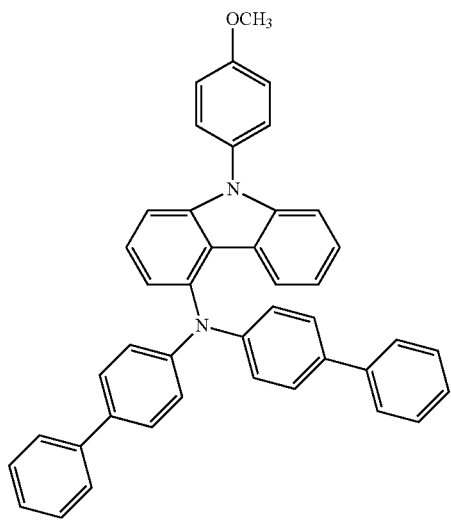
(A297)
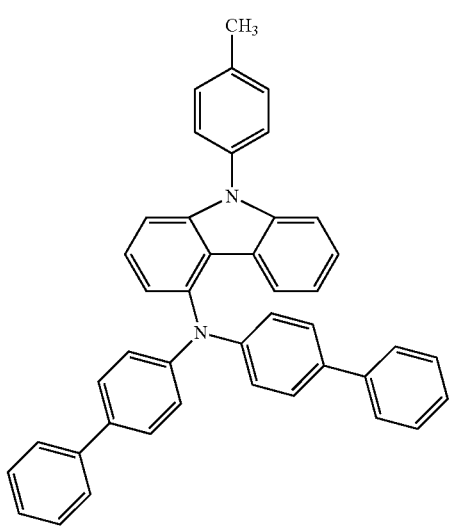
(A300)
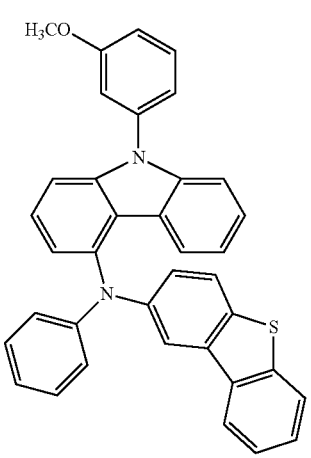
(A298)
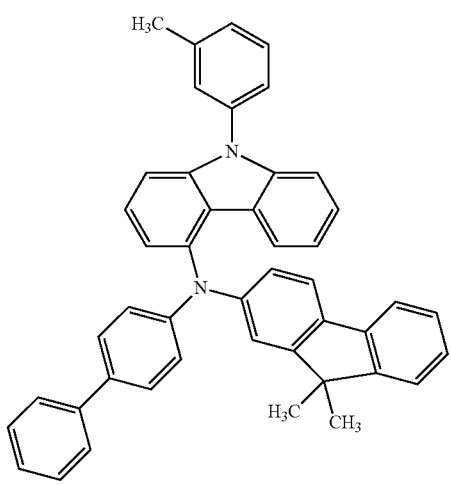
(A301)
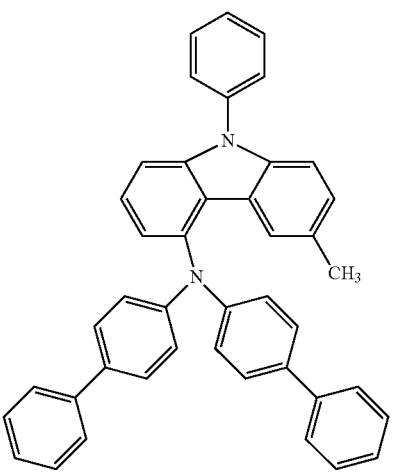

(A302)
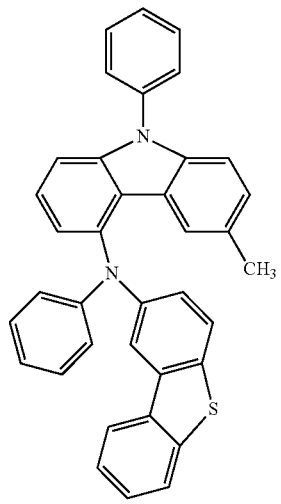
(A305)
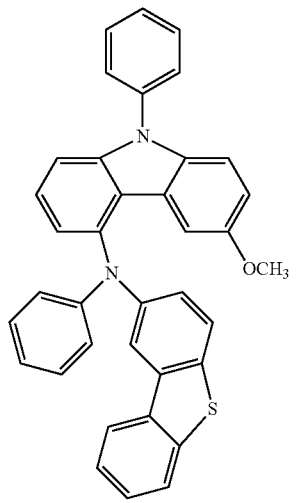
(A303)
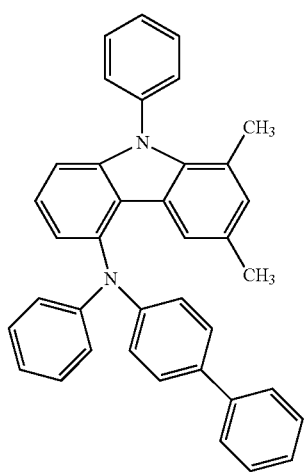
(A306)
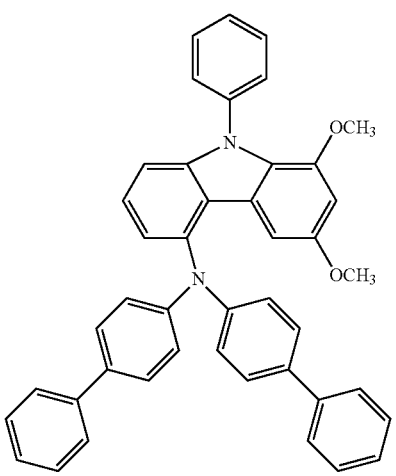
(A304)
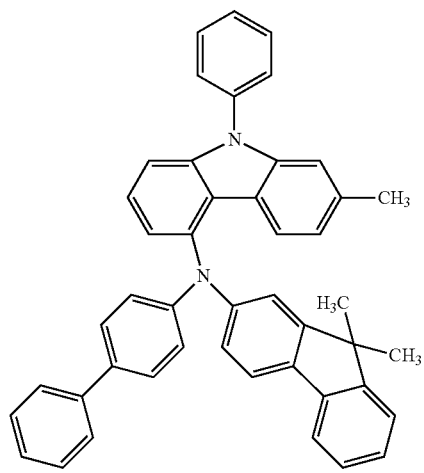
(A307)
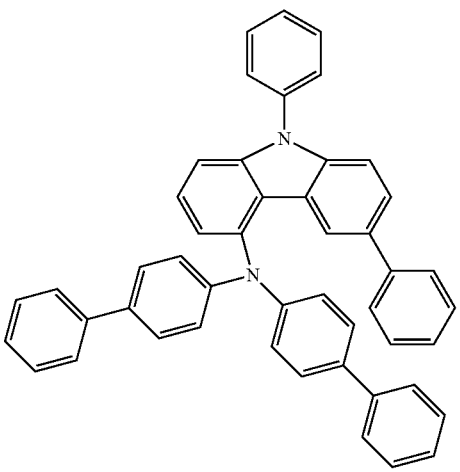

(A308)
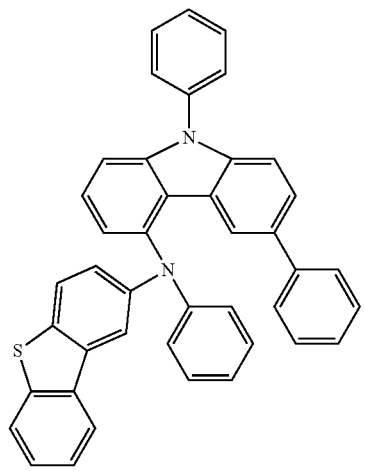
(A309)
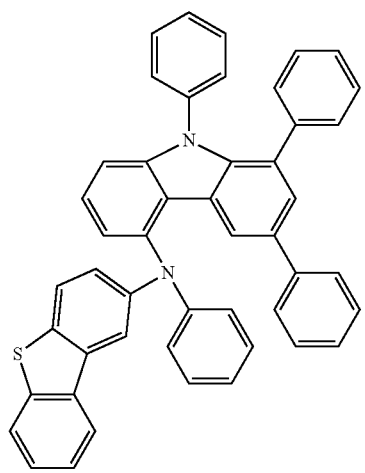
(A310)
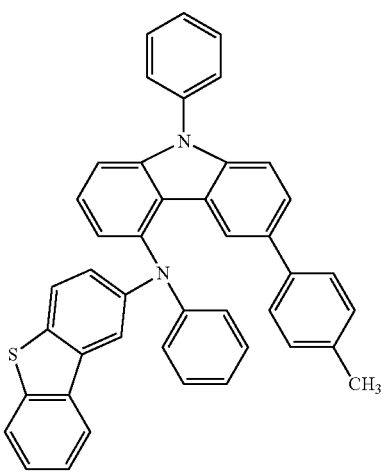
(A311)
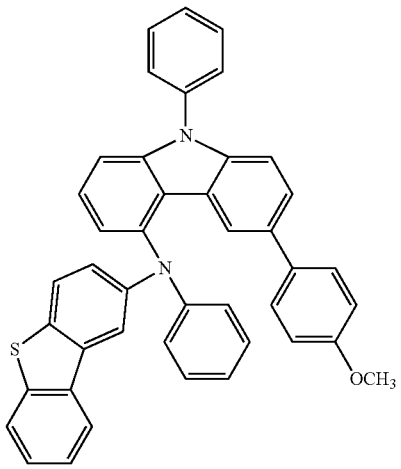
(A312)
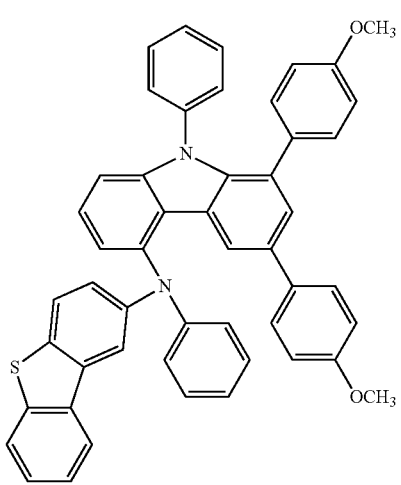
(A313)
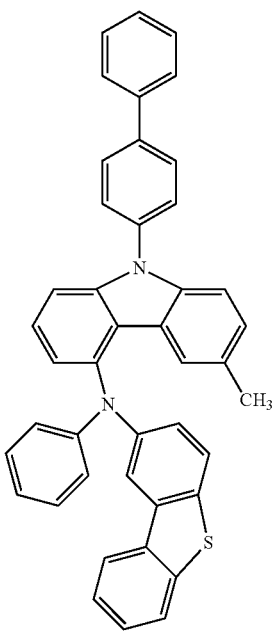

(A314)
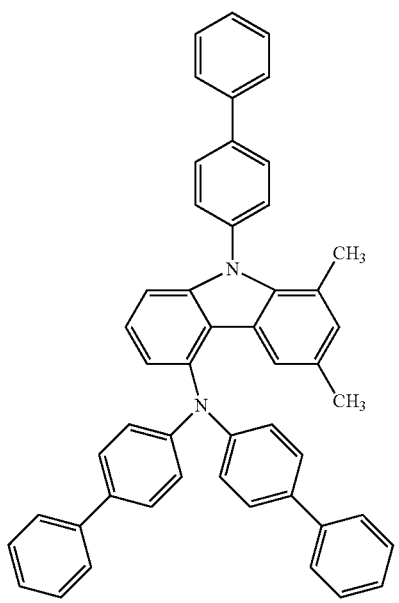
(A315)
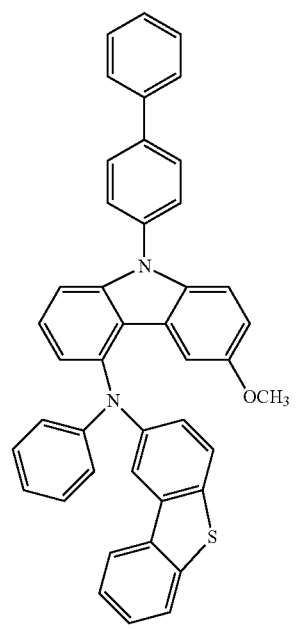
(A316)
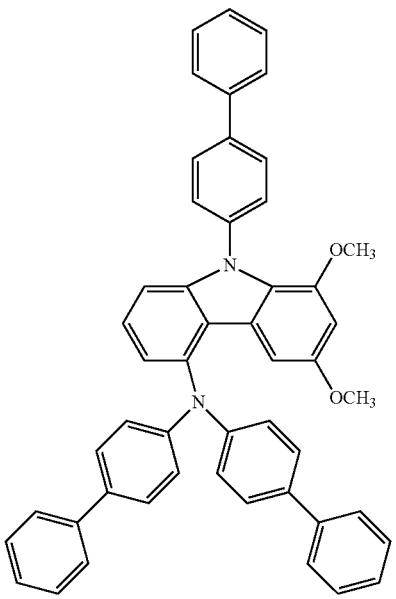
(A317)
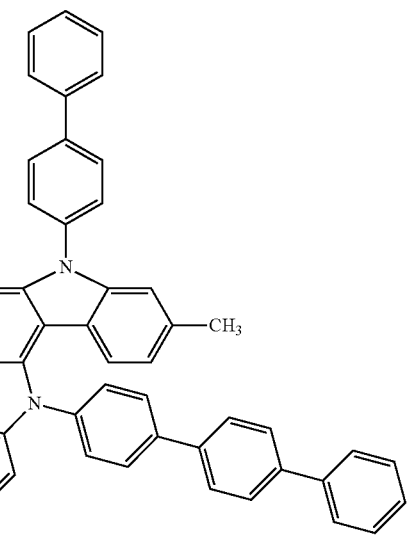

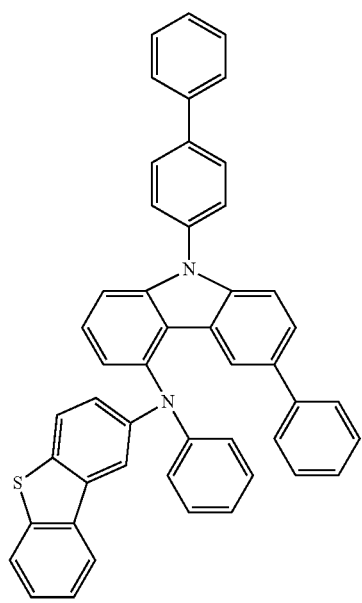
(A318)
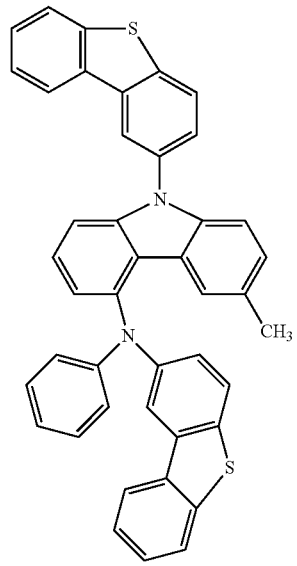
(A320)
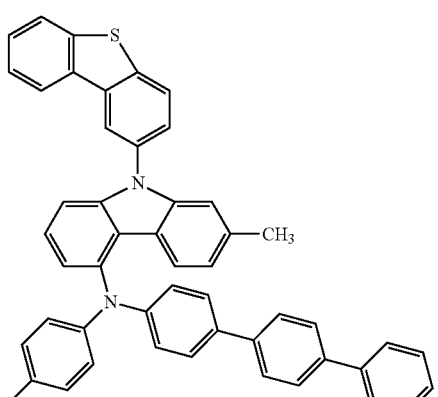
(A321)
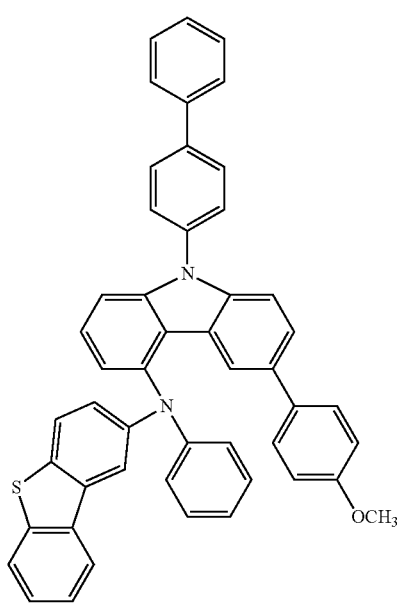
(A319)
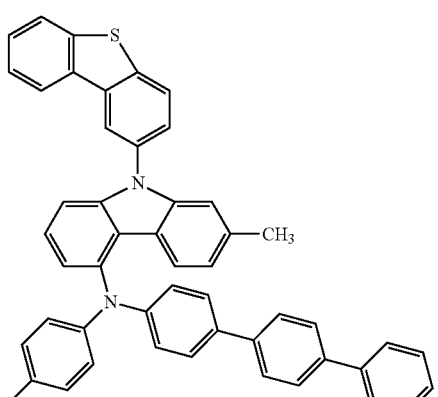
(A322)

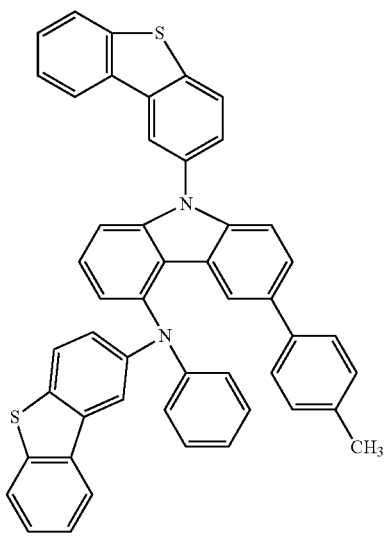
(A323)
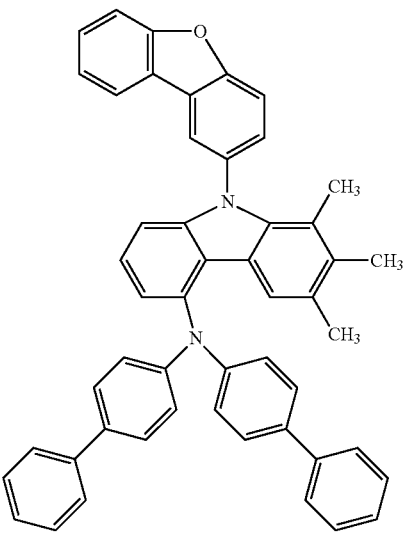
(A326)
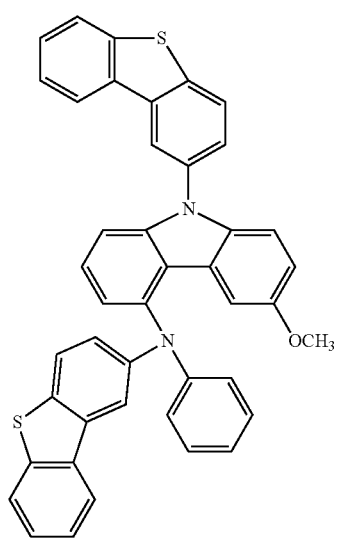
(A324)
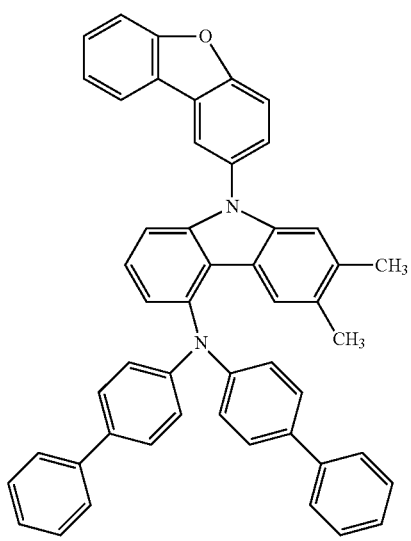
(A325)
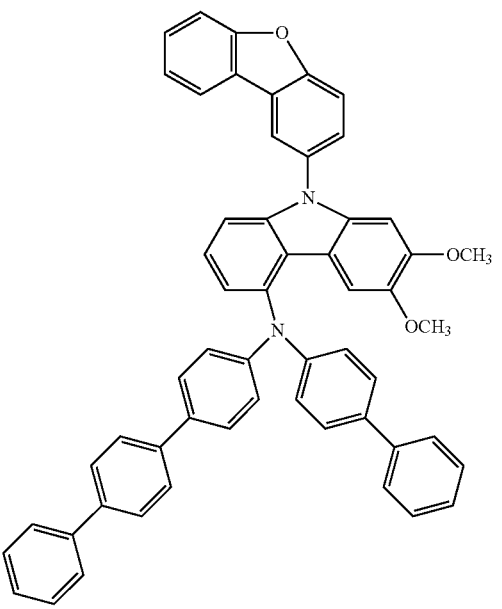
(A327)

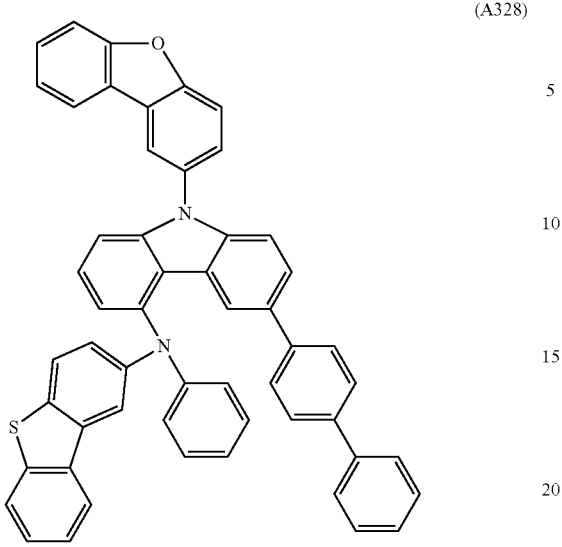
(A328)
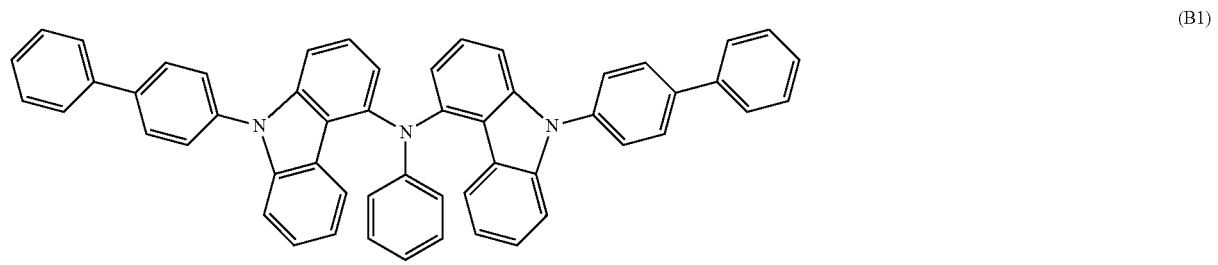
(B1)
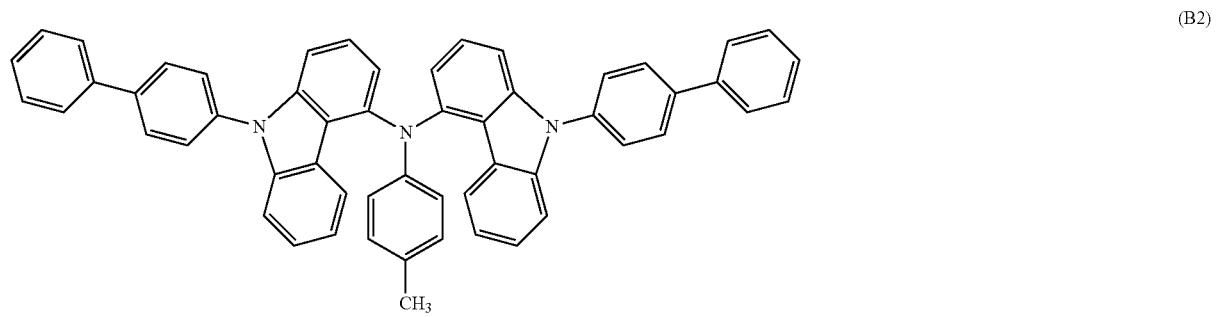
(B2)
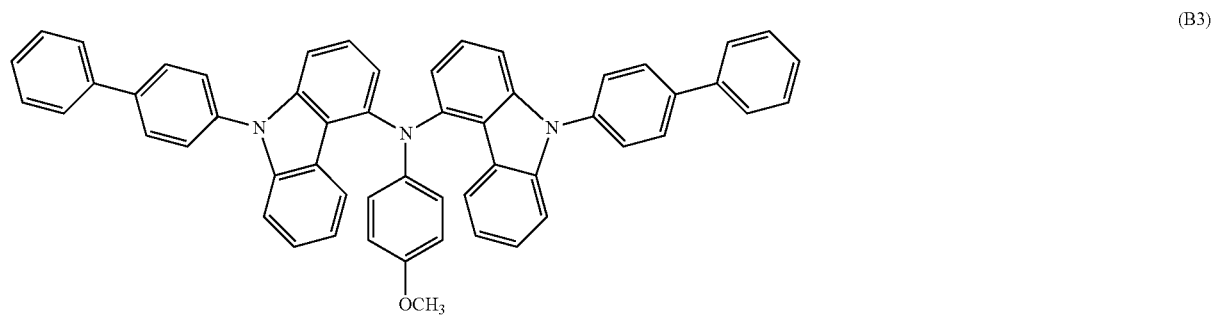
(B3)

-continued
(B4) 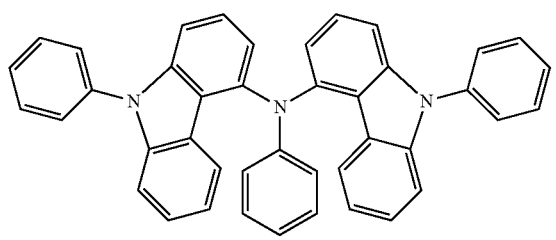
(B5) 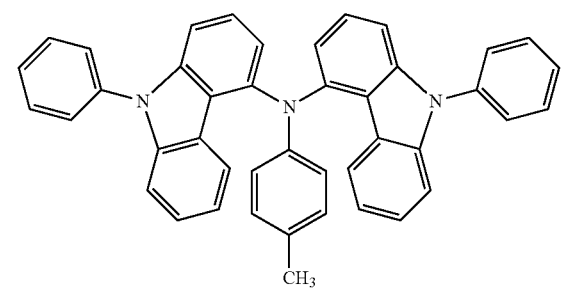
(B6) 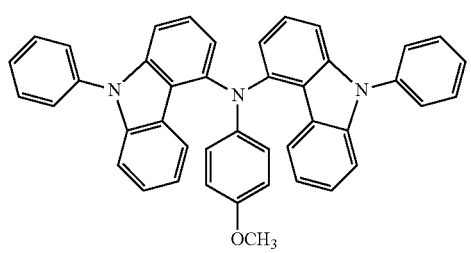
(B7) 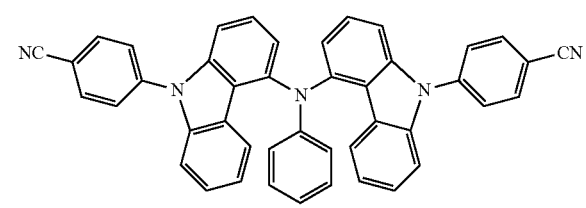
(B8) 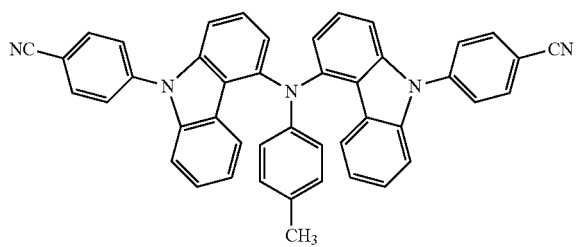
(B9) 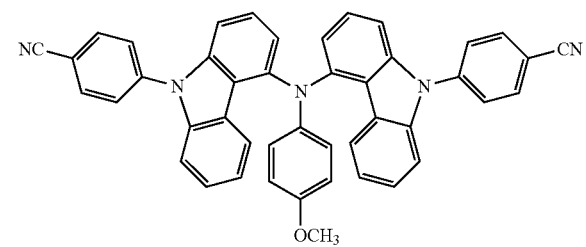
(B10) 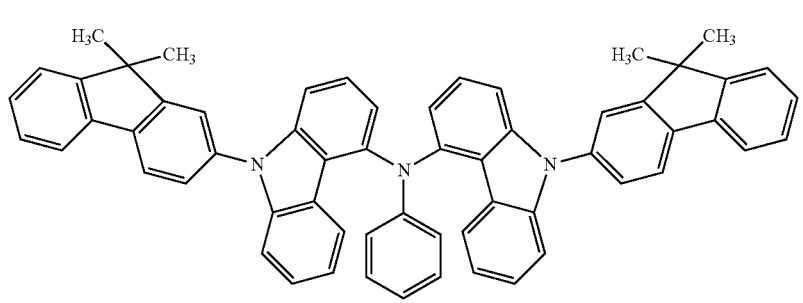
(B11) 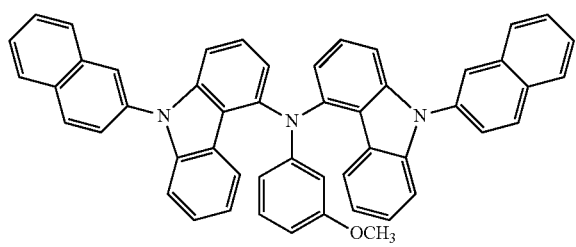
(B12) 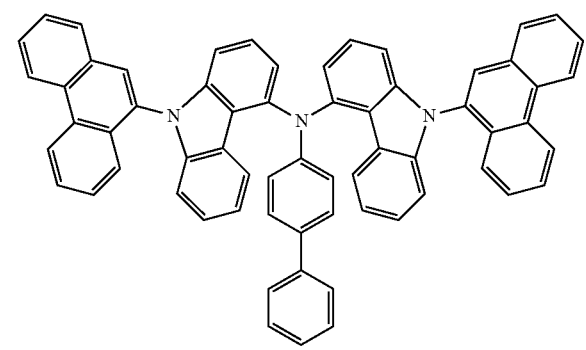

(B13)
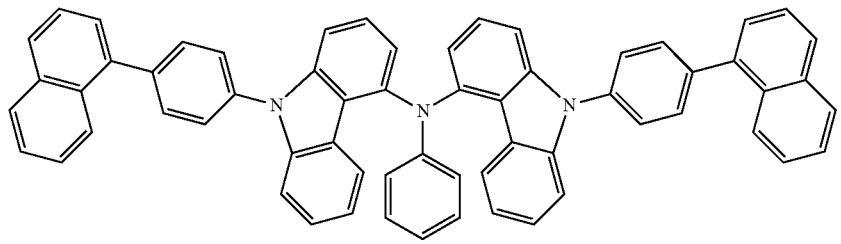
(B14)
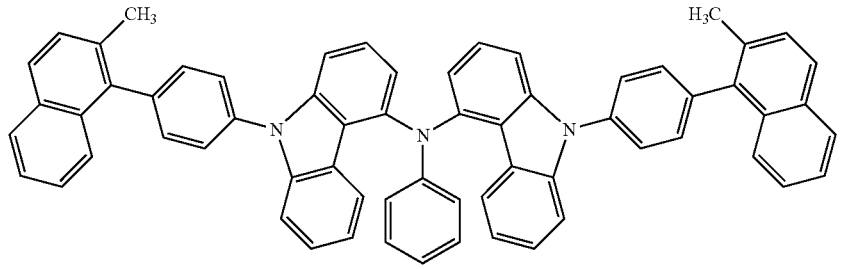
(B15)
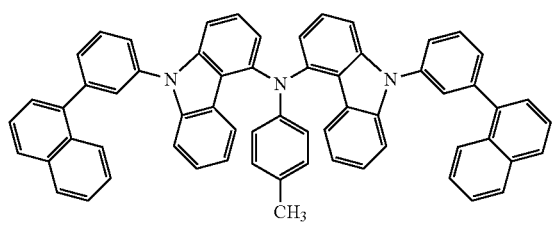
(B16)
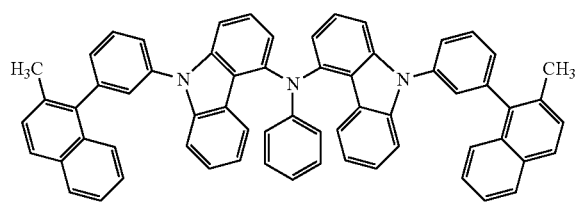
(B17)
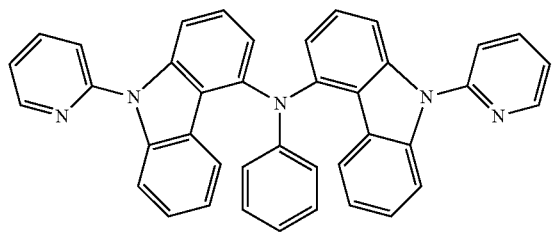
(B18)
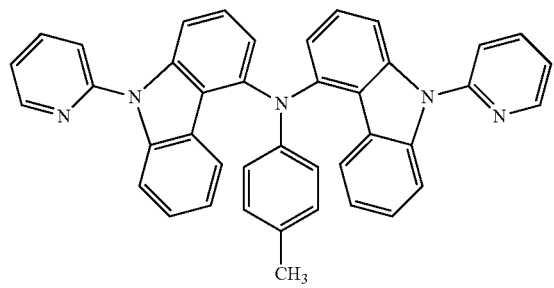
(B19)
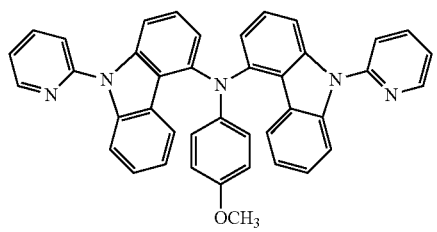
(B20)
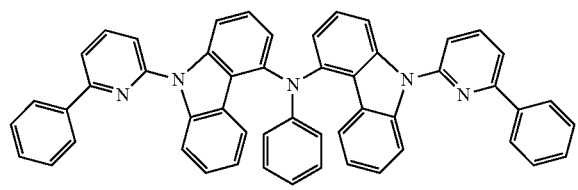
(B21)
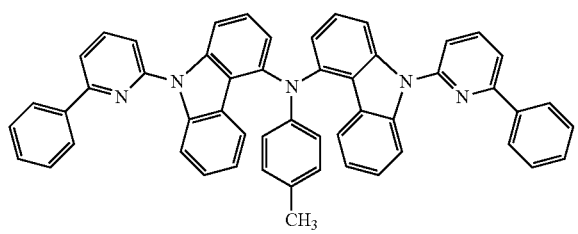
(B22)
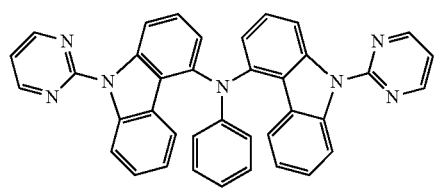

(B23) 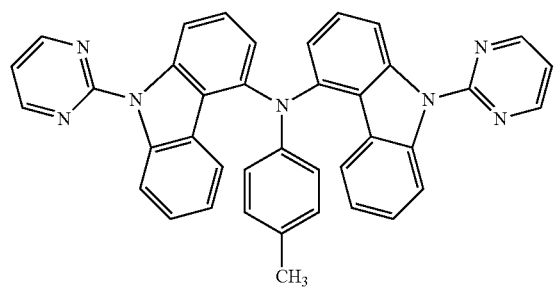
(B24) 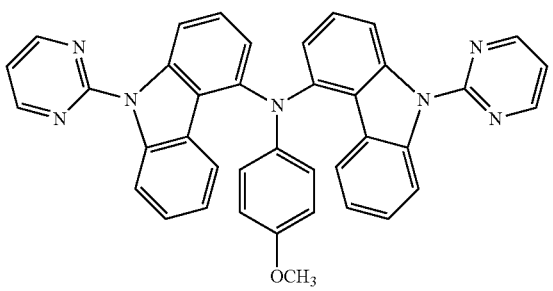
(B25) 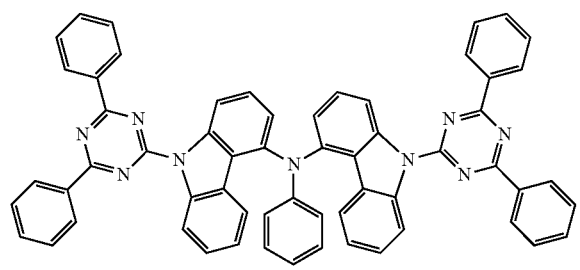
(B26) 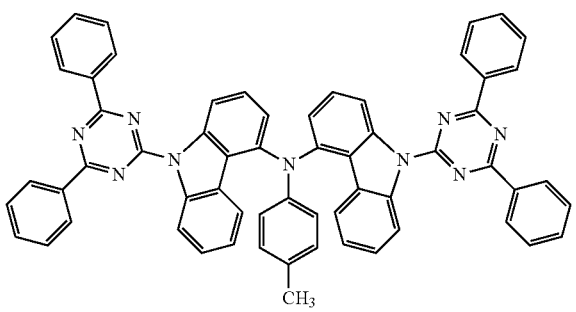
(B27) 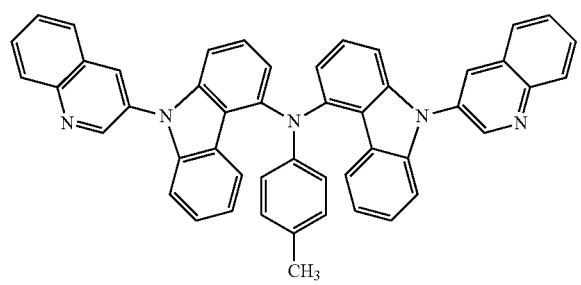
(B28) 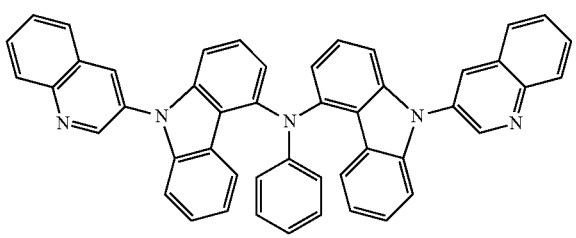
(B29) 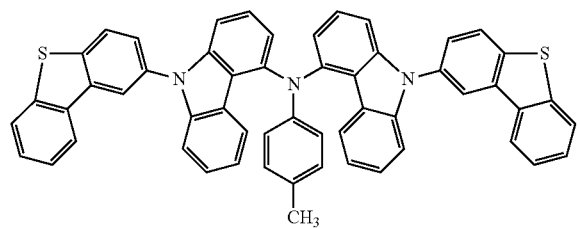
(B30) 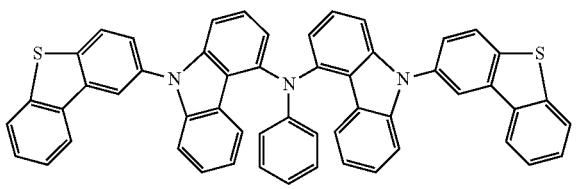
(B31) 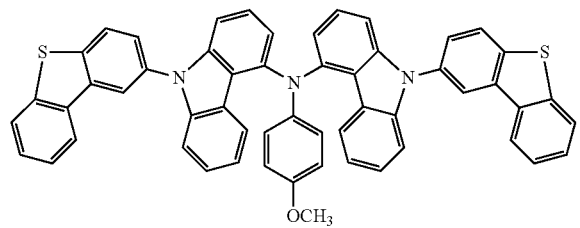
(B32) 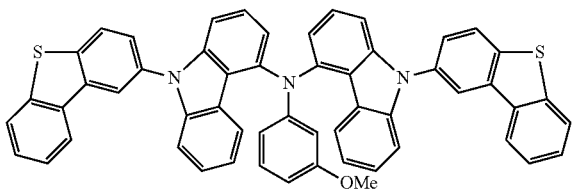

-continued
(B33)
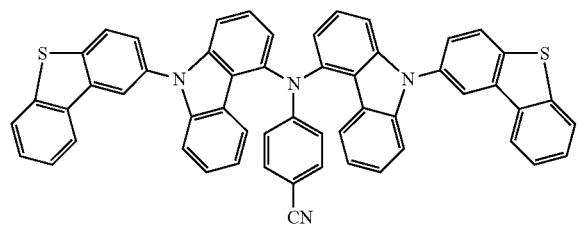
(B34)
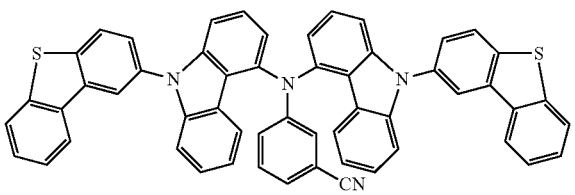
(B35)
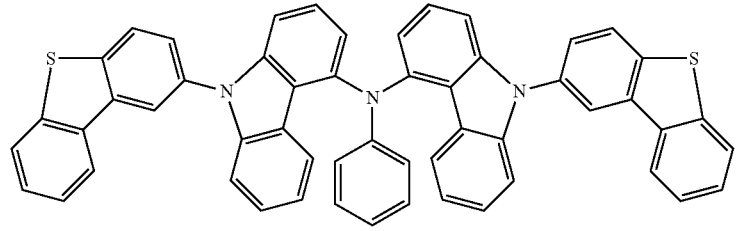
(B36)
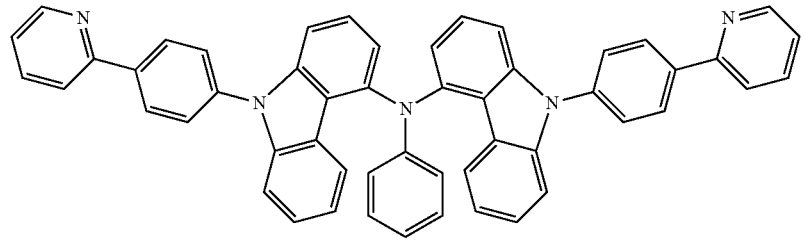
(B37)
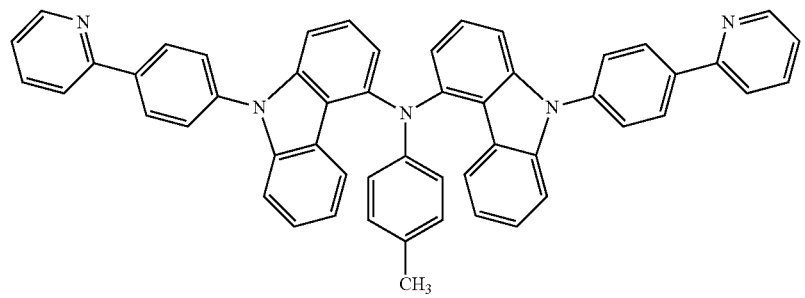
(B38)
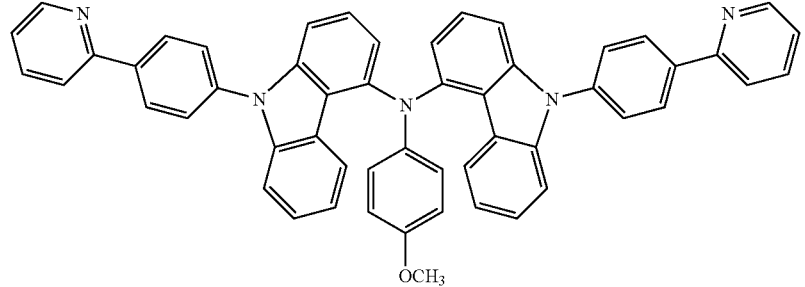
(B39)
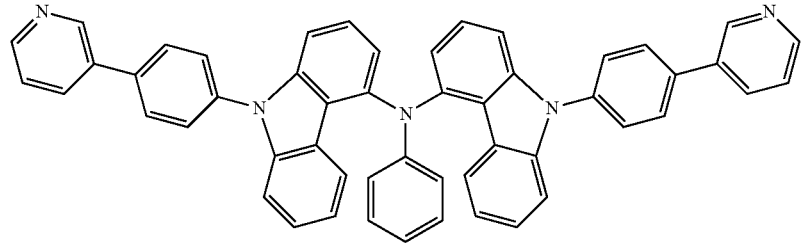

-continued
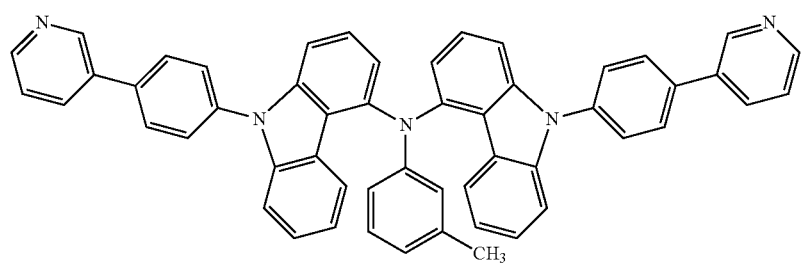
(B40)
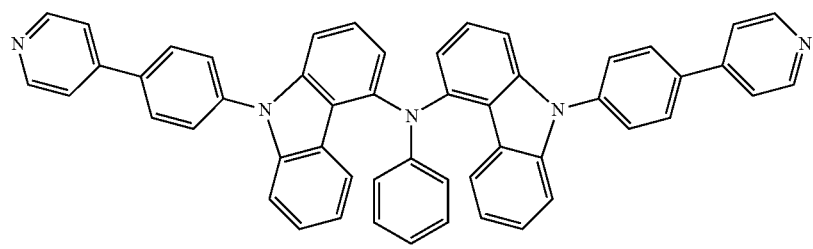
(B41)
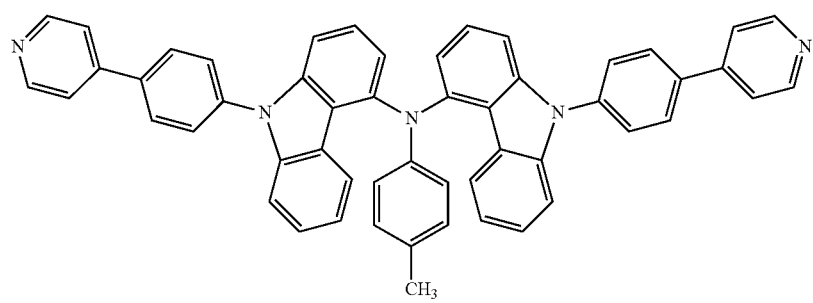
(B42)
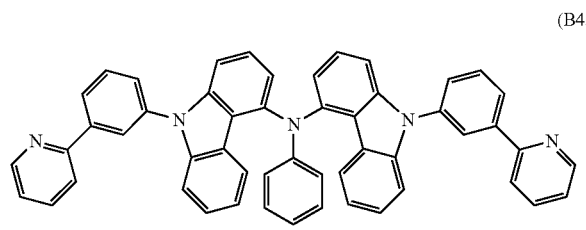
(B43)
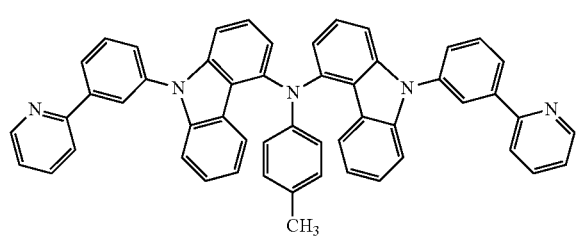
(B44)
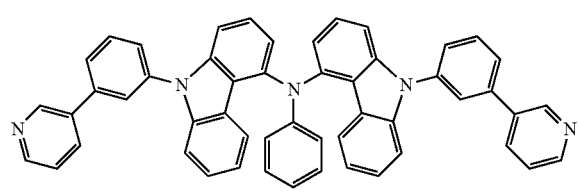
(B45)
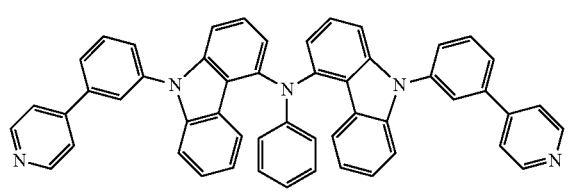
(B46)
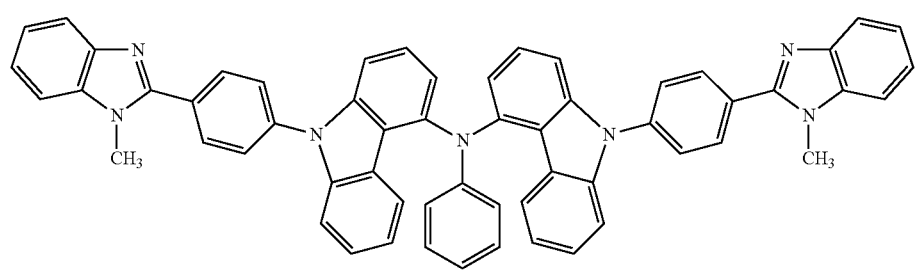
(B47)

-continued
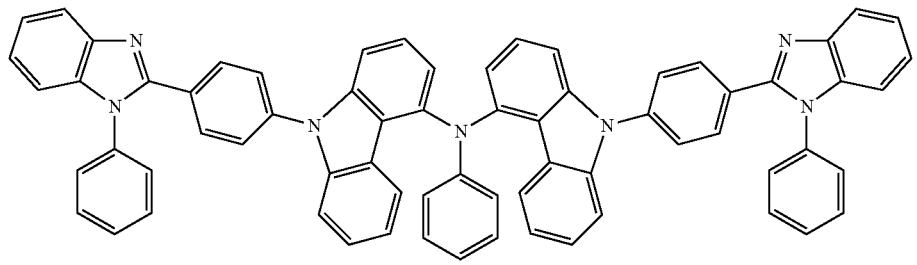
(B48)
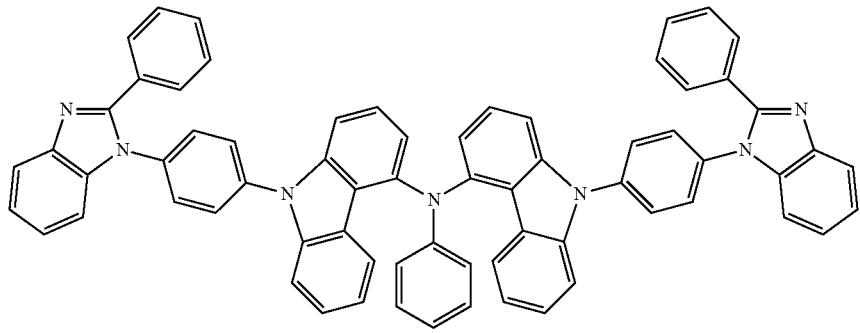
(B49)
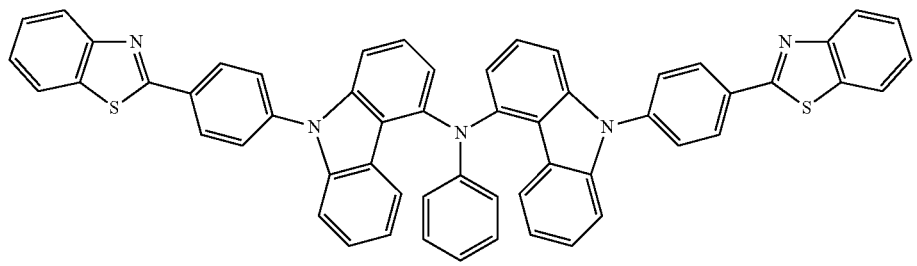
(B50)
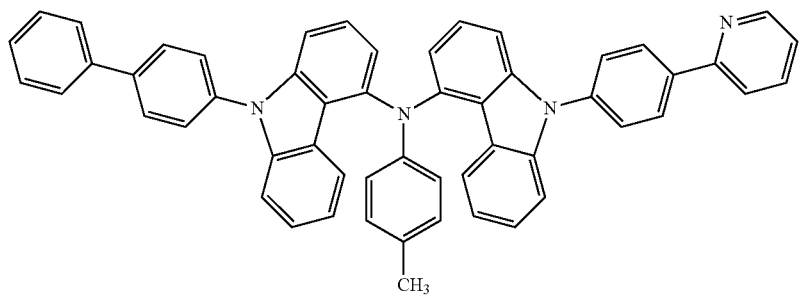
(B51)
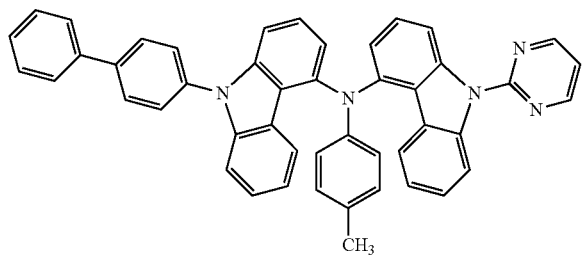
(B52)
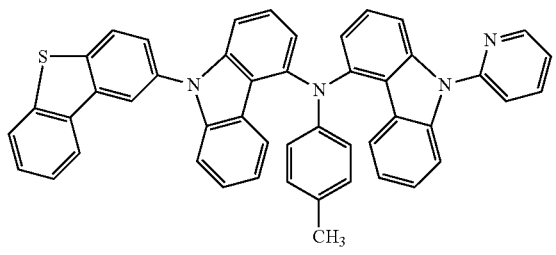
(B53)

-continued
(B54)
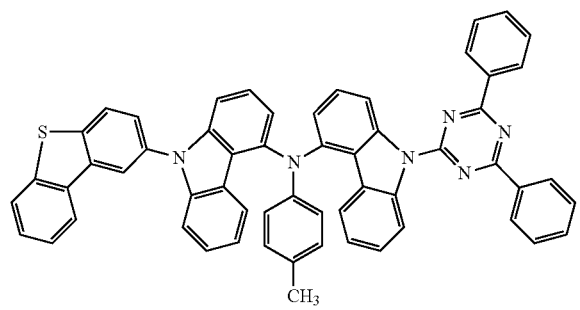
(B55)
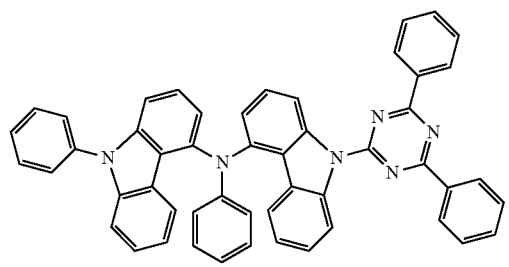
(B56)
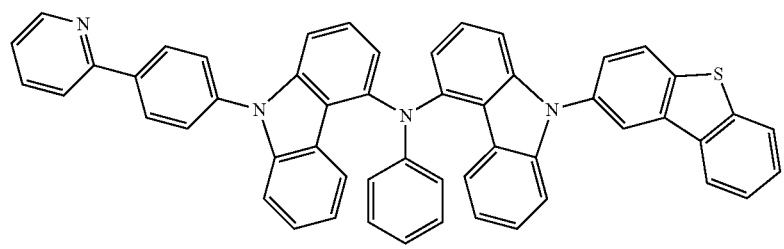
(B57)
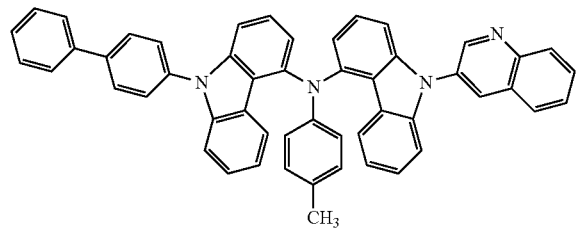
(B58)
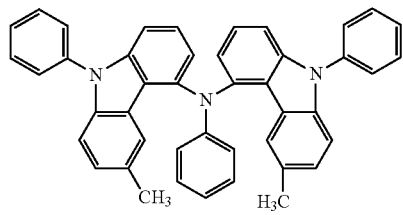
(B59)
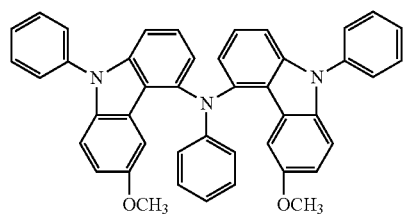
(B60)
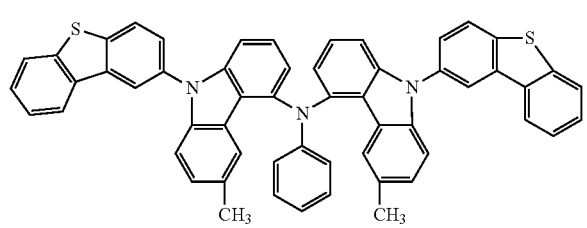
(B61)
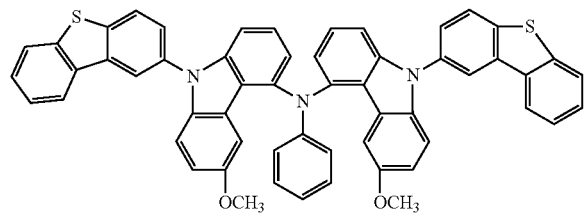
(B62)
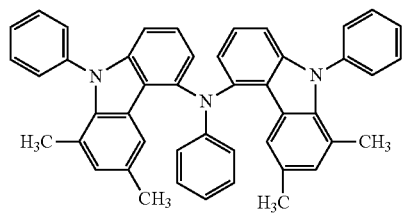

-continued
(B63)
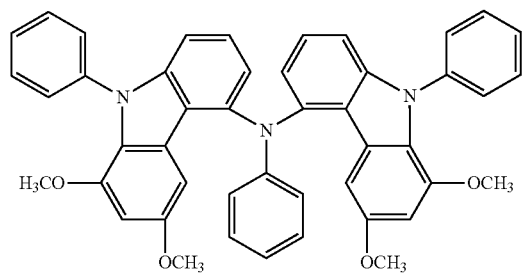
(C1)
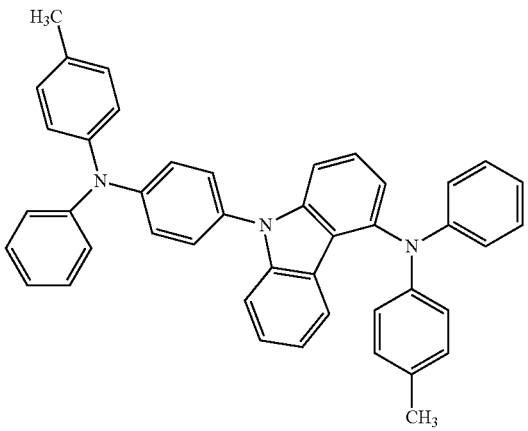
(C2)
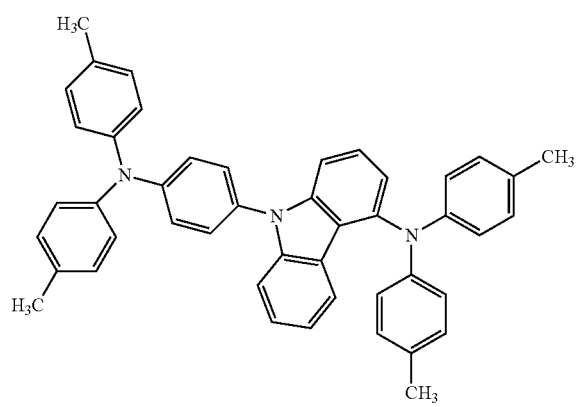
(C3)
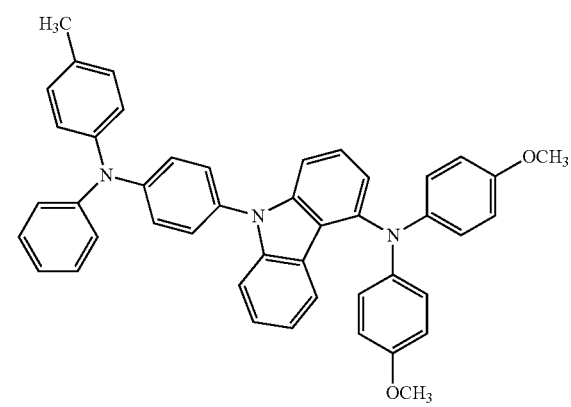
(C4)
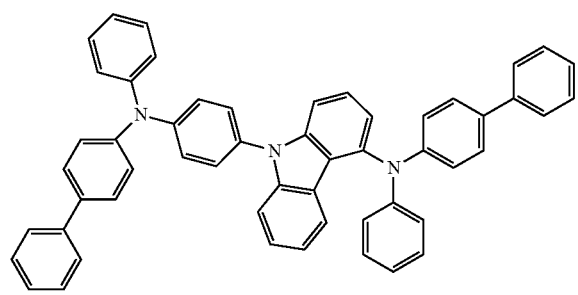
(C5)
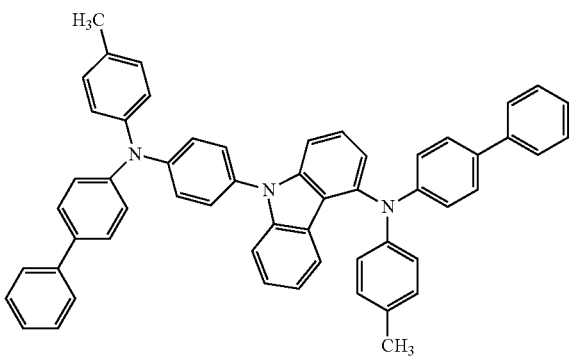
(C6)
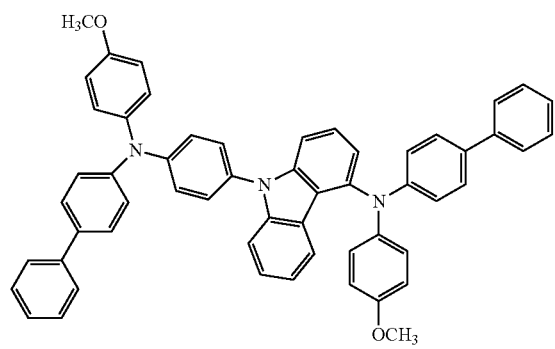
(C7)
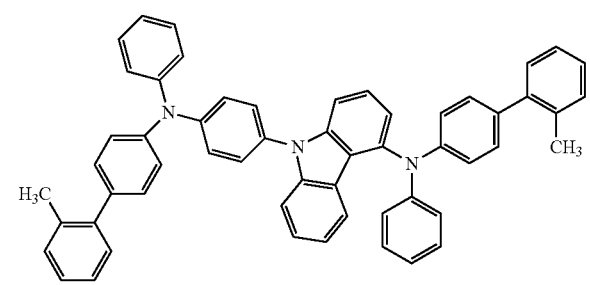

-continued
(C8)
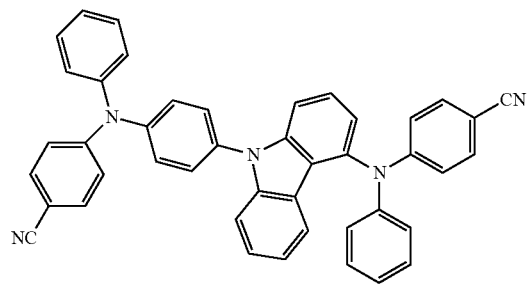
(C9)
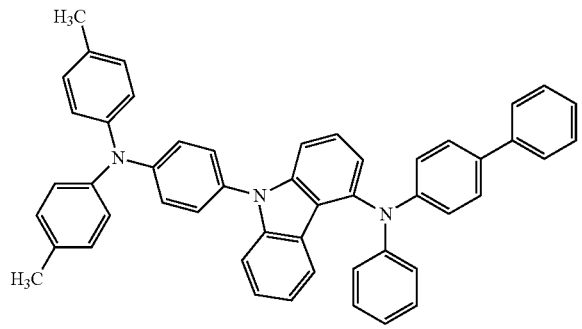
(C10)
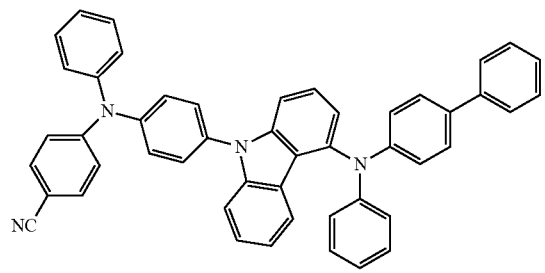
(C11)
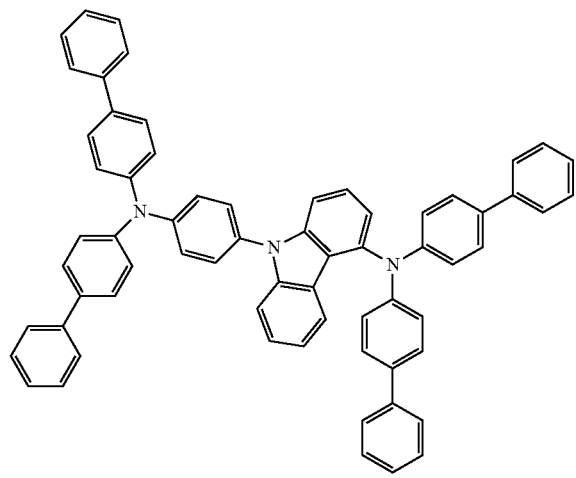
(C12)
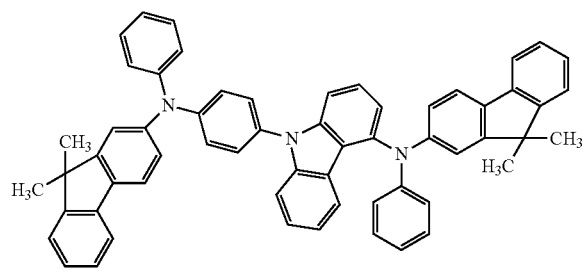
(C13)
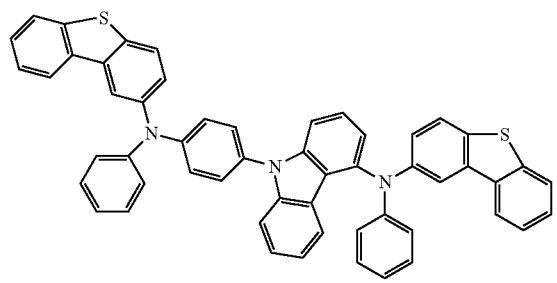
(C14)
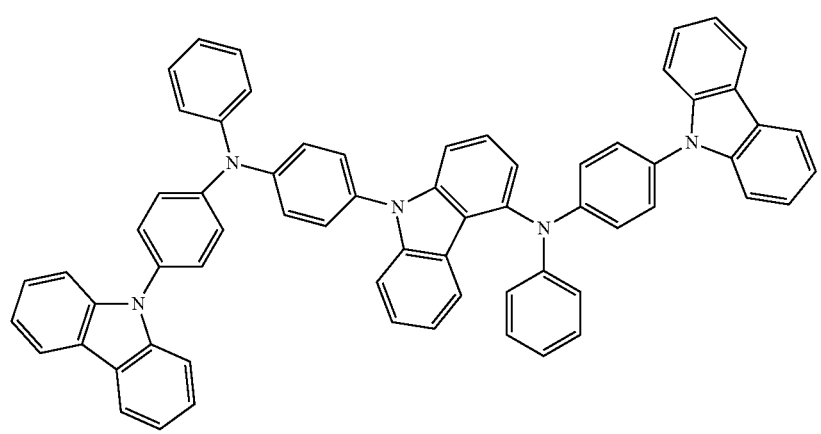

-continued
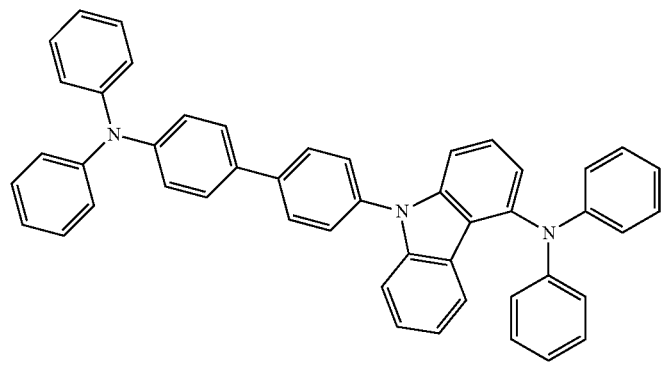
(C15)
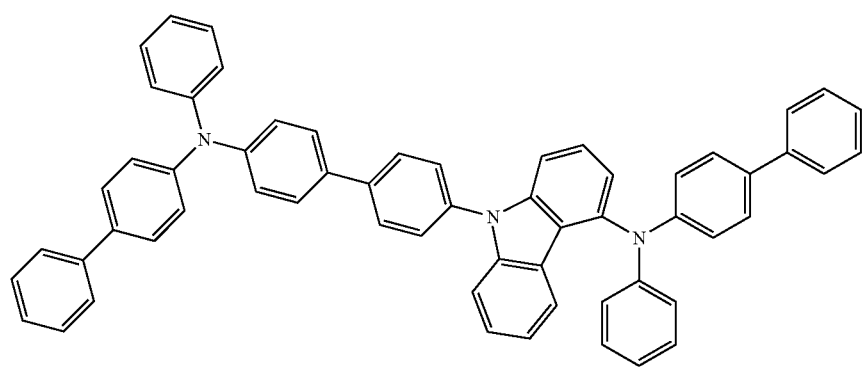
(C16)
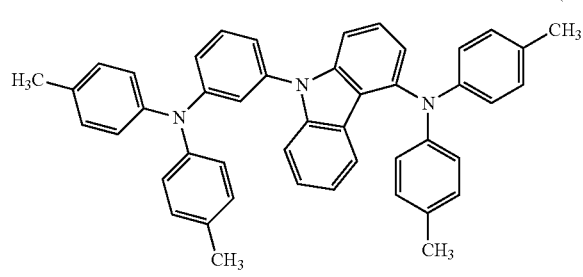
(C17)
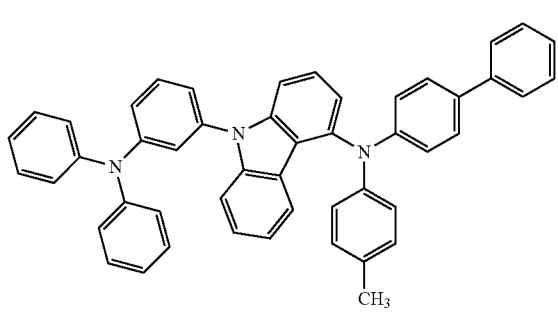
(C18)
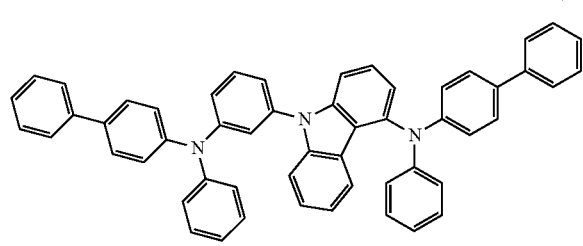
(C19)
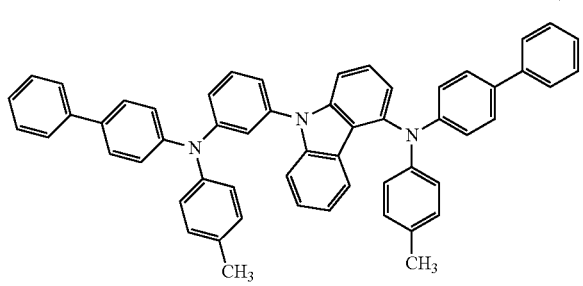
(C20)

(C21)

(C22)

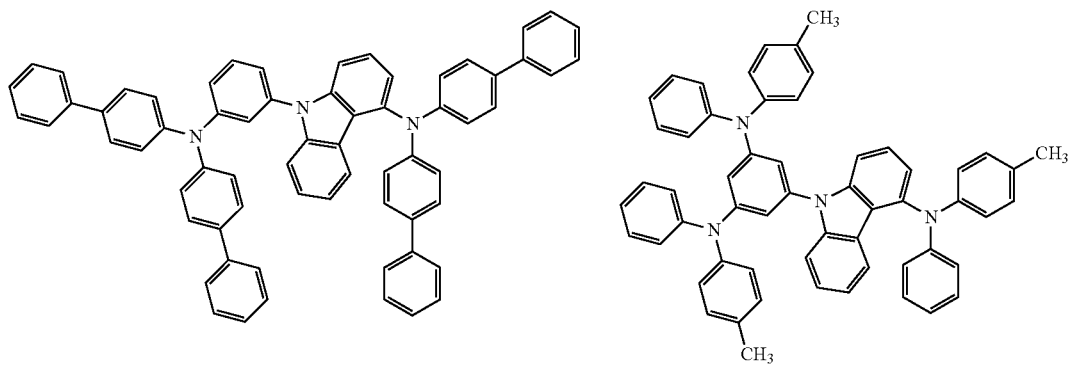

(C23)

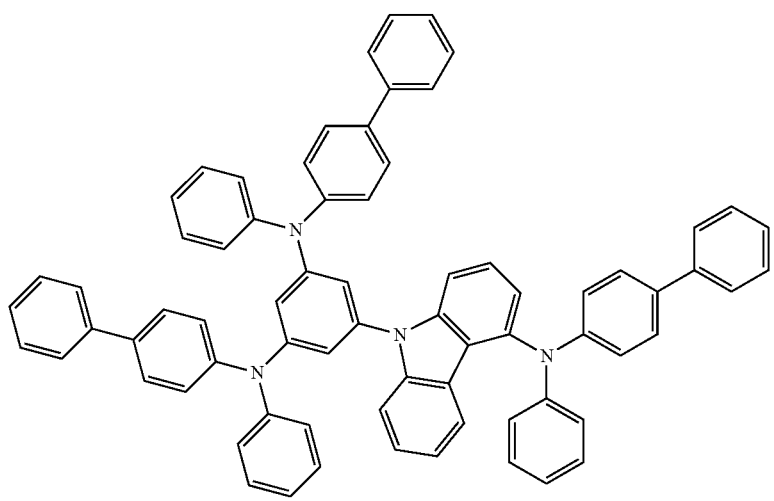

(C24)

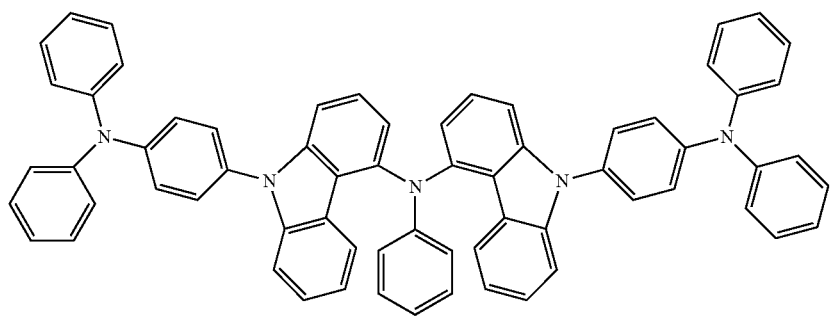

The 4-aminocarbazole compound of formula (1) can be synthesized, for example, by a process analogous to the conventional process (Tetrahedron Letters, 1998, vol. 39, p 2367) using a 9H-carbazole compound having been halogenated at the 4-position. More specifically, the 4-aminocarbazole compound of formula (1) can be synthesized through root [a] and root [b] as described below.

Root [a]

As illustrated by the reaction schemes, shown below, root [a] comprises the following steps. In a first step, a 9H-carbazole compound represented by the formula (2), which has been halogenated at the 4-position, is reacted with a compound represented by the formula (3) having a halogen atom in the presence of a base and a copper catalyst or a palladium catalyst to give a 4-halogenated-9-substituted carbazole compound represented by the formula (4). In a second step, the thus-obtained 4-halogenated-9-substituted carbazole compound of the formula (4) is reacted with a secondary amine compound represented by the formula (5) or a primary amine compound represented by the formula (6) in the presence of a base and a copper catalyst or a palladium catalyst.

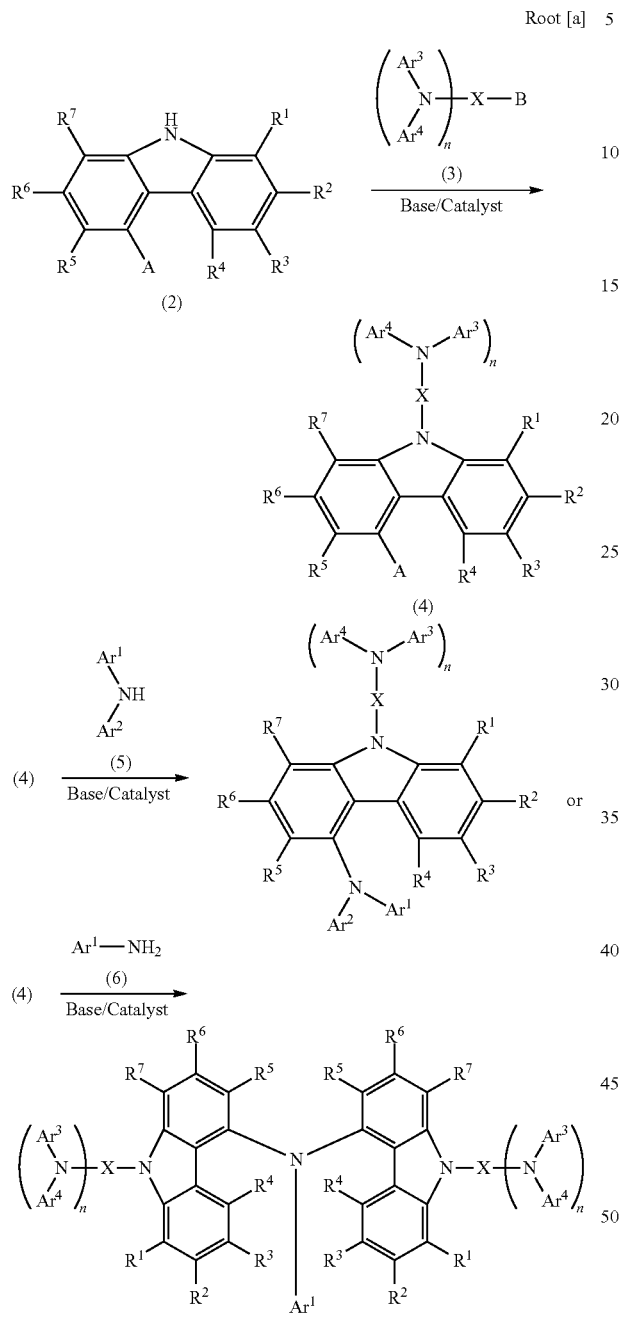

In the formulas (2) through (6), Ar¹ through Ar⁴, R¹ through R⁷, X and n are the same as those which are defined above with regard to formula (1). A, B, C and D independently represent a halogen atom (iodine, bromine, chlorine or fluorine).

Root [b]

As illustrated by the reaction schemes, shown below, root [b] comprises the following steps. In a first step, a 9H-carbazole compound represented by the formula (2), which has been halogenated at the 4-position, is reacted with a halogenated compound represented by the formula (7) in the presence of a base and a copper catalyst or a palladium catalyst to give a carbazole compound represented by the formula (8), which has been halogenated at the 4-position and to which a substituent X having a halogen atom has been introduced at the 9-position. In a second step, the thus-obtained carbazole compound of the formula (8) is reacted with a secondary amine compound represented by the formula (5) in the presence of a base and a copper catalyst or a palladium catalyst.

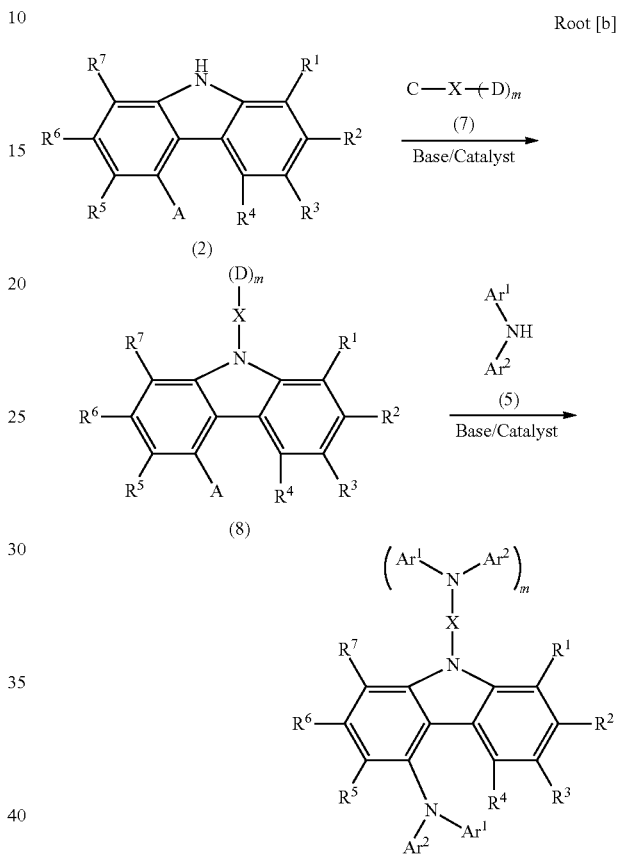

In the formulas (2), (5), (7) and (8), Ar¹ through Ar⁴, R¹ through R⁷ and X are the same as those which are defined above with regard to formula (1). A, B, C and D independently represent a halogen atom (iodine, bromine, chlorine or fluorine). m represents an integer of 0 to 2.

The process for synthesizing the 4-aminocarbazole compound of formula (1) according to the present invention is not limited to the processes including the above-mentioned root [a] and root [b], and synthesis processes including other roots can be adopted.

The 4-aminocarbazole compound of formula (1) according to the present invention can be used as a material constituting a hole injection layer, a hole transport layer and an emitting layer of an organic EL device.

More specifically, the 4-aminocarbazole compound of formula (1) can be used for an organic EL device having an emitting layer comprised of a phosphorescent luminous material or a fluorescent luminous material, preferably as a material forming at least one layer selected from a hole injection layer, a hole transport layer and an emitting layer of the organic EL device.

In the case when the 4-aminocarbazole compound of formula (1) is used for constituting a hole injection layer and/or a hole transport layer of an organic EL device, an emitting layer of the device can be formed from conventional phosphorescent or fluorescent luminous material. The emitting layer can be constituted with only a single kind of an emitting material or with a host material doped with at least one kind of emitting material.

When the 4-aminocarbazole compound of formula (1) is used for constituting a hole injection layer and/or a hole transport layer of an organic EL device, the hole injection layer and/or the hole transport layer can be formed from either the 4-aminocarbazole compound of formula (1) alone or a combination of the 4-aminocarbazole compound of formula (1) with at least one conventional electron-accepting material such as, for example, molybdenum oxide or other oxides, and 7,7,8,8-tetracyanoquinodidimetahne, 2,3,5,6-tetrafluoro-7,7,8,8-tetracyanoquinodimethane and hexacyanohexaazatriphenylene. When the 4-aminocarbazole compound of formula (1) is used as a combination thereof with a conventional electron-accepting material, the combination may be in the form of, either a single layer or, two or more laminated layers, at least one of which contains the 4-aminocarbazole compound.

The 4-aminocarbazole compound of formula (1) according to the present invention may also be used for an emitting layer of an organic EL device. When the 4-aminocarbazole compound of formula (1) is used for the emitting layer, the 4-aminocarbazole compound of formula (1) can be used either alone, or in a manner wherein a conventional emitting host material is doped with the 4-aminocarbazole compound of formula (1) or the 4-aminocarbazole compound of formula (1) is doped with a conventional emitting dopant.

The method for forming a hole injection layer, a hole transport layer or an emitting layer, which contains the 4-aminocarbazole compound of formula (1), can be any known method which includes, for example, a vacuum deposition method, a spin coating method and a casting method.

EXAMPLES

The invention will now be described more specifically by the following examples, but the scope of the invention is by no means limited thereto.

$^1$H-NMR and $^{13}$C-NMR measurements were carried out by using Gemini 200 NMR spectrometer system available from Varian, Inc.

FDMS measurement was carried out by using mass-spectrometer M-80B available from Hitachi Ltd. Triplet level was evaluated by using a F2500 type fluorescence spectrophotometer available from Hitachi High-Technologies Corporation.

Ionization potential was evaluated by cyclic voltammetry using HA-501 and HB-104 which are available from Hokuto Denko Co., Ltd.

Glass transition temperature was measured by using differential scanning calorimeter DSC-3100 available from Mac Science Co., Ltd. at a temperature elevating rate of 10° C./min.

Luminous characteristics of an organic EL device were evaluated by using LUMINANCEMETER BM-9 available from Topcon Co., Ltd., while a direct current is applied to the device.

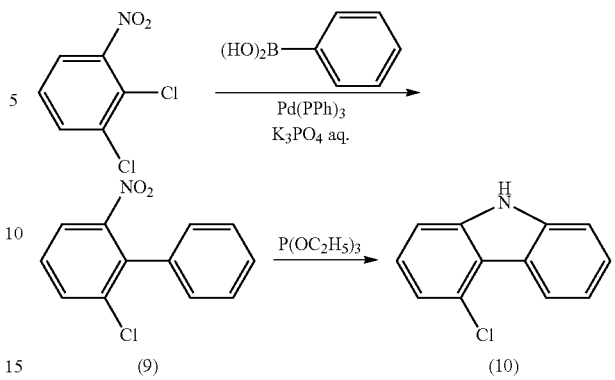

Synthesis Example 1

Synthesis of 2-nitro-6-chlorobiphenyl [formula (9)]

In a stream of nitrogen, a one-liter three-necked flask was charged with 75.0 g (390.6 mmol) of 2,3-dichloronitrobenzene, 47.6 g (390.6 mmol) of phenylboric acid, 9.0 g (7.8 mmol) of tetrakis(triphenylphosphine)palladium, 250 mL of tetrahydrofuran, and 518 g (976.5 mmol) of an aqueous tripotassium phosphate solution with 40 wt. % concentration. The mixture was heated under reflux for 8 hours. The reaction mixture was cooled to room temperature, and then separated into an aqueous phase and an organic phase. The organic phase was washed with an aqueous saturated ammonium chloride solution and then with an aqueous saturated sodium chloride solution. The washed organic phase was dried over anhydrous magnesium sulfate and then a solvent was distilled off under reduced pressure. The thus-obtained solid was recrystallized from ethanol to give 62.8 g of 2-nitro-6-chlorobiphenyl as a light yellow needle crystal (yield: 680).

The compound was identified by $^1$H-NMR measurement and $^{13}$C-NMR measurement.

$^1$H-NMR (CDCl$_3$); 7.66-7.74 (m, 2H), 7.41-7.45 (m, 4H), 7.22-7.27 (m, 2H)

$^{13}$C-NMR (CDCl$_3$); 135.71, 134.68, 133.91, 133.29, 128.91, 128.71, 128.68, 128.55, 128.46, 121.96

Synthesis Example 2

Synthesis of 4-chlorocarbazole [formula (10)]

In a stream of nitrogen, a 500 mL egg-plant flask was charged with 60.0 g (257.4 mmol) of 2-nitro-6-chlorobiphenyl, obtained in Synthesis Example 1. The content was heated to 140° C., and 106 g of triethyl phosphite was dropwise added over 2 hours. After the dropwise addition, the content was further heated at 140° C. for 2 hours. Then triethyl phosphite was distilled off under reduced pressure. Toluene was added to the residue, and the thus-deposited solid was filtered. The thus-obtained crude product was purified by silica gel column chromatography using toluene as a developing solvent to give 18.9 g (93.72 mmol) of 4-chlorocarbazole as a white powder (yield: 36%).

The compound was identified by $^1$H-NMR measurement and $^{13}$C-NMR measurement.

$^1$H-NMR (Acetone-d6); 10.71 (br-s, 1H), 8.52 (d, 1H), 7.15-7.59 (m, 6H)

$^{13}$C-NMR (Acetone-d6); 141.80, 140.71, 128.37, 126.76, 126.61, 122.99, 122.33, 120.57, 119.88, 119.75, 111.45, 110.15

Synthesis Example 3

Synthesis of 4-chloro-9-(4-biphenylyl)carbazole

In a stream of nitrogen, a 200 mL three-necked flask was charged with 10.0 g (49.5 mmol) of 4-chlorocarbazole, obtained in Synthesis Example 2, 11.6 g (52.0 mmol) of 4-bromobiphenyl, 9.5 g (69.4 mmol) of potassium carbonate, 100 mL of o-xylene, 111 mg (0.49 mmol) of palladium acetate and 349 mg (1.73 mmol) of tri(tert-butyl)phosphine. The content was stirred at 130° C. for 14 hours. The reaction mixture was cooled to room temperature, and then 50 mL of pure water was added to separate an organic phase. The organic phase was washed with pure water and then with an aqueous saturated sodium chloride solution. The washed organic phase was dried over anhydrous magnesium sulfate, and then the solvent was distilled off under reduced pressure. The thus-obtained powder was washed with ethanol to give 12.5 g (35.4 mmol) of 4-chloro-9-(4-biphenylyl)carbazole as a light brown powder (yield: 71%).

The compound was identified by $^1$H-NMR measurement and $^{13}$C-NMR measurement.

$^1$H-NMR (CDCl$_3$); 8.68 (d, 1H), 7.80 (d, 2H), 7.67 (d, 2H), 7.22-7.59 (m, 11H)

$^{13}$C-NMR (CDCl$_3$); 142.04, 141.05, 140.83, 140.08, 136.29, 128.97, 128.79, 128.58, 127.74, 127.61, 127.14, 126.48, 126.13, 123.13, 122.32, 120.75, 120.62, 120.33, 109.65, 108.20

Synthesis Example 4

Synthesis of 4-chloro-9-(3-quinolyl)carbazole

In a stream of nitrogen, a 100 mL three-necked flask was charged with 5.0 g (24.7 mmol) of 4-chlorocarbazole, obtained in Synthesis Example 2, 5.1 g (24.7 mmol) of 3-bromoquinoline, 4.7 g (34.7 mmol) of potassium carbonate, 25 mL of o-xylene, 276 mg (1.23 mmol) of palladium acetate and 869 mg (4.3 mmol) of tri(tert-butyl)phosphine. The content was stirred at 140° C. for 24 hours. The reaction mixture was cooled to room temperature, and then 20 mL of pure water was added to separate an organic phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=3/1 by volume) as a developing solvent to give 4.6 g (14.0 mmol) of 4-chloro-9-(3-quinolyl)carbazole as a brown glassy solid (yield: 56%).

The compound was identified by $^1$H-NMR measurement and $^{13}$C-NMR measurement.

$^1$H-NMR (CDCl$_3$); 9.09 (s, 1H), 8.70 (d, 1H), 8.31 (s, 1H), 8.26 (d, 1H), 7.90 (d, 1H), 7.82 (d, 1H), 7.66 (t, 1H), 7.22-7.51 (m, 6H)

$^{13}$C-NMR (CDCl$_3$); 183.45, 149.59, 147.23, 142.06, 141.07, 133.38, 130.84, 130.27, 129.59, 129.02, 128.18, 127.78, 126.83, 126.48, 123.35, 122.61, 121.41, 120.95, 109.16, 107.73

Synthesis Example 5

Synthesis of 4-chloro-9-(2-benzothienyl)carbazole

In a stream of nitrogen, a 50 mL three-necked flask was charged with 2.6 g (12.9 mmol) of 4-chlorocarbazole, obtained in Synthesis Example 2, 3.4 g (12.9 mmol) of 2-bromodibenzothiophene, 3.5 g (25.9 mmol) of potassium carbonate, 13 mL of o-xylene, 29 mg (0.12 mmol) of palladium acetate and 91 mg (0.45 mmol) of tri(tert-butyl)phosphine. The content was stirred at 140° C. for 18 hours. The reaction mixture was cooled to room temperature, and then 10 mL of pure water was added to separate an organic phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 3.5 g (9.1 mmol) of 4-chloro-9-(2-benzothienyl)carbazole as a brown glasslike solid (yield: 70%).

The compound was identified by $^1$H-NMR measurement.

$^1$H-NMR (CDCl$_3$); 8.71 (d, 1H), 8.27 (d, 1H), 8.04-8.16 (m, 3H), 7.83-7.94 (m, 2H), 7.25-7.61 (m, 7H)

Synthesis Example 6

Synthesis of 4-chloro-9-[4-(2-pyridyl)phenyl]carbazole

In a stream of nitrogen, a 100 mL three-necked flask was charged with 5.0 g (24.7 mmol) of 4-chlorocarbazole, obtained in Synthesis Example 2, 6.0 g (26.0 mmol) of 4-(2-pyridyl)bromobenzene, 4.7 g (34.7 mmol) of potassium carbonate, 25 mL of o-xylene, 55 mg (0.24 mmol) of palladium acetate and 174 mg (0.86 mmol) of tri(tert-butyl)phosphine. The content was stirred at 140° C. for 14 hours. The reaction mixture was cooled to room temperature, and then 20 mL of pure water was added to separate an organic phase. The organic phase was washed with water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=2/1 by volume) as a developing solvent to give 4.5 g (12.7 mmol) of 4-chloro-9-[4-(2-pyridyl)phenyl]carbazole as a brown glassy solid (yield: 51%).

The compound was identified by $^1$H-NMR measurement and $^{13}$C-NMR measurement.

$^1$H-NMR (CDCl$_3$); 8.66-8.75 (m, 2H) 8.20 (d, 2H), 7.77 (d, 2H), 7.61 (d, 2H), 7.22-7.46 (m, 7H)

$^{13}$C-NMR (CDCl$_3$); 156.33, 149.84, 141.92, 140.93, 138.93, 137.76, 136.92, 128.79, 128.49, 127.50, 126.53, 126.19, 123.15, 122.50, 122.39, 120.86, 120.69, 120.56, 120.42, 109.65, 108.20

Synthesis Example 7

Synthesis of 4-chloro-9-(4-chlorophenyl)carbazole

In a stream of nitrogen, a 100 mL three-necked flask was charged with 5.0 g (24.7 mmol) of 4-chlorocarbazole, obtained in Synthesis Example 2, 5.1 g (27.2 mmol) of p-bromochlorobenzene, 4.7 g (34.7 mmol) of potassium carbonate, 50 mL of o-xylene, 55 mg (0.24 mmol) of palladium acetate and 174 mg (0.86 mmol) of tri(tert-butyl)phosphine. The content was stirred at 130° C. for 24 hours. The reaction mixture was cooled to room temperature, and then 30 mL of pure water was added to separate an organic phase. The organic phase was washed with water and then with an aqueous saturated sodium chloride solution. The washed organic phase was dried over anhydrous magnesium sulfate, and then the solvent was distilled off under reduced pressure. The thus-obtained residue was purified by silica gel column chromatography using hexane as a developing solvent to give 4.4 g (14.1 mmol) of 4-chloro-9-(4-chlorophenyl)carbazole as a white solid (yield: 56%).

The compound was identified by $^1$H-NMR measurement and $^{13}$C-NMR measurement.

$^1$H-NMR (CDCl$_3$); 8.64 (d, 1H), 7.53 (d, 2H), 7.15-7.45 (m, 8H)

$^{13}$C-NMR (CDCl$_3$); 141.86, 140.87, 135.73, 133.62, 130.25, 128.88, 128.69, 126.61, 126.26, 123.20, 122.38, 120.98, 120.69, 120.56, 109.36, 107.93

Synthesis Example 8

Synthesis of 4-chloro-9-phenylcarbazole

In a stream of nitrogen, a 200 mL three-necked flask was charged with 17.0 g (84.3 mmol) of 4-chlorocarbazole, obtained in Synthesis Example 2, 15.8 g (101.1 mmol) of bromobenzene, 19.5 g (141.6 mmol) of potassium carbonate, 85 mL of o-xylene, 227 mg (1.0 mmol) of palladium acetate and 714 mg (3.5 mmol) of tri(tert-butyl)phosphine. The content was stirred at 130° C. for 24 hours. The reaction mixture was cooled to room temperature, and then 60 mL of pure water was added to separate an organic phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using hexane as a developing solvent to give 14.3 g (51.6 mmol) of 4-chloro-9-phenylcarbazole as a colorless oily material (yield: 61%).

The compound was identified by $^1$H-NMR measurement and $^{13}$C-NMR measurement.

$^1$H-NMR (CDCl$_3$); 8.67 (d, 1H), 7.23-7.65 (m, 11H)

$^{13}$C-NMR (CDCl$_3$); 142.04, 141.05, 137.15, 129.94, 128.73, 127.93, 127.39, 126.41, 126.06, 123.07, 122.21, 120.64, 120.51, 120.23, 109.56, 108.11

Synthesis Example 9

Synthesis of 4-chloro-9-(4,6-diphenyl-1,3,5-triazin-2-yl)carbazole

In a stream of nitrogen, a 100 mL three-necked flask was charged with 0.53 g (13.4 mmol) of sodium hydride (oily, 60%). 15 mL of dehydrated dimethylformamide was added to the content, and the mixture was stirred. To the thus-obtained slurry, a solution of 2.2 g (11.2 mmol) of 4-chlorocarbazole in 15 mL of dehydrated dimethylformamide was dropwise added, and the mixture was stirred for 30 minutes. To the thus-obtained reaction mixture, a solution of 3.0 g (11.2 mmol) of 2-chloro-4,6-diphenyl-1,3,5-triazine in 40 mL of dehydrated dimethylformamide was dropwise added. The reaction mixture was stirred at room temperature for 2 hours, and, 10 mL of methanol and then 100 mL of pure water were added to terminate the reaction. A white powder deposited upon the addition of pure water was collected, and washed with pure water and then with ethanol. The thus-obtained powder was recrystallized from o-xylene to give 3.1 g (7.2 mmol) of 4-chloro-9-(4,6-diphenyl-1,3,5-triazin-2-yl)carbazole as a white crystal (yield: 64%).

The compound was identified by $^1$H-NMR measurement.

$^1$H-NMR (CDCl$_3$); 8.72 (d, 1H), 8.71 (d, 4H), 7.91-8.01 (m, 2H), 7.37-7.65 (m, 10H)

Synthesis Example 10

Synthesis of 4-chloro-6-phenyl-9-(4-biphenylyl)carbazole

In a stream of nitrogen, a 50 mL three-necked flask was charged with 1.8 g (5.2 mmol) of 4-chloro-9-(4-biphenylyl)carbazole, obtained in Synthesis Example 3. Then, 10 mL of dimethylformamide and 0.93 g (5.2 mmol) of N-bromosuccinimide were added to the content. The mixture was stirred at room temperature for 2 hours, and then 10 mL of pure water was added to the reaction mixture. The thus-deposited white powder was collected by filtration. Then the white powder was washed with pure water and with methanol, and then dried under reduced pressure to give a white powdery product. The white powdery product was a mixture comprised of 4-chloro-9-(4-biphenylyl)carbazole (i.e., the raw material), 4-chloro-6-bromo-9-(4-biphenylyl)carbazole and 4-chloro-3,6-dibromo-9-(4-biphenylyl)carbazole. The purity of 4-chloro-6-bromo-9-(4-biphenylyl) carbazole was 72%.

In a stream of nitrogen, a 10 mL three-necked flask was charged with 0.90 g of the above-mentioned mixture, and further with 0.26 g (2.1 mmol) of phenylboric acid, 0.11 g (0.09 mmol) of tetrakis(triphenylphosphine)palladium, 5 mL of tetrahydrofuran, and 2.5 g (4.8 mmol) of an aqueous potassium carbonate solution with a 20 wt. % concentration. The content was heated under reflux for 14 hours. The reaction mixture was cooled to room temperature, and then separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using hexane as a developing solvent to give 0.51 g (1.0 mmol) of 4-chloro-6-phenyl-9-(4-biphenylyl)carbazole as a white powder (yield: 19%).

The compound was identified by $^1$H-NMR measurement.

$^1$H-NMR (CDCl$_3$); 8.39 (s, 1H), 7.23-7.82 (m, 19H)

Synthesis Example 11

Synthesis of N-(4-bromophenyl)-N-biphenylylamine

In a stream of nitrogen, a 100 mL three-necked flask was charged with 15.0 g (61.1 mmol) of N-phenyl-N-biphenylylamine. 100 mL of dimethylformamide and 10.8 g (61.1 mmol) of N-bromosuccinimide were added to the content, and the mixture was stirred at room temperature for 2 hours. To the thus-obtained reaction mixture, 10 mL of toluene and then 10 mL of pure water were added, and the reaction mixture was separated into an organic phase and an aqueous phase. The organic phase was washed with pure water and then with an aqueous saturated sodium chloride solution. The washed organic phase was dried over anhydrous magnesium sulfate, and then, the solvent was distilled off under reduced pressure. The thus-obtained solid was recrystallized from toluene to give 13.4 g (41.4 mmol) of N-(4-bromophenyl)-N-biphenylylamine as a grey powder (yield: 67%).

The compound was identified by ¹H-NMR measurement and ¹³C-NMR measurement.

¹H-NMR (Acetone-d6); 7.55-7.64 (m, 5H), 7.27-7.45 (m, 5H), 7.21 (d, 2H), 7.11 (d, 2H)

¹³C-NMR (Acetone-d6); 143.18, 142.61, 140.76, 133.40, 132.08, 128.88, 127.74126.62, 126.26, 118.90, 118.05, 111.33

Synthesis Example 12

Synthesis of N-biphenylyl-N-(m-terphenylyl)amine

In a stream of nitrogen, a 300 mL three-necked flask was charged with 12.0 g (37.1 mmol) of N-(4-bromophenyl)-N-biphenylylamine, obtained in Synthesis Example 11, 7.7 g (38.9 mmol) of 3-biphenylboric acid, 2.1 g (1.8 mmol) of tetrakis(triphenylphosphine)palladium, 60 mL of toluene, 10 mL of ethanol, and 49 g (92.8 mmol) of an aqueous tripotassium phosphate solution with a 40 wt. % concentration. The content was heated under reflux for 5 hours. The reaction mixture was cooled to room temperature, and then separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/1 by volume) as a developing solvent to give 10.2 g (25.6 mmol) of N-biphenylyl-N-(m-terphenylyl) amine as a light yellow powder (yield: 69%).

The compound was identified by ¹H-NMR measurement and ¹³C-NMR measurement.

¹H-NMR (Acetone-d6); 7.89 (s, 1H), 7.37-7.73 (m, 17H), 7.26-7.32 (m, 5H)

¹³C-NMR (Acetone-d6); 143.29, 143.09, 141.68, 141.53, 140.85, 132.93, 132.78, 129.43, 128.91, 128.84, 127.91, 127.70, 127.45, 127.12, 126.51, 126.20, 125.29, 125.18, 124.92, 117.73, 117.65, 117.59

Synthesis Example 13

Synthesis of N-biphenylyl-N-[4-(4-dibenzothienyl)phenyl]amine

In a stream of nitrogen, a 300 mL three-necked flask was charged with 7.0 g (21.6 mmol) of N-(4-bromophenyl)-N-biphenylylamine, obtained in Synthesis Example 11, 5.9 g (25.9 mmol) of dibenzothiophene-4-boric acid, 1.2 g (1.0 mmol) of tetrakis(triphenylphosphine)palladium, 35 mL of toluene, 5 mL of ethanol, and 28 g (54.1 mmol) of an aqueous tripotassium phosphate solution with a 40 wt. % concentration. The content was heated under reflux for 3 hours. The reaction mixture was cooled to room temperature, and then separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/1 by volume) as a developing solvent to give 5.2 g (12.1 mmol) of N-biphenylyl-N-[4-(4-dibenzothienyl)-phenyl]amine as a light yellow powder (yield: 56%).

The compound was identified by ¹H-NMR measurement and ¹³C-NMR measurement.

¹H-NMR (Acetone-d6); 8.22-8.32 (m, 2H), 7.90-7.95 (m, 1H), 7.77 (s, 1H), 7.27-7.70 (m, 17H)

¹³C-NMR (Acetone-d6); 143.78, 142.81, 140.82, 139.41, 137.98, 137.03, 136.37, 135.98, 133.22, 132.15, 129.17, 128.88, 127.76, 127.08, 126.66, 126.59, 126.26, 125.58, 124.70, 122.72, 122.01, 120.20, 118.09, 117.19

Example 1

Synthesis of Compound A5

In a stream of nitrogen, a 100 mL three-necked flask was charged with 3.5 g (9.9 mmol) of 4-chloro-9-(4-biphenylyl)-carbazole, obtained in Synthesis Example 3, 2.4 g (9.9 mmol) of N-phenyl-N-biphenylylamine, 1.3 g (13.8 mmol) of sodium tert-butoxide, 35 mL of o-xylene, 22 mg (0.09 mmol) of palladium acetate and 69 mg (0.34 mmol) of tri(tert-butyl) phosphine. The content was stirred at 140° C. for 12 hours. The reaction mixture was cooled to room temperature, and then 25 mL of pure water was added and stirred. The mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 3.4 g (6.0 mmol) of compound A5 as a white glassy solid (yield: 60%).

The compound was identified by FDMS, ¹H-NMR measurement and ¹³C-NMR measurement.

FDMS: 562

¹H-NMR (CDCl₃); 7.89 (d, 1H), 7.80 (d, 2H), 7.61-7.70 (m, 3H), 7.21-7.55 (m, 22H), 6.99-7.10 (m, 2H)

¹³C-NMR (CDCl₃); 146.71, 142.79, 141.02, 140.93, 140.71, 140.60, 140.19, 136.68, 134.50, 129.01, 128.71, 128.57, 127.82, 127.71, 127.17, 126.99, 126.68, 126.59, 125.93, 123.16, 122.03, 121.66, 121.31, 120.78, 120.31, 109.39, 107.69

Example 2

Synthesis of Compound A8

In a stream of nitrogen, a 100 mL three-necked flask was charged with 3.5 g (9.9 mmol) of 4-chloro-9-(4-biphenylyl)-carbazole, obtained in Synthesis Example 3, 3.1 g (9.9 mmol) of N,N-bis(4-biphenylyl)amine, 1.3 g (13.8 mmol) of sodium tert-butoxide, 35 mL of o-xylene, 22 mg (0.09 mmol) of palladium acetate and 69 mg (0.34 mmol) of tri(tert-butyl) phosphine. The content was stirred at 140° C. for 12 hours. The reaction mixture was cooled to room temperature, and then 20 mL of pure water was added and stirred. The mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 3.4 g (5.3 mmol) of compound A8 as a light yellow glassy solid (yield: 53%).

The compound was identified by FDMS, ¹H-NMR measurement and ¹³C-NMR measurement.

FDMS: 638

¹H-NMR (CDCl₃); 7.88 (d, 1H), 7.81 (d, 2H), 7.66 (t, 4H), 7.20-7.56 (m, 25H), 6.99-7.10 (m, 2H)

$^{13}$C-NMR (CDCl$_3$); 146.49, 142.57, 140.81, 140.72, 140.50, 140.39, 139.99, 136.47, 134.29, 128.78, 128.49, 128.36, 127.61, 127.50, 126.97, 126.77, 126.46, 126.38, 125.71, 122.96, 121.81, 121.46, 121.11, 120.58, 120.08, 109.19, 107.49

Example 3

Synthesis of Compound A15

In a stream of nitrogen, a 50 mL three-necked flask was charged with 4.6 g (13.0 mmol) of 4-chloro-9-(4-biphenylyl)-carbazole, obtained in Synthesis Example 3, 4.2 g (14.3 mmol) of N-(p-tolyl)N-(9,9'-dimethylfluoren-2-yl)amine, 1.7 g (18.2 mmol) of sodium tert-butoxide, 25 mL of o-xylene, 58 mg (0.26 mmol) of palladium acetate and 184 mg (0.91 mmol) of tri(tert-butyl)phosphine. The content was stirred at 140° C. for 10 hours. The reaction mixture was cooled to room temperature, and then 20 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 6.0 g (9.9 mmol) of compound A15 as a light yellow glassy solid (yield: 75%).

The compound was identified by FDMS and $^1$H-NMR measurement.

FDMS: 616

$^1$H-NMR (CDCl$_3$); 7.84 (d, 1H), 6.99-7.68 (m, 26H), 2.26 (s, 3H), 1.39 (s, 6H)

Example 4

Synthesis of Compound A278

In a stream of nitrogen, a 50 mL three-necked flask was charged with 4.0 g (11.3 mmol) of 4-chloro-9-(4-biphenylyl)-carbazole, obtained in Synthesis Example 3, 3.2 g (12.4 mmol) of N-(2-dibenzofuranyl)-N-phenylamine, 1.5 g (15.8 mmol) of sodium tert-butoxide, 20 mL of o-xylene, 50 mg (0.22 mmol) of palladium acetate and 155 mg (0.77 mmol) of tri(tert-butyl)phosphine. The content was stirred at 140° C. for 12 hours. The reaction mixture was cooled to room temperature, and then 15 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 4.6 g (8.0 mmol) of compound A278 as a white glassy solid (yield: 71%).

The compound was identified by FDMS.
FDMS: 576

Example 5

Synthesis of Compound A286

In a stream of nitrogen, a 50 mL three-necked flask was charged with 0.48 g (1.7 mmol) of 4-chloro-9-phenylcarbazole, obtained in Synthesis Example 8, 0.70 g (1.7 mmol) of N-biphenylyl-N-(m-terphenylyl)amine, obtained in Synthesis Example 12, 0.23 g (2.4 mmol) of sodium tert-butoxide, 10 mL of o-xylene, 8 mg (0.03 mmol) of palladium acetate and 24 mg (0.12 mmol) of tri(tert-butyl)phosphine. The content was stirred at 140° C. for 14 hours. The reaction mixture was cooled to room temperature, and then 10 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 0.77 g (1.2 mmol) of compound A286 as a light yellow glassy solid (yield: 71%).

The compound was identified by FDMS.
FDMS: 638

Example 6

Synthesis of Compound A289

In a stream of nitrogen, a 100 mL three-necked flask was charged with 4.0 g (14.4 mmol) of 4-chloro-9-phenylcarbazole, obtained in Synthesis Example 8, 4.8 g (14.4 mmol) of N-phenyl-N-(11,11'-dimethylbenzo[a]fluoren-9-yl)amine, 1.9 g (20.1 mmol) of sodium tert-butoxide, 30 mL of o-xylene, 64 mg (0.28 mmol) of palladium acetate and 197 mg (0.98 mmol) of tri(tert-butyl)phosphine. The content was stirred at 140° C. for 12 hours. The reaction mixture was cooled to room temperature, and then 10 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 5.4 g (9.5 mmol) of compound A289 as a light yellow glassy solid (yield: 66%).

The compound was identified by FDMS, $^1$H-NMR measurement and $^{13}$C-NMR measurement.

FDMS: 576

$^1$H-NMR (CDCl$_3$); 8.15 (d, 1H), 7.89 (d, 1H), 7.78-7.83 (m, 3H), 7.20-7.60 (m, 17H), 7.06 (d, 2H), 6.91-7.99 (m, 2H) 1.65 (s, 6H)

$^{13}$C-NMR (CDCl$_3$); 156.31, 147.34, 146.62, 146.24, 142.28, 141.15, 140.38, 137.12, 136.24, 133.18, 132.92, 129.39, 129.32, 129.15, 128.71, 127.91, 127.19, 127.01, 126.31, 125.42, 125.16, 123.79, 123.35, 122.71, 121.11, 120.40, 119.89, 119.79, 119.45, 118.04, 116.04, 108.68, 106.61, 48.14, 25.93

Example 7

Synthesis of Compound A292

In a stream of nitrogen, a 50 mL three-necked flask was charged with 0.72 g (2.6 mmol) of 4-chloro-9-phenylcarbazole, obtained in Synthesis Example 8, 1.2 g (2.8 mmol) of N-biphenylyl-N-[4-(4-dibenzothienyl)phenyl]amine, 0.35 g (3.6 mmol) of sodium tert-butoxide, 10 mL of o-xylene, 17 mg (0.07 mmol) of palladium acetate and 55 mg (0.27 mmol) of tri(tert-butyl)phosphine. The content was stirred at 140° C.

for 14 hours. The reaction mixture was cooled to room temperature, and then 10 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 1.2 g (1.9 mmol) of compound A292 as a light yellow glassy solid (yield: 74%).

The compound was identified by FDMS.
FDMS: 668

Example 8

Synthesis of Compound A124

In a stream of nitrogen, a 50 mL three-necked flask was charged with 3.0 g (6.9 mmol) of 4-chloro-9-(4,6-diphenyl-1,3,5-triazin-2-yl)carbazole, obtained in Synthesis Example 9, 2.2 g (6.9 mmol) of N,N-bis(4-biphenylyl)amine, 0.93 g (9.7 mmol) of sodium tert-butoxide, 20 mL of o-xylene, 31 mg (0.13 mmol) of palladium acetate and 97 mg (0.48 mmol) of tri(tert-butyl)phosphine. The content was stirred at 140° C. for 8 hours. The reaction mixture was cooled to room temperature, and then 10 mL of pure water was added and stirred. The thus-deposited brown powder was collected by filtration, and the collected powder was washed with pure water and then with ethanol. The brown powder was then dried under reduced pressure, and recrystallized from o-xylene to give 2.9 g (4.0 mmol) of compound A124 as a grey powder (yield: 59%).

The compound was identified by FDMS.
FDMS: 717

Example 7

Synthesis of Compound A292

In a stream of nitrogen, a 50 mL three-necked flask was charged with 0.72 g (2.6 mmol) of 4-chloro-9-phenylcarbazole, obtained in Synthesis Example 8, 1.2 g (2.8 mmol) of N-biphenylyl-N-[4-(4-dibenzothienyl)phenyl]amine, 0.35 g (3.6 mmol) of sodium tert-butoxide, 10 mL of o-xylene, 17 mg (0.07 mmol) of palladium acetate and 55 mg (0.27 mmol) of tri(tert-butyl)phosphine. The content was stirred at 140° C. for 14 hours. The reaction mixture was cooled to room temperature, and then 10 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 1.2 g (1.9 mmol) of compound A292 as a light yellow glassy solid (yield: 74%).

The compound was identified by FDMS.
FDMS: 668

Example 8

Synthesis of Compound A124

In a stream of nitrogen, a 50 mL three-necked flask was charged with 3.0 g (6.9 mmol) of 4-chloro-9-(4,6-diphenyl-1,3,5-triazin-2-yl)carbazole, obtained in Synthesis Example 9, 2.2 g (6.9 mmol) of N,N-bis(4-biphenylyl)amine, 0.93 g (9.7 mmol) of sodium tert-butoxide, 20 mL of o-xylene, 31 mg (0.13 mmol) of palladium acetate and 97 mg (0.48 mmol) of tri(tert-butyl)phosphine. The content was stirred at 140° C. for 8 hours. The reaction mixture was cooled to room temperature, and then 10 mL of pure water was added and stirred. The thus-deposited brown powder was collected by filtration, and washed with pure water and then with ethanol. The washed brown powder was dried under reduced pressure. The dried powder was recrystallized from o-xylene to give 2.9 g (4.0 mmol) of compound A124 as a grey powder (yield: 59%).

The compound was identified by FDMS.
FDMS: 717

Example 9

Synthesis of Compound A139

In a stream of nitrogen, a 50 mL three-necked flask was charged with 4.0 g (10.4 mmol) of 4-chloro-9-(2-benzothienyl)carbazole, obtained in Synthesis Example 5, 3.3 g (10.4 mmol) of N,N-bis(4-biphenylyl)amine, 1.4 g (14.6 mmol) of sodium tert-butoxide, 20 mL of o-xylene, 70 mg (0.31 mmol) of palladium acetate and 221 mg (1.0 mmol) of tri(tert-butyl)phosphine. The content was stirred at 140° C. for 6 hours. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 4.2 g (6.3 mmol) of compound A139 as a light yellow glassy solid (yield: 60%).

The compound was identified by FDMS, $^1$H-NMR measurement and $^{13}$C-NMR measurement.
FDMS: 668
$^1$H-NMR (CDCl$_3$); 8.34 (s, 1H), 8.07 (t, 2H), 7.90 (d, 2H), 7.64 (d, 1H), 7.24-7.56 (m, 24H), 7.00-7.12 (m, 2H)
$^{13}$C-NMR (CDCl$_3$); 147.30, 143.82, 141.95, 141.66, 141.29, 140.87, 139.41, 137.72, 135.62, 135.12, 134.90, 129.30, 128.40, 128.02, 127.63, 127.72, 127.17, 126.77, 126.57, 125.36, 124.77, 123.79, 123.66, 122.63, 122.51, 122.19, 121.88, 121.35, 121.30, 120.91, 109.87, 108.13

Example 10

Synthesis of Compound A148

In a stream of nitrogen, a 50 mL three-necked flask was charged with 4.0 g (10.4 mmol) of 4-chloro-9-(2-benzothienyl)carbazole, obtained in Synthesis Example 5, 3.1 g (11.4 mmol) of N-phenyl-N-(2-dibenzothienyl)amine, 3.1 g (11.4 mmol) of sodium tert-butoxide, 20 mL of o-xylene, 70 mg (0.31 mmol) of palladium acetate and 221 mg (1.0 mmol) of tri(tert-butyl)phosphine. The content was stirred at 140° C. for 10 hours. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 4.4 g (7.2 mmol) of compound A148 as a white glassy solid (yield: 70%).

The compound was identified by FDMS, $^1$H-NMR measurement and $^{13}$C-NMR measurement.

FDMS: 622

$^1$H-NMR (CDCl$_3$); 8.34 (s, 1H), 8.07 (t, 2H), 7.98 (s, 1H), 7.86-7.92 (m, 3H), 7.78 (d, 1H), 7.63-7.69 (m, 2H), 6.91-7.53 (m, 16H)

$^{13}$C-NMR (CDCl$_3$); 147.46, 144.73, 142.70, 141.13, 140.82, 139.75, 138.25, 136.59, 136.18, 134.85, 134.52, 133.82, 132.69, 128.79, 126.88, 126.48, 126.13, 125.67, 125.36, 124.23, 123.64, 123.57, 122.89, 122.79, 122.60, 122.54, 122.34, 121.39, 121.31, 121.13, 121.08, 120.69, 120.56, 120.25, 119.85, 119.70, 115.07, 108.72, 106.66

Example 11

Synthesis of Compound A153

In a stream of nitrogen, a 50 mL three-necked flask was charged with 4.0 g (10.4 mmol) of 4-chloro-9-(2-benzothienyl)carbazole, obtained in Synthesis Example 5, 3.8 g (11.4 mmol) of N-phenyl-N-[4-(9-carbazolyl)phenyl]amine, 1.4 g (14.6 mmol) of sodium tert-butoxide, 20 mL of o-xylene, 70 mg (0.31 mmol) of palladium acetate and 221 mg (1.0 mmol) of tri(tert-butyl)phosphine. The content was stirred at 140° C. for 12 hours. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 5.2 g (7.6 mmol) of compound A153 as a white glassy solid (yield: 74%).

The compound was identified by FDMS, $^1$H-NMR measurement and $^{13}$C-NMR measurement.

FDMS: 681

$^1$H-NMR (CDCl$_3$); 8.34 (d, 1H), 8.03-8.12 (m, 4H), 7.90 (d, 2H), 7.65 (d, 1H), 6.99-7.50 (m, 23H)

$^{13}$C-NMR (CDCl$_3$); 146.69, 146.36, 142.74, 140.91, 140.71, 140.54, 139.77, 138.34, 136.62, 134.50, 133.77, 130.05, 128.93, 127.60, 126.92, 126.57, 125.67, 125.54, 125.29, 124.24, 123.69, 122.61, 122.56, 122.36, 122.28, 121.39, 121.30, 121.06, 120.67, 120.29, 119.94, 119.72, 119.12, 109.37, 108.86, 107.07

Example 12

Synthesis of Compound A318

In a stream of nitrogen, a 50 mL three-necked flask was charged with 500 mg (1.1 mmol) of 4-chloro-6-phenyl-9-biphenylylcarbazole, obtained in Synthesis Example 10, 302 mg (1.1 mmol) of N-phenyl-N-(2-dibenzothienyl)amine, 147 mg (1.5 mmol) of sodium tert-butoxide, 10 mL of o-xylene, 7 mg (0.03 mmol) of palladium acetate and 21 mg (0.10 mmol) of tri(tert-butyl)phosphine. The content was stirred at 140° C. for 10 hours. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 411 mg (0.61 mmol) of compound A318 as a white glassy solid (yield: 56%).

The compound was identified by FDMS.

FDMS: 668

Example 13

Synthesis of Compound B1

In a stream of nitrogen, a 200 mL three-necked flask was charged with 7.0 g (19.8 mmol) of 4-chloro-9-(4-biphenylyl)carbazole, obtained in Synthesis Example 3, 0.87 g (9.4 mmol) of aniline, 5.3 g (55.4 mmol) of sodium tert-butoxide, 70 mL of o-xylene, 44 mg (0.19 mmol) of palladium acetate and 139 mg (0.69 mmol) of tri(tert-butyl)phosphine. The content was stirred at 140° C. for 12 hours. The reaction mixture was cooled to room temperature, and then 40 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a mixed solvent (toluene/hexane=1/2 by volume) as a developing solvent to give 5.0 g (6.8 mmol) of compound B1 as a white glassy solid (yield: 72%).

The compound was identified by FDMS, $^1$H-NMR measurement and $^{13}$C-NMR measurement.

FDMS: 727

$^1$H-NMR (CDCl$_3$); 7.78-7.83 (m, 6H), 7.62-7.69 (m, 8H), 7.08-7.51 (m, 18H), 6.77-6.98 (m, 5H)

$^{13}$C-NMR (CDCl$_3$); 143.32, 142.11, 141.51141.07, 140.81, 137.41, 129.92, 129.55, 129.09, 128.38, 128.27, 127.76, 127.39, 126.18, 124.22, 122.52, 120.69, 120.32, 109.83, 107.74

Example 14

Synthesis of Compound B2

In a stream of nitrogen, a 200 mL three-necked flask was charged with 7.0 g (19.8 mmol) of 4-chloro-9-(4-biphenylyl)carbazole, obtained in Synthesis Example 3, 1.0 g (9.4 mmol) of 4-methylaniline, 5.3 g (55.4 mmol) of sodium tert-butoxide, 70 mL of o-xylene, 88 mg (0.39 mmol) of palladium acetate and 279 mg (1.38 mmol) of tri(tert-butyl)phosphine. The content was stirred at 140° C. for 14 hours. The reaction mixture was cooled to room temperature, and then 40 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a toluene/hexane mixed solvent as a developing solvent to give 2.9 g (3.9 mmol) of compound B2 as a light yellow glassy solid (yield: 42%).

The compound was identified by FDMS, $^1$H-NMR measurement and $^{13}$C-NMR measurement.

FDMS: 741

$^1$H-NMR (CDCl$_3$); 7.77-7.85 (m, 6H), 7.61-7.69 (m, 8H), 7.24-7.51 (m, 14H), 7.05 (t, 2H), 6.81-6.95 (m, 6H), 2.20 (s, 3H)

$^{13}$C-NMR (CDCl$_3$); 146.02, 142.74, 142.17, 140.87, 140.41, 140.25, 136.86, 129.83, 128.97, 128.47, 127.80, 127.67, 127.16, 126.70, 125.43, 123.79, 122.07, 120.03, 119.56, 109.14, 106.74, 20.82

Example 15

Synthesis of Compound B27

In a stream of nitrogen, a 50 mL three-necked flask was charged with 4.0 g (12.1 mmol) of 4-chloro-9-(3-quinolyl) carbazole, obtained in Synthesis Example 4, 652 mg (6.0 mmol) of 4-methylaniline, 1.6 g (17.0 mmol) of sodium tert-butoxide, 20 mL of o-xylene, 27 mg (0.12 mmol) of palladium acetate and 85 mg (0.42 mmol) of tri(tert-butyl)phosphine. The content was stirred at 140° C. for 17 hours. The reaction mixture was cooled to room temperature, and then 15 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a toluene/ethyl acetate mixed solvent as a developing solvent to give 2.6 g (3.7 mmol) of compound B27 as a brown glassy solid (yield: 61%).

The compound was identified by FDMS, $^1$H-NMR measurement and $^{13}$C-NMR measurement.

FDMS: 691
$^1$H-NMR (CDCl$_3$); 9.18 (s, 2H), 8.35 (s, 2H), 8.25 (d, 2H), 7.86 (d, 4H), 7.78 (d, 2H), 7.61 (t, 2H), 7.18-7.36 (m, 8H), 7.06 (d, 2H), 6.85-6.98 (m, 6H), 2.22 (s, 3H)
$^{13}$C-NMR (CDCl$_3$); 149.95, 147.15, 145.91, 142.78, 142.41, 140.91, 133.36, 131.37, 130.10, 129.94, 129.63, 128.31, 127.82, 127.67, 127.08, 125.82, 123.93, 122.32, 120.73, 120.00, 119.76, 108.72, 106.23, 20.88

Example 16

Synthesis of Compound B30

In a stream of nitrogen, a 50 mL three-necked flask was charged with 2.7 g (7.0 mmol) of 4-chloro-9-(2-dibenzothienyl)carbazole, obtained in Synthesis Example 5, 297 mg (3.2 mmol) of aniline, 947 mg (9.8 mmol) of sodium tert-butoxide, 13 mL of o-xylene, 15 mg (0.07 mmol) of palladium acetate and 49 mg (0.24 mmol) of tri(tert-butyl)phosphine. The content was stirred at 140° C. for 20 hours. The reaction mixture was cooled to room temperature, and then 10 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a toluene/hexane mixed solvent as a developing solvent to give 0.9 g (1.1 mmol) of compound B30 as a white powder (yield: 35%).

The compound was identified by FDMS, $^1$H-NMR measurement and $^{13}$C-NMR measurement.

FDMS: 787
$^1$H-NMR (CDCl$_3$); 8.33 (s, 2H), 7.99-8.08 (m, 4H), 7.84-7.88 (m, 4H), 7.64 (d, 2H), 7.10-7.50 (m, 16H), 6.79-6.99 (m, 5H)
$^{13}$C-NMR (CDCl$_3$); 148.05, 143.20, 141.66, 141.38, 140.27, 138.71, 137.10, 135.07, 134.46, 129.37, 127.39, 126.90, 126.31, 125.69, 124.74, 124.15, 123.68, 123.05, 121.92, 120.86, 120.16, 119.67, 109.16, 107.03

Example 17

Synthesis of Compound B36

In a stream of nitrogen, a 50 mL three-necked flask was charged with 4.0 g (11.2 mmol) of 4-chloro-9-[4-(2-pyridyl)-phenyl]carbazole, obtained in Synthesis Example 6, 477 mg (9.1 mmol) of aniline, 1.5 g (15.8 mmol) of sodium tert-butoxide, 25 mL of o-xylene, 25 mg (0.11 mmol) of palladium acetate and 79 mg (0.39 mmol) of tri(tert-butyl)phosphine. The content was stirred at 140° C. for 10 hours. The reaction mixture was cooled to room temperature, and then 15 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a toluene/ethyl acetate mixed solvent as a developing solvent to give 2.5 g (3.4 mmol) of compound B36 as a brown glassy solid (yield: 66%).

The compound was identified by FDMS, $^1$H-NMR measurement and $^{13}$C-NMR measurement.

FDMS: 729
$^1$H-NMR (CDCl$_3$); 8.71 (d, 2H), 8.20 (d, 4H), 7.83 (d, 2H), 7.66-7.75 (m, 8H), 7.40 (d, 2H), 7.07-7.32 (m, 12H), 6.77-6.98 (m, 5H)
$^{13}$C-NMR (CDCl$_3$); 156.45, 149.84, 148.03, 142.59, 141.59, 140.80, 138.60, 138.29, 136.93, 129.37, 128.44, 127.67, 126.92, 125.69, 123.66, 122.45, 122.03, 120.56, 120.25, 120.06, 119.81, 109.28, 107.20

Example 18

Synthesis of Compound C5

In a stream of nitrogen, a 100 mL three-necked flask was charged with 3.0 g (9.6 mmol) of 4-chloro-9-(4-chlorophenyl)carbazole, obtained in Synthesis Example 7, 5.2 g (20.2 mmol) of N-(4-methylphenyl)-N-biphenylylamine, 2.5 g (26.9 mmol) of sodium tert-butoxide, 50 mL of o-xylene, 43 mg (0.19 mmol) of palladium acetate and 135 mg (0.67 mmol) of tri(tert-butyl)phosphine. The content was stirred at 140° C. for 12 hours. The reaction mixture was cooled to room temperature, and then 30 mL of pure water was added and stirred. The reaction mixture was separated into an organic phase and an aqueous phase. The organic phase was washed with pure water and then with an aqueous saturated sodium chloride solution. The washed organic phase was dried over anhydrous magnesium sulfate, and then the solvent was distilled off under reduced pressure. The thus-obtained residue was purified by silica gel column chromatography using a toluene/hexane mixed solvent as a developing solvent to give 4.7 g (6.2 mmol) of compound C5 as a colorless glassy solid (yield: 64%).

The compound was identified by FDMS, $^1$H-NMR measurement and $^{13}$C-NMR measurement.

FDMS: 757
$^1$H-NMR (CDCl$_3$); 7.84 (d, 1H), 7.48-7.58 (m, 6H), 7.20-7.37 (m, 18H), 6.96-7.15 (m, 12H), 2.34 (s, 3H), 2.26 (s, 3H)
$^{13}$C-NMR (CDCl$_3$); 147.35, 147.30, 146.93, 144.97, 144.74, 143.01, 141.37, 141.15, 140.83, 140.58, 135.65, 133.84, 133.49, 132.03, 131.00, 130.34, 129.90, 128.82, 128.68, 128.20, 128.00, 127.69, 126.97, 126.73, 126.52, 125.75, 124.24, 123.55, 123.18, 123.05, 121.57, 120.84, 120.45, 120.00, 109.38, 107.36, 21.13, 20.99

Example 19

Synthesis of Compound C11

In a stream of nitrogen, a 200 mL three-necked flask was charged with 6.0 g (19.2 mmol) of 4-chloro-9-(4-chlorophenyl)carbazole, obtained in Synthesis Example 7, 13.0 g (40.5 mmol) of N,N-bis(4-biphenylyl)amine, 5.1 g (54.0 mmol) of sodium tert-butoxide, 60 mL of o-xylene, 86 mg (0.38 mmol) of palladium acetate and 272 mg (1.3 mmol) of tri(tert-butyl) phosphine. The content was stirred at 140° C. for 14 hours. The reaction mixture was cooled to room temperature, and then 40 mL of pure water was added and stirred. The thus-deposited brown powder was collected by filtration, and washed with pure water and then with ethanol. The washed brown powder was dried under reduced pressure. The dried powder was recrystallized from o-xylene to give 10.5 g (11.9 mmol) of compound C11 as a light yellow powder (yield: 62%).

The compound was identified by FDMS.
FDMS: 882

Example 20

Evaluation of Triplet Level of Compound A8

Compound A8 was dissolved in 2-methyltetrahydrofuran to prepare a solution having a concentration of 0.0001 mol/L. Photoluminescence spectroscopy of the solution under liquid nitrogen cooling conditions revealed a maximum phosphorescent wavelength of 480 nm. A triplet level estimated from the maximum phosphorescent wavelength is shown in Table 1, below.

Example 21

Evaluation of Triplet Level of Compound A15

Photoluminescence spectroscopy of compound A15 was carried out by the same procedures as adopted in Example 20. Photoluminescence spectroscopy of a solution of compound A15 revealed a maximum phosphorescent wavelength of 482 nm. A triplet level estimated from the maximum phosphorescent wavelength is shown in Table 1, below.

Example 22

Evaluation of Triplet Level of Compound A278

Photoluminescence spectroscopy of compound A278 was carried out by the same procedures as adopted in Example 20. Photoluminescence spectroscopy of a solution of compound A278 revealed a maximum phosphorescent wavelength of 448 nm. A triplet level estimated from the maximum phosphorescent wavelength is shown in Table 1, below.

Example 23

Evaluation of Triplet Level of Compound A286

Photoluminescence spectroscopy of compound A286 was carried out by the same procedures as adopted in Example 20. Photoluminescence spectroscopy of a solution of compound A286 revealed a maximum phosphorescent wavelength of 486 nm. A triplet level estimated from the maximum phosphorescent wavelength is shown in Table 1, below.

Example 24

Evaluation of Triplet Level of Compound A292

Photoluminescence spectroscopy of compound A292 was carried out by the same procedures as adopted in Example 20. Photoluminescence spectroscopy of a solution of compound A292 revealed a maximum phosphorescent wavelength of 483 nm. A triplet level estimated from the maximum phosphorescent wavelength is shown in Table 1, below.

Example 25

Evaluation of Triplet Level of Compound A124

Photoluminescence spectroscopy of compound A124 was carried out by the same procedures as adopted in Example 20. Photoluminescence spectroscopy of a solution of compound A124 revealed a maximum phosphorescent wavelength of 479 nm. A triplet level estimated from the maximum phosphorescent wavelength is shown in Table 1, below.

Example 26

Evaluation of Triplet Level of Compound A139

Photoluminescence spectroscopy of compound A139 was carried out by the same procedures as adopted in Example 20. Photoluminescence spectroscopy of a solution of compound A139 revealed a maximum phosphorescent wavelength of 480 nm. A triplet level estimated from the maximum phosphorescent wavelength is shown in Table 1, below.

Example 27

Evaluation of Triplet Level of Compound A148

Photoluminescence spectroscopy of compound A148 was carried out by the same procedures as adopted in Example 20. Photoluminescence spectroscopy of a solution of compound A148 revealed a maximum phosphorescent wavelength of 449 nm. A triplet level estimated from the maximum phosphorescent wavelength is shown in Table 1, below.

Example 28

Evaluation of Triplet Level of Compound A153

Photoluminescence spectroscopy of compound A153 was carried out by the same procedures as adopted in Example 20. Photoluminescence spectroscopy of a solution of compound A153 revealed a maximum phosphorescent wavelength of 445 nm. A triplet level estimated from the maximum phosphorescent wavelength is shown in Table 1, below.

Example 29

Evaluation of Triplet Level of Compound A318

Photoluminescence spectroscopy of compound A318 was carried out by the same procedures as adopted in Example 20. Photoluminescence spectroscopy of a solution of compound A318 revealed a maximum phosphorescent wavelength of 457 nm. A triplet level estimated from the maximum phosphorescent wavelength is shown in Table 1, below.

Example 30

Evaluation of Triplet Level of Compound B1

Photoluminescence spectroscopy of compound B1 was carried out by the same procedures as adopted in Example 20. Photoluminescence spectroscopy of a solution of compound B1 revealed a maximum phosphorescent wavelength of 450 nm. A triplet level estimated from the maximum phosphorescent wavelength is shown in Table 1, below.

Example 31

Evaluation of Triplet Level of Compound B2

Photoluminescence spectroscopy of compound B2 was carried out by the same procedures as adopted in Example 20. Photoluminescence spectroscopy of a solution of compound B2 revealed a maximum phosphorescent wavelength of 450 nm. A triplet level estimated from the maximum phosphorescent wavelength is shown in Table 1, below.

Example 32

Evaluation of Triplet Level of Compound B30

Photoluminescence spectroscopy of compound B30 was carried out by the same procedures as adopted in Example 20. Photoluminescence spectroscopy of a solution of compound B30 revealed a maximum phosphorescent wavelength of 442 nm. A triplet level estimated from the maximum phosphorescent wavelength is shown in Table 1, below.

Example 33

Evaluation of Triplet Level of Compound B36

Photoluminescence spectroscopy of compound B36 was carried out by the same procedures as adopted in Example 20. Photoluminescence spectroscopy of a solution of compound B36 revealed a maximum phosphorescent wavelength of 452 nm. A triplet level estimated from the maximum phosphorescent wavelength is shown in Table 1, below.

Comparative Example 1

Evaluation of Triplet Level of NPD

Photoluminescence spectroscopy of NPD was carried out by the same procedures as adopted in Example 20. Photoluminescence spectroscopy of a solution of NPD revealed a maximum phosphorescent wavelength of 525 nm. A triplet level estimated from the maximum phosphorescent wavelength is shown in Table 1, below.

Reference Example 1

Evaluation of Triplet Level of Compound (c)

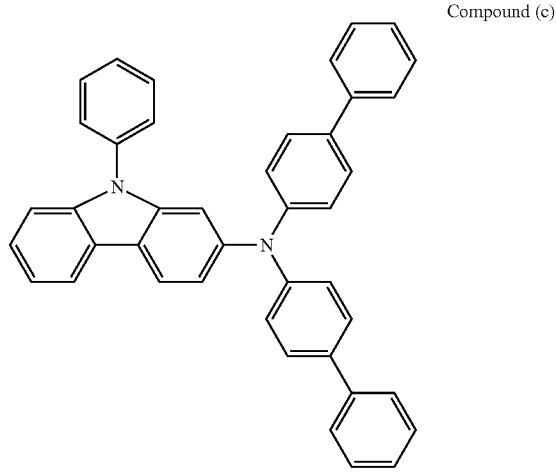 [SMILES: c1ccc(-c2ccc(N(c3ccc(-c4ccccc4)cc3)c3ccc4c5ccccc5n(-c5ccccc5)c4c3)cc2)cc1]

Compound (c)

Photoluminescence spectroscopy of compound (c) was carried out by the same procedures as adopted in Example 20. Photoluminescence spectroscopy of a solution of compound (c) revealed a maximum phosphorescent wavelength of 490 nm. A triplet level estimated from the maximum phosphorescent wavelength is shown in Table 1, below.

The compounds of the present invention exhibited triplet levels higher than those of NPD and compound (c).

TABLE 1

| | Compound | Triplet level (eV) |
|---|---|---|
| Example 20 | A8 | 2.58 |
| Example 21 | A15 | 2.57 |
| Example 22 | A278 | 2.76 |
| Example 23 | A286 | 2.56 |
| Example 24 | A292 | 2.56 |
| Example 25 | A124 | 2.58 |
| Example 26 | A139 | 2.58 |
| Example 27 | A148 | 2.76 |
| Example 28 | A153 | 2.78 |
| Example 29 | A318 | 2.71 |
| Example 30 | B1 | 2.75 |
| Example 31 | B2 | 2.75 |
| Example 32 | B30 | 2.80 |
| Example 33 | B36 | 2.74 |
| Comp. Ex. 1 | NPD | 2.36 |
| Ref. Ex. 1 | Compound (c) | 2.53 |

Example 34

Evaluation of Ionization Potential of Compound A5

Tetrabutylammonium perchlorate was dissolved in anhydrous dichloromethane to prepare a solution having a concentration of 0.1 mol/L. Compound A5 was dissolved in the tetrabutylammonium perchlorate solution to prepare a solution having a concentration of 0.001 mol/L. Ionization potential of compound A5 was measured by cyclic voltammetry. In the cyclic voltammetry, glassy carbon was used as a working electrode, a platinum wire was used as a counter electrode, and a silver wire dipped in a AgNO3 solution in acetonitrile was used as a reference electrode. Ferrocene was used as a reference substance.

The cyclic voltammetry revealed that the ionization potential of compound A5 was 0.43 V vs. Fc/Fc$^+$ as expressed as the oxidation-reduction potential of ferrocene being reference potential. This ionization potential of compound A5 is slightly larger than the ionization potential (0.31 V vs. Fc/Fc$^+$) of NPD which is conventionally used as a hole transport material. Thus ionization potential of compound A5 is suitable for hole transport material.

Example 35

Evaluation of Ionization Potential of Compound A8

Ionization potential of compound A8 was measured by the same procedures as described in Example 34. The ionization potential of compound A8 was 0.44 V vs. Fc/Fc$^+$ as expressed as the oxidation-reduction potential of ferrocene being reference potential. This ionization potential of compound A8 is slightly larger than the ionization potential (0.31 V vs. Fc/Fc$^+$) of NPD conventionally used as a hole transport material. Thus ionization potential of compound A8 is suitable for hole transport material.

Example 36

Evaluation of Ionization Potential of Compound A15

Ionization potential of compound A15 was measured by the same procedures as described in Example 34. The ionization potential of compound A15 was 0.40 V vs. Fc/Fc$^+$ as expressed as the oxidation-reduction potential of ferrocene being reference potential. This ionization potential of compound A15 is slightly larger than the ionization potential (0.31 V vs. Fc/Fc$^+$) of NPD conventionally used as a hole transport material. Thus ionization potential of compound A15 is suitable for hole transport material.

Example 37

Evaluation of Ionization Potential of Compound A278

Ionization potential of compound A278 was measured by the same procedures as described in Example 34. The ionization potential of compound A278 was 0.45 V vs. Fc/Fc$^+$ as expressed as the oxidation-reduction potential of ferrocene being reference potential. This ionization potential of compound A278 is slightly larger than the ionization potential (0.31 V vs. Fc/Fc$^+$) of NPD conventionally used as a hole transport material. Thus ionization potential of compound A278 is suitable for hole transport material.

Example 38

Evaluation of Ionization Potential of Compound A286

Ionization potential of compound A286 was measured by the same procedures as described in Example 34. The ionization potential of compound A286 was 0.44 V vs. Fc/Fc$^+$ as expressed as the oxidation-reduction potential of ferrocene being reference potential. This ionization potential of compound A286 is slightly larger than the ionization potential (0.31 V vs. Fc/Fc$^+$) of NPD conventionally used as a hole transport material. Thus ionization potential of compound A286 is suitable for hole transport material.

Example 39

Evaluation of Ionization Potential of Compound A289

Ionization potential of compound A289 was measured by the same procedures as described in Example 34. The ionization potential of compound A289 was 0.39 V vs. Fc/Fc$^+$ as expressed as the oxidation-reduction potential of ferrocene being reference potential. This ionization potential of compound A289 is slightly larger than the ionization potential (0.31 V vs. Fc/Fc$^+$) of NPD conventionally used as a hole transport material. Thus ionization potential of compound A289 is suitable for hole transport material.

Example 40

Evaluation of Ionization Potential of Compound A292

Ionization potential of compound A292 was measured by the same procedures as described in Example 34. The ionization potential of compound A292 was 0.43 V vs. Fc/Fc$^+$ as expressed as the oxidation-reduction potential of ferrocene being reference potential. This ionization potential of compound A292 is slightly larger than the ionization potential (0.31 V vs. Fc/Fc$^+$) of NPD conventionally used as a hole transport material. Thus ionization potential of compound A292 is suitable for hole transport material.

Example 41

Evaluation of Ionization Potential of Compound A124

Ionization potential of compound A124 was measured by the same procedures as described in Example 34. The ionization potential of compound A124 was 0.44 V vs. Fc/Fc$^+$ as expressed as the oxidation-reduction potential of ferrocene being reference potential. This ionization potential of compound A124 is slightly larger than the ionization potential (0.31 V vs. Fc/Fc$^+$) of NPD conventionally used as a hole transport material. Thus ionization potential of compound A124 is suitable for hole transport material.

Example 42

Evaluation of Ionization Potential of Compound A139

Ionization potential of compound A139 was measured by the same procedures as described in Example 34. The ionization potential of compound A139 was 0.45 V vs. Fc/Fc$^+$ as expressed as the oxidation-reduction potential of ferrocene being reference potential. This ionization potential of compound A139 is slightly larger than the ionization potential (0.31 V vs. Fc/Fc$^+$) of NPD conventionally used as a hole transport material. Thus ionization potential of compound A139 is suitable for hole transport material.

Example 43

Evaluation of Ionization Potential of Compound A148

Ionization potential of compound A148 was measured by the same procedures as described in Example 34. The ionization potential of compound A148 was 0.45 V vs. Fc/Fc$^+$ as expressed as the oxidation-reduction potential of ferrocene being reference potential. This ionization potential of compound A148 is slightly larger than the ionization potential (0.31 V vs. Fc/Fc$^+$) of NPD conventionally used as a hole transport material. Thus ionization potential of compound A148 is suitable for hole transport material.

Example 44

Evaluation of Ionization Potential of Compound A153

Ionization potential of compound A153 was measured by the same procedures as described in Example 34. The ionization potential of compound A153 was 0.47 V vs. Fc/Fc$^+$ as expressed as the oxidation-reduction potential of ferrocene being reference potential. This ionization potential of compound A153 is slightly larger than the ionization potential (0.31 V vs. Fc/Fc$^+$) of NPD conventionally used as a hole transport material. Thus ionization potential of compound A153 is suitable for hole transport material.

Example 45

Evaluation of Ionization Potential of Compound A318

Ionization potential of compound A318 was measured by the same procedures as described in Example 34. The ionization potential of compound A318 was 0.44 V vs. Fc/Fc$^+$ as expressed as the oxidation-reduction potential of ferrocene being reference potential. This ionization potential of compound A318 is slightly larger than the ionization potential (0.31 V vs. Fc/Fc$^+$) of NPD conventionally used as a hole transport material. Thus ionization potential of compound A318 is suitable for hole transport material.

Example 46

Evaluation of Ionization Potential of Compound B1

Ionization potential of compound B1 was measured by the same procedures as described in Example 34. The ionization potential of compound B1 was 0.48 V vs. Fc/Fc$^+$ as expressed as the oxidation-reduction potential of ferrocene being reference potential. This ionization potential of compound B1 is slightly larger than the ionization potential (0.31 V vs. Fc/Fc$^+$) of NPD conventionally used as a hole transport material. Thus ionization potential of compound B1 is suitable for hole transport material.

Example 47

Evaluation of Ionization Potential of Compound B2

Ionization potential of compound B2 was measured by the same procedures as described in Example 34. The ionization potential of compound B2 was 0.46 V vs. Fc/Fc$^+$ as expressed as the oxidation-reduction potential of ferrocene being reference potential. This ionization potential of compound B2 is slightly larger than the ionization potential (0.31 V vs. Fc/Fc$^+$) of NPD conventionally used as a hole transport material. Thus ionization potential of compound B2 is suitable for hole transport material.

Example 48

Evaluation of Ionization Potential of Compound B27

Ionization potential of compound B27 was measured by the same procedures as described in Example 34. The ionization potential of compound B27 was 0.48 V vs. Fc/Fc$^+$ as expressed as the oxidation-reduction potential of ferrocene being reference potential. This ionization potential of compound B27 is slightly larger than the ionization potential (0.31 V vs. Fc/Fc$^+$) of NPD conventionally used as a hole transport material. Thus ionization potential of compound B27 is suitable for hole transport material.

Example 49

Evaluation of Ionization Potential of Compound B30

Ionization potential of compound B30 was measured by the same procedures as described in Example 34. The ionization potential of compound B30 was 0.48 V vs. Fc/Fc$^+$ as expressed as the oxidation-reduction potential of ferrocene being reference potential. This ionization potential of compound B30 is slightly larger than the ionization potential (0.31 V vs. Fc/Fc$^+$) of NPD conventionally used as a hole transport material. Thus ionization potential of compound B30 is suitable for hole transport material.

Example 50

Evaluation of Ionization Potential of Compound B36

Ionization potential of compound B36 was measured by the same procedures as described in Example 34. The ionization potential of compound B36 was 0.48 V vs. Fc/Fc$^+$ as expressed as the oxidation-reduction potential of ferrocene being reference potential. This ionization potential of compound B36 is slightly larger than the ionization potential (0.31 V vs. Fc/Fc$^+$) of NPD conventionally used as a hole transport material. Thus ionization potential of compound B36 is suitable for hole transport material.

Example 51

Evaluation of Ionization Potential of Compound C5

Ionization potential of compound C5 was measured by the same procedures as described in Example 34. The ionization potential of compound C5 was 0.40 V vs. Fc/Fc$^+$ as expressed as the oxidation-reduction potential of ferrocene being reference potential. This ionization potential of compound C5 is slightly larger than the ionization potential (0.31 V vs. Fc/Fc$^+$) of NPD conventionally used as a hole transport material. Thus ionization potential of compound C5 is suitable for hole transport material.

Example 52

Evaluation of Ionization Potential of Compound C11

Ionization potential of compound C11 was measured by the same procedures as described in Example 34. The ionization potential of compound C11 was 0.45 V vs. Fc/Fc⁺ as expressed as the oxidation-reduction potential of ferrocene being reference potential. This ionization potential of compound C11 is slightly larger than the ionization potential (0.31 V vs. Fc/Fc⁺) of NPD conventionally used as a hole transport material. Thus ionization potential of compound C11 is suitable for hole transport material.

Comparative Example 2

Evaluation of Ionization Potential of Compound (a)

Compound (a)

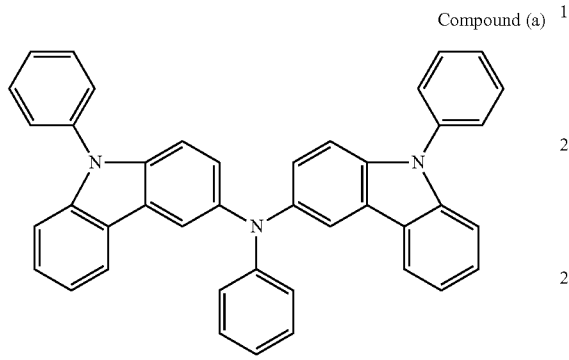

Ionization potential of compound (a) having an amino group at 3-position of the carbazole ring was measured by the same procedures as described in Example 34. The ionization potential of compound (a) was 0.13 V vs. Fc/Fc⁺ as expressed as the oxidation-reduction potential of ferrocene being reference potential. This ionization potential of compound (a) is smaller than the ionization potential (0.31 V vs. Fc/Fc⁺) of NPD conventionally used as a hole transport material. Thus compound (a) as a hole transport material is not preferable to NPD.

Example 53

Measurement of Glass Transition Temperature of Compound A139

5 mg of compound A139 was placed in an aluminum pan, and glass transition temperature of compound A139 was measured at a temperature elevating rate of 10° C./min in a nitrogen atmosphere. The glass transition temperature of compound A139 was 150° C. This glass transition temperature was higher than those of NPD (96° C.) and compound (b), shown below, (100° C.). Thus a film of compound A139 was proved to have enhanced stability as compared with films of NPD and compound (b).

Example 54

Measurement of Glass Transition Temperature of Compound A148

Glass transition temperature of compound A148 was measured by the same procedures as described in Example 53. The glass transition temperature of compound A148 was 142° C. This glass transition temperature was higher than those of NPD (96° C.) and compound (b), shown below, (100° C.). Thus a film of compound A148 was proved to have enhanced stability as compared with films of NPD and compound (b).

Example 55

Measurement of Glass Transition Temperature of Compound A153

Glass transition temperature of compound A153 was measured by the same procedures as described in Example 53. The glass transition temperature of compound A153 was 150° C. This glass transition temperature was higher than those of NPD (96° C.) and compound (b), shown below, (100° C.). Thus a film of compound A153 was proved to have enhanced stability as compared with films of NPD and compound (b).

Example 56

Measurement of Glass Transition Temperature of Compound B1

Glass transition temperature of compound B1 was measured by the same procedures as described in Example 53. The glass transition temperature of compound B1 was 169° C. This glass transition temperature was higher than those of NPD (96° C.) and compound (b), shown below, (100° C.). Thus a film of compound B1 was proved to have enhanced stability as compared with films of NPD and compound (b).

Example 57

Measurement of Glass Transition Temperature of Compound B30

Glass transition temperature of compound B30 was measured by the same procedures as described in Example 53. The glass transition temperature of compound B30 was 191° C. This glass transition temperature was higher than those of NPD (96° C.) and compound (b), shown below, (100° C.). Thus a film of compound B30 was proved to have enhanced stability as compared with films of NPD and compound (b).

Example 58

Evaluation of Organic EL Device Using Compound A5

A glass substrate having a transparent indium-tin oxide (ITO) electrode (anode) laminated layer with a thickness of 200 nm was subjected to ultrasonic cleaning using acetone and pure water, and then boiling cleaning using isopropyl alcohol. Then the glass substrate was surface-treated by irradiation with ozone-ultraviolet rays. The surface-treated glass substrate was placed in a vacuum deposition apparatus, and the apparatus was evacuated to a pressure below $5 \times 10^{-4}$ Pa by a vacuum pump.

Copper phthalocyanine(II) was vacuum-deposited on the transparent ITO electrode of the glass substrate at a deposition rate of 0.1 nm/sec to form a hole injection layer having a thickness of 10 nm. Then NPD was vacuum-deposited into a thickness of 25 nm at a deposition rate of 0.3 nm/sec, and further compound A5 was vacuum-deposited into a thickness of 5 nm at a deposition rate of 0.1 nm/sec, whereby a double hole transport layer was formed on the hole injection layer.

Then a phosphorescent dopant material Ir(ppy)₃ [tris(2-phenylpyridine)iridium] and a host material CBP [4,4'-bis(N-carbazolyl)biphenyl] were co-vacuum-deposited at a weight ratio of 1:11.5 and a deposition rate of 0.25 nm/sec, thereby forming an emitting layer having a thickness of 30 nm.

BAlq [bis(2-methyl-8-quinolinolato) (p-phenylphenolato)-aluminum] was then vacuum-deposited at a deposition rate of 0.3 nm/sec to form an exciton-blocking layer having a thickness of 5 nm. Then, Alq$_3$ [tris(8-quinolinolato)aluminum] was then vacuum-deposited at a deposition rate of 0.3 nm/sec to form an electron transport layer having a thickness of 45 nm. Further, lithium fluoride was vacuum-deposited at a deposition rate of 0.01 nm/sec to form an electron injection layer having a thickness of 0.5 nm, and aluminum was vacuum-deposited to form a cathode having a thickness of 100 nm. Finally the thus-obtained multi-layer structure was encapsulated with a sealing glass cap and a ultraviolet ray-curable resin in a nitrogen atmosphere, whereby an organic EL device for testing was manufactured.

An electric current was applied to the organic EL device at a current density of 20 mA/cm$^2$, and drive voltage and current efficiency were measured. The results are shown in Table 2, below.

Example 59

Evaluation of Organic EL Device Using Compound A8

An organic EL device was manufactured and evaluated by the same procedures as described in Example 58 except that compound A8 was used instead of compound A5. Drive voltage and current efficiency of the device as measured at a current density of 20 mA/cm$^2$ are shown in Table 2, below.

Example 60

Evaluation of Organic EL Device Using Compound A15

An organic EL device was manufactured and evaluated by the same procedures as described in Example 58 except that compound A15 was used instead of compound A5. Drive voltage and current efficiency of the device as measured at a current density of 20 mA/cm$^2$ are shown in Table 2, below.

Example 61

Evaluation of Organic EL Device Using Compound A278

An organic EL device was manufactured and evaluated by the same procedures as described in Example 58 except that compound A278 was used instead of compound A5. Drive voltage and current efficiency of the device as measured at a current density of 20 mA/cm$^2$ are shown in Table 2, below.

Example 62

Evaluation of Organic EL Device Using Compound A139

An organic EL device was manufactured and evaluated by the same procedures as described in Example 58 except that compound A139 was used instead of compound A5. Drive voltage and current efficiency of the device as measured at a current density of 20 mA/cm$^2$ are shown in Table 2, below.

Example 63

Evaluation of Organic EL Device Using Compound A148

An organic EL device was manufactured and evaluated by the same procedures as described in Example 58 except that compound A148 was used instead of compound A5. Drive voltage and current efficiency of the device as measured at a current density of 20 mA/cm$^2$ are shown in Table 2, below.

Example 64

Evaluation of Organic EL Device Using Compound A153

An organic EL device was manufactured and evaluated by the same procedures as described in Example 58 except that compound A153 was used instead of compound A5. Drive voltage and current efficiency of the device as measured at a current density of 20 mA/cm$^2$ are shown in Table 2, below.

Example 65

Evaluation of Organic EL Device Using Compound B2

An organic EL device was manufactured and evaluated by the same procedures as described in Example 58 except that compound B2 was used instead of compound A5. Drive voltage and current efficiency of the device as measured at a current density of 20 mA/cm$^2$ are shown in Table 2, below.

Example 66

Evaluation of Organic EL Device Using Compound B27

An organic EL device was manufactured and evaluated by the same procedures as described in Example 58 except that compound B27 was used instead of compound A5. Drive voltage and current efficiency of the device as measured at a current density of 20 mA/cm$^2$ are shown in Table 2, below.

Example 67

Evaluation of Organic EL Device Using Compound B30

An organic EL device was manufactured and evaluated by the same procedures as described in Example 58 except that compound B30 was used instead of compound A5. Drive voltage and current efficiency of the device as measured at a current density of 20 mA/cm$^2$ are shown in Table 2, below.

Example 68

Evaluation of Organic EL Device Using Compound B36

An organic EL device was manufactured and evaluated by the same procedures as described in Example 58 except that compound B36 was used instead of compound A5. Drive voltage and current efficiency of the device as measured at a current density of 20 mA/cm$^2$ are shown in Table 2, below.

Example 69

Evaluation of Organic EL Device Using Compound C5

An organic EL device was manufactured and evaluated by the same procedures as described in Example 58 except that compound C5 was used instead of compound A5. Drive voltage and current efficiency of the device as measured at a current density of 20 mA/cm² are shown in Table 2, below.

Comparative Example 3

A comparative organic EL device was manufactured and evaluated by the same procedures as described in Example 58 except that NPD was used instead of compound A5. Drive voltage and current efficiency of the device as measured at a current density of 20 mA/cm² are shown in Table 2, below.

Comparative Example 4

A comparative organic EL device was manufactured and evaluated by the same procedures as described in Example 58 except that compound (a) was used instead of compound A5. Drive voltage and current efficiency of the device as measured at a current density of 20 mA/cm² are shown in Table 2, below.

Reference Example 2

A comparative organic EL device was manufactured and evaluated by the same procedures as described in Example 58 except that compound (b) represented by the following formula was used instead of compound A5.

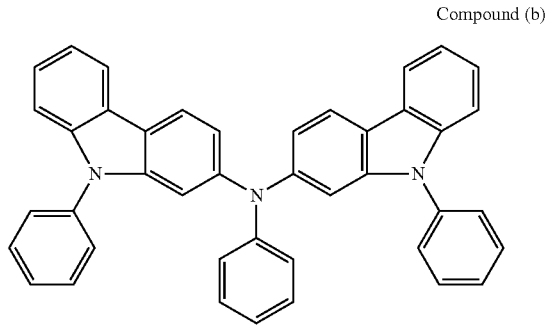 [SMILES: c1ccc(N(c2ccc3c4ccccc4n(-c4ccccc4)c3c2)c2ccc3c4ccccc4n(-c4ccccc4)c3c2)cc1]

Compound (b)

Drive voltage and current efficiency of the device as measured at a current density of 20 mA/cm² are shown in Table 2, below.

The 4-aminocarbazole compound of the present invention exhibited high current efficiency (thus high emitting efficiency) as compared with compound (a) and compound (b). The organic EL device manufactured using the 4-aminocarbazole compound of the present invention exhibited reduced drive voltage.

TABLE 2

|  | Compound in hole transport layer | Drive voltage (V) | Current efficiency (cd/A) |
|---|---|---|---|
| Example 58 | A5 | 8.2 | 38 |
| Example 59 | A8 | 8.4 | 39 |
| Example 60 | A15 | 8.1 | 37 |
| Example 61 | A278 | 8.7 | 39 |
| Example 62 | A139 | 8.3 | 38 |
| Example 63 | A148 | 8.6 | 41 |
| Example 64 | A153 | 8.7 | 42 |
| Example 65 | B2 | 8.4 | 40 |
| Example 66 | B27 | 8.8 | 38 |
| Example 67 | B30 | 8.2 | 41 |
| Example 68 | B36 | 8.5 | 39 |
| Example 69 | C5 | 8.3 | 38 |
| Comp. Ex. 3 | NPD | 9.2 | 28 |
| Comp. Ex. 4 | Compound (a) | 9.4 | 28 |
| Ref. Ex. 2 | Compound (b) | 9.1 | 33 |

Industrial Applicability

A fluorescent or phosphorescent organic EL device having at least one layer comprising the 4-aminocarbazole compound according to the present invention exhibits unforeseen benefits such as high luminous efficiency and high current efficiency, and reduced drive voltage, as compared with organic EL devices comprising a conventional luminous material having a chemical structure comprising a carbazole ring. Therefore, the 4-aminocarbazole compound of the present invention gives a fluorescent or phosphorescent organic EL device exhibiting enhanced brightness and reduced power consumption.

The invention claimed is:

1. A 4-aminocarbazole compound represented by the following general formula (1):

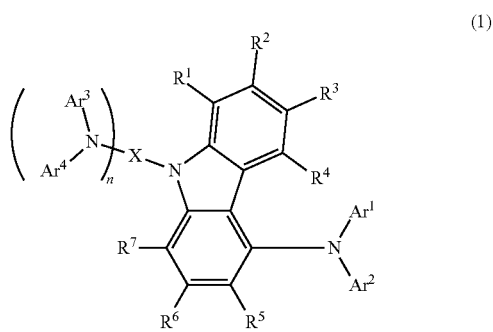

(1)

wherein, $Ar^1$ through $Ar^4$ independently represent an aryl group having 6 to 30 carbon atoms, a thienyl group, a pyridyl group, a benzothienyl group, a dibenzothienyl group, a dibenzofuranyl group, a 4-carbazolyl group, a dibenzothienylphenyl group, a dibenzofuranylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 11 carbon atoms, a trialkylsilyl group having 3 to 18 carbon atoms, a triarylsilyl group having 18 to 40 carbon atoms, a cyano group and a halogen atom;

$R^1$ through $R^7$ independently represent an aryl group having 6 to 30 carbon atoms, a heteroaryl group having 3 to 20 carbon atoms, a heteroaryiphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 30 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom; or $R^1$ through $R^7$ independently represent a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms;

n represents an integer of 0 to 2; and

X represents an (n+1)-valent aromatic hydrocarbon group having 6 to 17 carbon atoms, an (n+1)-valent heteroaromatic group having 3 to 20 carbon atoms or an (n+1)-valent heteroarylphenyl group having 9 to 26 carbon atoms, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a halogenated alkyl group having 1 to 3 carbon atoms, a halogenated alkoxy group having 1 to 3 carbon atoms, an aryl group having 6 to 12 carbon atoms, an aryloxy group having 6 to 18 carbon atoms, a heteroaryl group having 3 to 20 carbon atoms, a trialkylsilyl group having 3 to 18 carbon atoms, a triarylsilyl group having 18 to 40 carbon atoms, a cyano group and a halogen atom.

2. The 4-aminocarbazole compound according to claim 1, wherein $R^1$ through $R^7$ independently represent an aryl group having 6 to 30 carbon atoms, a heteroaryl group having 3 to 20 carbon atoms, a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, a cyano group, a hydrogen atom or a halogen atoms.

3. The 4-aminocarbazole compound according to claim 1, wherein $R^1$ through $R^7$ independently represent a phenyl group, a methylphenyl group, a methoxyphenyl group, a biphenylyl group, a dibenzothienyl group, a dibenzofuranyl group, a methyl group, a methoxy group or a hydrogen atom.

4. The 4-aminocarbazole compound according to claim 1, wherein $R^1$ through $R^7$ independently represent a phenyl group, a methylphenyl group, a methoxyphenyl group or a hydrogen atom.

5. The 4-aminocarbazole compound according to claim 1, wherein $R^4$, $R^5$, $R^6$ and $R^7$ represent a hydrogen atom.

6. The 4-aminocarbazole compound according to claim 1, wherein $R^1$, $R^2$, $R^4$, $R^5$, $R^6$ and $R^7$ represent a hydrogen atom.

7. The 4-aminocarbazole compound according to claim 1, wherein $Ar^1$ through $Ar^4$ independently represent an aryl group having 6 to 30 carbon atoms, a dibenzothienyl group, a dibenzofuranyl group, a 4-carbazolyl group, a dibenzofuranylphenyl group or a dibenzothienylphenyl group or a 9-carbazolylphenyl group, and these groups may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 30 carbon atoms and a heteroaryl group having 3 to 11 carbon atoms.

8. The 4-aminocarbazole compound according to claim 1, wherein $Ar^1$ through $Ar^4$ independently represent a phenyl group, a biphenylyl group, a terphenylyl group, a fluorenyl group, a benzofluorenyl group, a dibenzothienyl group, a dibenzofuranyl group, a dibenzofuranylphenyl group, a dibenzothienylphenyl group or a 9-carbazoylphenyl group, and these groups may independently have at least one substituent selected from the group consisting of a methyl group, an ethyl group, a straight, branched or cyclic alkyl group having 3 to 18 carbon atoms, a methoxy group, an ethoxy group and a straight, branched or cyclic alkoxy group having 3 to 18 carbon atoms; or $Ar^1$ through $Ar^4$ independently represent a 4-carbazolyl group which may independently have at least one substituent selected from the group consisting of a methyl group, an ethyl group, a straight, branched or cyclic alkyl group having 3 to 18 carbon atoms, a methoxy group, an ethoxy group, a straight, branched or cyclic alkoxy group having 3 to 18 carbon atoms, an aryl group having 6 to 30 carbon atoms and a heteroaryl group having 3 to 11 carbon atoms.

9. The 4-aminocarbazole compound according to claim 1, wherein $Ar^1$ through $Ar^4$ independently represent a phenyl group, a methylphenyl group, a methoxyphenyl group, a biphenylyl group, a terphenylyl group, a 9,9'-dimethylfluorenyl group, a 11,11'-dimethylbenzo[a]fluorenyl group, a dibenzothienyl group, a dibenzofuranyl group, a dibenzothienylphenyl group, a 4-(9-carbazoyl)phenyl group, a 9-phenylcarbazol-4-yl group, a 9-biphenylylcarbazol-4-yl group, a 9-quinolylcarbazol-4-yl group or a 9-dibenzothienylcarbazol-4-yl group.

10. The 4-aminocarbazole compound according to claim 1, wherein X represents an aromatic group selected from the group consisting of (n+1)-valent benzene, (n+1)-valent biphenyl, (n+1)-valent naphthalene, (n+1)-valent phenanthrene, (n+1)-valent fluorene, (n+1)-valent naphthylbenzene, (n+1)-valent pyridine, (n+1)-valent pyrimidine, (n+1)-valent 1,3,5-triazine, (n+1)-valent quinoline, (n+1)-valent dibenzothiophene, (n+1)-valent dibenzofuran, (n+1)-valent pyridylbenzene, (n+1)-valent imidazolylbenzene, (n+1)-valent benzoimidazolylbenzene and (n+1)-valent benzothiazolylbenzene, and these aromatic groups may independently have at least one substituent selected from the group consisting of a methyl group, an ethyl group, a straight, branched or cyclic alkyl group having 3 to 18 carbon atoms, a methoxy group, an ethoxy group and a straight, branched or cyclic alkoxy group having 3 to 18 carbon atoms, an aryl group having 6 to 12 carbon atoms, a heteroaryl group having 3 to 20 carbon atoms, a cyano group and a halogen atom.

11. The 4-aminocarbazole compound according to claim 1, wherein X represents an aromatic group selected from the group consisting of (n+1)-valent benzene, (n+1)-valent biphenyl, (n+1)- valent quinoline, (n+1)-valent dibenzothiophene, (n+1)-valent 1,3,5-triazine and (n+1)-valent pyridylbenzene, and these aromatic groups may independently have at least one substituent selected from the group consisting of a methyl group, an ethyl group, a straight, branched or cyclic alkyl group having 3 to 18 carbon atoms, a methoxy group, an ethoxy group and a straight, branched or cyclic alkoxy group having 3 to 18 carbon atoms, an aryl group having 6 to 12 carbon atoms, a cyano group and a halogen atom.

12. The 4-aminocarbazole compound according to claim 1, wherein X represents (n+1)-valent benzene, (n+1)-valent biphenyl, (n+1)-valent quinoline, (n+1)-valent dibenzothiophene, (n+1)-valent 2,4-diphenyl-1,3,5-triazine or (n+1)-valent pyridylbenzene.

13. The 4-aminocarbazole compound according to claim 1, wherein n represents an integer of 0 or 1.

14. An organic electroluminescent device having at least one layer selected from the group consisting of a luminescent layer, a hole transport layer and a hole injection layer, said at least one layer comprising a 4-aminocarbazole compound as claimed in claim 1.

15. A hole transport material or a hole injection material, which comprises a 4-aminocarbazole compound as claimed in claim 1.

* * * * *